US008269063B2

(12) United States Patent
Frohberg et al.

(10) Patent No.: US 8,269,063 B2
(45) Date of Patent: Sep. 18, 2012

(54) METHODS FOR IDENTIFYING PROTEINS WITH STARCH PHOSPHORYLATING ENZYMATIC ACTIVITY

(75) Inventors: Claus Frohberg, Kleinmachnow (DE); Oliver Koetting, Zürich (CH); Gerhard Ritte, Potsdam (DE); Martin Steup, Berlin (DE)

(73) Assignee: Bayer Cropscience AG, Monheim (DE)

( * ) Notice: Subject to any disclaimer, the term of this patent is extended or adjusted under 35 U.S.C. 154(b) by 985 days.

(21) Appl. No.: 10/591,419

(22) PCT Filed: Mar. 4, 2005

(86) PCT No.: PCT/EP2005/002454
§ 371 (c)(1),
(2), (4) Date: May 9, 2008

(87) PCT Pub. No.: WO2005/095632
PCT Pub. Date: Oct. 13, 2005

(65) Prior Publication Data
US 2008/0276336 A1    Nov. 6, 2008

(30) Foreign Application Priority Data

Mar. 5, 2004   (EP) .................... 04090087
Mar. 29, 2004  (EP) .................... 04090121
Dec. 9, 2004   (EP) .................... 04090483

(51) Int. Cl.
C12N 15/82    (2006.01)
C12N 15/00    (2006.01)
C12N 15/10    (2006.01)
C07H 21/04    (2006.01)

(52) U.S. Cl. ............ 800/284; 800/278; 435/320.1; 536/23.6; 536/23.1; 536/23.2

(58) Field of Classification Search ............ None
See application file for complete search history.

(56) References Cited

U.S. PATENT DOCUMENTS 6,096,504 A     8/2000  McGonigle et al.
2006/0123505 A1*  6/2006  Kikuchi et al. ............. 800/278

FOREIGN PATENT DOCUMENTS

| WO | WO 96/27674   | 9/1996  |
| WO | WO 97/11188   | 3/1997  |
| WO | WO 00/77229   | 12/2000 |
| WO | WO 02/10210 A2 | 2/2002  |
| WO | WO 02/22675 A2 | 3/2002  |
| WO | WO 02/34923 A2 | 5/2002  |
| WO | WO 2005/095632 | 10/2005 |

OTHER PUBLICATIONS

Blennow et al. (2000) "The distribution of covalently bound phosphate in the starch granule in relation to starch crystallnity." *International Journal of Biological Macromolecules* 27: 211-218.
Blennow et al. (2000) "Starch molecular structure and phosphorylation investigated by a combined chromatographic and chemometric approach." *Carbohydrate Polymers* 41: 163-174.
Jane et al. (Nov./Dec. 1996) "Phosphorus in Rice and Other Starches." *Cereal Foods World* 41(11): 827-832.
KÖtting et al. (Jan. 2005) "Identification of a Novel Enzyme Required for Starch Metabolism in Arabidopsis Leaves. The Phosphoglucan, Water Dikinase[1[w]]." *Plant Physiology* 137: 242-252.
Lorberth et al. (May 1998) "Inhibition of a starch-granule-bound protein leads to modified starch and repression of cold sweetening." *Nature Biotechnology* 16: 473-477.
Mikkelsen et al. (2004) "Functional characterization of α-glucan, water dikinase, the starch phosphorylating enzyme." *Biochem. J.* 377: 525-532.
Ritte et al. (2003) "Determination of the starch-phosphorylating enzyme activity in plant extracts." *Planta* 216(5): 798-801.
Ritte et al. (May 14, 2002) "The starch-related R1 protein is an α-glucan, water dikinase." *PNAS* 99(10):7166-7171.
Tabata et al. (1971) "Studies on Starch Posphate." *Starch/Stärke* 23: 267-272.
Alonso et al. (Aug. 1, 2003) "Genome-Wide Insertional Mutagenesis of Arabidopsis thaliana" *Science* 301: 653-657.
Baunsgaard et al. (2005) "A novel Isoform of Glucan, Water Dikinase Phosphorylates Pre-Phosphorylated α-glucans and is Involved in Starch Degradation in Arabidopsis." *The Plant Journal* 41: 595-605.
Blennow et al. (Oct. 2002) "Starch phosphorylation: a new front line in starch research." *Trends in Plant Science* 7(10): 445-450.
GenPept Accession No. B29959 (Jun. 18, 1999).
GenPept Accession No. S01446 (Jul. 21, 2000).
GenBank Accession No. Y09533 (Jul. 22, 2003).
GenBank Accession No. AY027522 (Feb. 26, 2001).
GenPept Accession No. AAN93923 (Dec. 20, 2002).
GenPept Accession No. AR236165 (Dec. 20, 2002).
GenBank Accession No. AR400813 (Dec. 18, 2003).
GenPept Accession No. AAR61444 (Dec. 18, 2003).
GenBank Accession No. AR400184 (Dec. 18, 2003).
GenPept Accession No. AAR61445 (Dec. 18, 2003).
GenBank Accession No. AR400815 (Dec. 18, 2003).
GenPept Accession No. AAR61446 (Dec. 18, 2003).
GenBank Accession No. AY094062 (Jul. 23, 2003).
GenBank Accession No. AF312027 (Aug. 24, 2001).
GenBank Accession No. AY747068 (Mar. 1, 2005).
Ritte et al. (2000) "Compartmentation of the Starch-Related R1 Protein in Higher Plants." *Starch/Stärke* 52: 179-185.
Sitohy et al. (2000) "Optimizing the Conditions for Starch Dry Phosphorylation with Sodium Mono-and Dihydrogen Orthophosphate under Heat and Vacuum."*Starch/Stäke* 52(4): 95-100.
UniProtKB/Swiss-Prot entry Q6ZY51 (Jun. 13, 2006).
UniProtKB/TrEMBL entry Q84T18; Sucrose Synthase; Jun. 1, 2003; XP002361889.

(Continued)

*Primary Examiner* — Brent T Page
(74) *Attorney, Agent, or Firm* — Hunton & Williams, LLP

(57) ABSTRACT

The present invention relates to a method for identifying proteins involved in the phosphorylation of starch and nucleic acids which code for such proteins. The present invention further relates to plant cells and plants which exhibit an altered activity of a protein which can be identified using the method according to the invention. Plant cells and plants of this type synthesise a modified starch. The present invention therefore also relates to the starch synthesised by the plant cells and plants according to the invention as well as to methods for the manufacture of this starch and to the manufacture of starch derivatives of this modified starch.

14 Claims, 6 Drawing Sheets

OTHER PUBLICATIONS

Yu et. al. (Aug. 2001) "The *Arabidopsis* sex1 Mutant is Defective in the R1 Protein, a General Regulator of Starch Degradation in Plants, and Not in the Chloroplast Hexose Transporter." *The Plant Cell* 13: 1907-1918.

Baunsgaard, et al., "A novel isoform of glucan, water dikinase phosphorylates pre-phosphorylated α-glucans and is involved in starch degradation in *Arabidopsis*", The Plant Journal, vol. 41, p. 595-605, 2005.

Mikkelsen, et al., "Functional characterization of α-glucan, water dikinase, the starch phosphorylating enzyme", Biochem. J., vol. 377, p. 525-532, 2004.

NCBI Database Accession No. NP_198009.2.

EBI Accession No. EMBL: AK072331.

"TC77219", The DFCI Sorghum Bicolor Gene Index, Mar. 4, 2004, p. 1-2, retrieved from the internet at http://compbio.dfci.harvard.edu/tgi/cgi-bin/tgi/tc_report.pl, retrieved from the internet on Aug. 2, 2007.

TC117610, The DFCI Hordeum Vulgare Gene Index, Mar. 4, 2004, p. 1-2, retrieved from the internet at http://compbio.dfci.harvard.edu/tgi/cgi-bin/tgi/tc_report.pl, retrieved from the internet on Aug. 2, 2007.

EBI Accession No. EMBL: BF054632.

EBI Accession No. EMBL: CA741319.

* cited by examiner

METHODS FOR IDENTIFYING PROTEINS WITH STARCH PHOSPHORYLATING ENZYMATIC ACTIVITY

This application is a 371 National Stage filing of PCT/EP2005/002454 filed Mar. 4, 2005, which claims priority to EP 04090087.0, filed Mar. 5, 2004, and claims priority to EP 04090121.7, filed Mar. 29, 2004, and claims priority to EP 04090483.1, filed Dec. 9, 2004, and claims priority to U.S. Provisional Patent Application Ser. No. 60/549,980, filed Mar. 5, 2004, the disclosures all of which is hereby incorporated by reference.

The present invention relates to a method for identifying proteins involved in the phosphorylation of starch, and nucleic acids which code for such proteins. The invention further relates to plant cells and plants which exhibit an elevated activity of a protein identifiable using the method according to the invention. Plant cells and plants of this type synthesise a modified starch. The present invention therefore also relates to the starch synthesised by the plant cells and plants according to the invention as well as to methods for the manufacture of this starch and to the manufacture of starch derivatives of this modified starch.

With regard to the increasing importance currently attributed to plant constituents as renewable raw material sources, one of the tasks of biotechnological research is to endeavour to adapt these plant raw materials to suit the requirements of the processing industry. Furthermore, in order to enable regenerating raw materials to be used in as many areas of application as possible, it is necessary to achieve a large variety of materials.

Polysaccharide starch is made up of chemically uniform base components, glucose molecules, but constitutes a complex mixture of different molecule forms, which exhibit differences with regard to the degree of polymerisation and branching, and therefore differ strongly from one another in their physical-chemical characteristics.

Discrimination is made between amylose starch, an essentially unbranched polymer made from alpha-1,4-glycosidically linked glucose units, and amylopectin starch, a branched polymer, in which the branches come about by the occurrence of additional alpha-1,6-glycosidic links. A further essential difference between amylose and amylopectin lies in the molecular weight. While amylose, depending on the origin of the starch, has a molecular weight of $5\times10^5$-$10^6$ Da, that of the amylopectin lies between $10^7$ and $10^8$ Da. The two macromolecules can be differentiated by their molecular weight and their different physical-chemical characteristics, which can most easily be made visible by their different iodine bonding characteristics.

Amylose has long been regarded as a linear polymer, consisting of alpha-1,4-glycosidically linked alpha-D-glucose monomers. In more recent studies, however, the presence of alpha-1,6-glycosidic branching points (ca. 0.1%) has been shown (Hizukuri and Takagi, Carbohydr. Res. 134, (1984), 1-10; Takeda et al., Carbohydr. Res. 132, (1984), 83-92).

The functional properties such as, for example, the solubility, retrogradation behaviour, water binding capacity, film-forming properties, viscosity, gelatinisation properties, freeze-thaw stability, acid stability, gel strength and the starch granule size of starches are influenced among other things by the amylose/amylopectin ratio, molecular weight, side-chain distribution pattern, ion content, lipid and protein content, average starch granule size, starch granule morphology etc. The functional properties of starch are also influenced by the phosphate content, a non-carbon component of starch. Here, differentiation is made between phosphate, which is bound covalently in the form of monoesters to the glucose molecules of the starch (described in the following as starch phosphate), and phosphate in the form of phospholipids associated with the starch. In addition to the phosphate content, the influence on the functional properties of the starch is in this case also dependent on the form (starch phosphate or phospholipid) in which the phosphate occurs in the starch (Jane et al., 1996, Cereal Foods World 41 (11), 827-832).

The starch phosphate content varies according to the species of plant. Therefore, certain maize mutants, for example, synthesise a starch with increased starch phosphate content (waxy maize 0.002% and high-amylose maize 0.013%), while conventional types of maize only have traces of starch phosphate. Likewise small quantities of starch phosphate are found in wheat (0.001%) whereas no starch phosphate could be detected in oats and sorghum. In rice mutants likewise, less starch phosphate was found (waxy rice 0.003%) than in conventional species of rice (0.013%). Significant quantities of starch phosphate were detected in tuber- or root-storing starch synthesising plants such as, for example, tapioca (0.008%), sweet potato (0.011%), arrowroot (0.021%) or potato (0.89%). The percentage values for the starch phosphate content quoted above refer to the dry weight of starch in each case, and have been determined by Jane et al. (1996, Cereal Foods World 41 (11), 827-832).

Starch phosphate can be present in the form of monoesters at the C-2, C-3 or C-6 position of the polymerised glucose monomers (Takeda and Hizukuri, 1971, Starch/Stärke 23, 267-272). The phosphate distribution of the starch phosphate in starch synthesised by plants is generally distinguished by the fact that about 30% to 40% of the phosphate residues are covalently bound in the C-3 position and about 60% to 70% of the phosphate residue is covalently bound in the C-6 position of the glucose molecule (Blennow et al., 2000, Int. J. of Biological Macromolecules 27, 211-218). Blennow et al. (2000, Carbohydrate Polymers 41, 163-174) have determined a starch phosphate content which is bound in the C-6 position of the glucose molecule for various starches, such as for example, potato starch (between 7.8 and 33.5 nMol per mg of starch, depending on the type), starch from various *Curcuma* species (between 1.8 and 63 nMol per mg), tapioca starch (2.5 nMol per mg of starch), rice starch (1.0 nMol per mg of starch), mung bean starch (3.5 nMol per mg of starch) and sorghum starch (0.9 nMol per mg of starch). These authors have been unable to show any starch phosphate bound at the C-6 position in barley starch and starches from different waxy mutants of maize. Up to now, it has not been possible to establish a connection between the genotype of a plant and the starch phosphate content (Jane et al., 1996, Cereal Foods World 41 (11), 827-832). Thus, at the present time it is not possible to influence the content of starch phosphate in plants by means of breeding.

In transgenic plants the quantity of starch phosphate in storage starches can be varied. Thus, storage starch from potato plants which exhibit a reduced activity of soluble starch synthase III (Abel et al., 1996, The Plant Journal 10(6), 9891-991), branching enzyme I (BEI) (Safford et al., 1998, Carbohydrate Polymers 35, 155-168), branching enzyme II (BEII) (Jobling et al., 1999, The Plant Journal 18, 163-171), BEI and BEII (Schwall et al., 2000, Nature Biotechnology 18, 551-554), a disproportionation enzyme (WO 96 27673) or a disproportionation enzyme and a BEI (WO 95 07355), show an elevated content of starch phosphate compared with starch from corresponding wild type plants. However, the alteration in the starch phosphate content in these plants is not due to the proteins whose activity is reduced in these plants, being directly involved in the introduction of phosphate residues into the starch. The increase in the content of starch phosphate in the transgenic plants concerned is thus not a primary but a secondary effect which is brought about by reduction of the corresponding proteins. The reason for the increase in the content of starch phosphate as a result of modification of said protein activities is as yet still unexplained. Thus, it is not possible to specifically modify the content of starch phosphate by modifying protein activities which only influence the starch phosphate content by a secondary effect. Furthermore, modifying the activities of proteins which as a secondary effect have an influence on the content of starch phosphate in plants, at the same time also brings about further modifications in the starch, such as, for example: changes in the amylose/amylopectin ratio and/or the length of the side chains of the amylopectin which constitutes the primary effect of the changes in such protein activities.

Previously, only one protein has been described, which mediates the introduction of covalent bonds of phosphate residues to the glucose molecules of starch. This protein, frequently designated as R1 in the scientific literature, is bound to the starch granules of the storage starch in potato tubers (Lorberth et al., 1998, Nature Biotechnology 16, 473-477) and has the enzymatic activity of an alpha-glucan water dikinase (E.C. 02.07.09.4). In the reaction catalysed by R1 the educts alpha-1,4-glucan (starch), adenosinetriphosphate (ATP) and water are converted to the products glucan phosphate (phosphorylated starch), monophosphate and adenosine monophosphate. In this case, the gamma phosphate residue of the ATP is transferred to water and the beta phosphate residue of the ATP is transferred to the glucan (starch). R1 transfers in vitro the beta phosphate residue of the ATP to the C-6 and the C-3 position of the glucose molecules of alpha-1,4-glucans. The ratio of C-6 phosphate to C-3 phosphate which is obtained in the in vitro reaction corresponds to the ratio which is present in starch isolated from plants (Ritte et al., 2002, PNAS 99, 7166-7171). As about 70% of the starch phosphate present in potato starch is bound to the glucose monomers of the starch in the C-6 position and about 30% in the C-3 position, this means that R1 preferably phosphorylates the C-6 position of the glucose molecules. Furthermore, it has been shown by using amylopection from maize that, amongst other things, R1 can phosphorylate alpha-1,4-glucans which do not yet contain covalently bound phosphate (Ritte et al., 2002, PNAS 99, 7166-7171), i.e., R1 is able to introduce phosphate de novo into alpha-1,4-glucans.

The amino acid sequence of R1 contains a domain which exhibits a high degree of homology to known pyruvate phosphate dikinases (PPDK domains) and known pyruvate water dikinases (PPS domains) and contains a histidine residue conserved in PPDK and PPS domains. During the transfer of phosphate residues of the ATP to alpha-1,4-glucans (starch) a phosphorylated R1 protein is formed as intermediate product, with a phosphate residue being present, covalently bound to the histidine residue conserved in the PPDK or the PPS domain (Mikkelsen et al., 2004, Biochemical Journal 377, 525-532).

Nucleic acid sequences and amino acid sequences corresponding to these, coding for an R1 protein, are described from various species, such as for example, potato (WO 97 11188, GenBank Acc.: AY027522, Y09533), wheat (WO 00 77229, U.S. Pat. No. 6,462,256, GenBank Acc.: AAN93923, GenBank Acc.: AR236165), rice (GenBank Acc.: MR61445, GenBank Acc.: AR400814), maize (GenBank Acc.: MR61444, GenBank Acc.: AR400813), soya bean (GenBank Acc.: MR61446, GenBank Acc.: AR400815), citrus (GenBank Acc.: AY094062) and *Arabidopsis* (GenBank Acc.: AF312027).

Wheat plants which exhibit an elevated activity of an R1 protein as a result of overexpression of an R1 gene from potato are described in WO 02 34923. Compared with the corresponding wild type plants, in which no starch phosphate could be detected, these plants synthesise a starch having significant quantities of starch phosphate in the C-6 position of the glucose molecules.

Further proteins which catalyse a reaction which introduces covalently bound phosphate groups into the starch have not so far been described. Enzymes, which preferably introduce phosphate groups in the C-3 position and/or the C-2 position of the glucose molecules of starch, are also not known. Thus, apart from increasing the content of starch phosphate in plants, there are no available ways for specifically influencing the phosphorylation of starch in plants, modifying the phosphate distribution within the starch synthesised by plants and/or further increasing the content of starch phosphate.

It is thus the object of the present invention to provide methods and means for producing plants synthesising a modified starch having elevated phosphate content and/or modified phosphate distribution. as well as to provide plant cells and/or plants which synthesise such a modified starch.

This problem is solved by the embodiments described in the claims.

Thus, the present invention relates to a method for identifying a protein which has an elevated binding activity towards phosphorylated alpha-1,4 glucans, compared to non-phosphorylated alpha-1,4 glucans, wherein
a) protein extracts in preparations separated from one another are incubated with
   i phosphorylated alpha-1,4 glucans and
   ii non-phosphorylated alpha-1,4 glucans,
b) proteins specifically bound to the
   i phosphorylated alpha-1,4 glucans from step a) i and
   ii proteins specifically bound to the non-phosphorylated alpha-1,4 glucans from step a) ii
      are dissolved in preparations separate from one another and
c) proteins are identified which exhibit an elevated binding activity towards phosphorylated alpha-1,4 glucans used in step b) i, compared to non-phosphorylated alpha-1,4 glucans used in step b) ii.

In a further embodiment of the method according to the invention for identifying a protein which exhibits an elevated binding activity towards P-alpha-1,4-glucans compared to non-phosphorylated alpha-1,4 glucans, the alpha-1,4 glucan to which a higher binding activity exists is a starch, preferably a granular starch.

A further embodiment of the method according to the invention for identifying a protein which exhibits an elevated binding activity towards P-alpha-1,4-glucans compared to non-phosphorylated alpha-1,4 glucans, relates to a method for identifying a protein which has a molecular weight derived from the amino acid sequence of 120 kDa to 145 kDa, preferably 120 kDa to 140 kDa, particularly preferably 125 kDa to 140 kDa, especially preferably 130 kDa to 135 kDa.

In a further embodiment, the method according to the invention relates to a method for identifying a protein which exhibits an elevated binding activity towards P-alpha-1,4-glucans compared to non-phosphorylated alpha-1,4 glucans, wherein the binding activity to P-alpha-1,4-glucans is increased at least three times, preferably at least four times, particularly preferably at least five times and especially preferably at least six times compared to the binding activity to non-phosphorylated alpha-1,4-glucans.

The quantity of proteins which bind to P-alpha-1,4-glucans or non-phosphorylated alpha-1,4-glucans can, for example, be determined by immunological methods such as Western Blot Analysis, ELISA (Enzyme Linked Immuno Sorbent Assay) or RIA (Radio ImmunoAssay).

Methods for manufacturing antibodies, which react specifically with a certain protein, i.e. which bind specifically to said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered by some companies (e.g. Eurogentec, Belgium) as a contract service. One possible way for manufacturing antibodies which react specifically with a protein according to the invention is described below (see Example 11).

By comparing the dissolved P-alpha-1,4 glucan-binding proteins obtained by implementing the method according to the invention for identifying a protein which has an elevated binding activity towards P-alpha-1,4-glucans compared to non-phosphorylated alpha-1,4-glucans, with the dissolved non-phosphorylated alpha-1,4-glucan-binding proteins, which are obtained, it is possible to identify proteins which have an elevated binding activity towards P-alpha-1,4 glucans compared to non-phosphorylated alpha-1,4 glucans.

In a further embodiment of the method according to the invention for identifying a protein which exhibits an elevated binding activity towards phosphorylated alpha-1,4-glucans compared to non-phosphorylated alpha-1,4 glucans, the P-alpha-1,4-glucan protein complexes obtained by incubating protein extracts with P-alpha-1,4-glucans according to step a) i and the non-phosphorylated alpha-1,4-glucan protein complexes obtained by incubating protein extracts with non-phosphorylated alpha-1,4-glucans according to step a) ii are separated from the proteins not bound to the relevant alpha-1,4-glucans. In this case, the separation takes place separately for the respective incubation solutions after process step a) i or after process step a) ii.

In a further embodiment of the method according to the invention for identifying a protein which exhibits an elevated binding activity towards phosphorylated alpha-1,4-glucans compared to non-phosphorylated alpha-1,4 glucans, the proteins dissolved according to step b) i or b) ii are separated from the alpha-1,4 glucans used in the method according to the invention according to step a) i or step a) ii.

In the method according to the invention for identifying a protein which exhibits an elevated binding activity towards phosphorylated alpha-1,4-glucans compared to non-phosphorylated alpha-1,4 glucans, the dissolved proteins obtained according to process step b) i can either comprise a single protein or a plurality of proteins. The proteins dissolved according to process step b) ii can also either comprise a single protein or a plurality of proteins. Should the dissolved P-alpha-1,4-glucan-binding proteins or the dissolved non-phosphorylated alpha-1,4 glucan-binding proteins respectively comprise a plurality of different proteins, these are separated from one another if necessary.

In a further embodiment of the method according to the invention for identifying a protein which exhibits an elevated binding activity towards phosphorylated alpha-1,4-glucans compared to non-phosphorylated alpha-1,4-glucans, the P-alpha-1,4-glucan-binding proteins dissolved according to process step b) i or the non-phosphorylated alpha-1,4-glucan-binding proteins dissolved according to process step b) ii are separated from one another when implementing the method according to the invention.

The dissolved P-alpha-1,4-glucan-binding proteins or the dissolved non-phosphorylated alpha-1,4 glucan-binding proteins can be separated using methods known to the person skilled in the art such as, for example, gel filtration, chromatographic methods, electrophoresis etc. The P-alpha-1,4-glucan-binding dissolved proteins or the non-phosphorylated alpha-1,4 glucan-binding dissolved proteins are preferably separated from one another by means of SDS acrylamide gel electrophoresis, particularly preferably using the method described further below (see General Methods, Item 9).

A further object of the present invention is a method for identifying a protein which exhibits alpha-1,4-glucan phosphorylating enzymatic activity and requires phosphorylated alpha-1,4-glucans as substrate, wherein
a) protein extracts are incubated with phosphorylated alpha-1,4-glucans,
b) proteins specifically bound to the phosphorylated alpha-1,4-glucans from step a) are dissolved,
c) proteins obtained according to step b) are respectively incubated with
   i) ATP and phosphorylated alpha-1,4-glucans and
   ii) ATP and non-phosphorylated alpha-1,4-glucans
      in preparations separated from one another,
d) the respective alpha-1,4-glucan obtained after incubation in step c) i or step c) ii is examined for introduction of further phosphate groups and
e) proteins are identified which in the incubation preparation according to c) i have introduced significant quantities of phosphate groups into alpha-1,4-glucans and in the incubation preparation according to c) ii have introduced no significant quantities of phosphate groups into alpha-1,4-glucans.

The term "elevated binding activity" should be understood in conjunction with the present invention as an increased affinity of a protein to a first substrate compared to a second substrate, i.e. that the quantity of protein which under the same incubation conditions binds increasedly to a first substrate compared to a second substrate, exhibits an elevated binding activity to the first substrate.

The term "alpha-1,4-glucan" should be understood in conjunction with the present invention as a glucan which mainly consists of alpha-1,4-linked glucose building blocks but can also contain alpha-1,6-links as branches. An alpha-1,4-glucan preferably contains up to 15%, particularly preferably up to 10% and especially preferably up to 5% of alpha-1,6-links.

The term "starch phosphate" should be understood in conjunction with the present invention as phosphate groups covalently bound to the glucose molecules of an alpha-1,4-glucan.

The term "non-phosphorylated alpha-1,4-glucan" should be understood in conjunction with the present invention as an alpha-1,4-glucan which contains no detectable quantities of starch phosphate.

The term "phosphorylated alpha-1,4-glucan" or "P-alpha-1,4-glucan" should be understood in conjunction with the present invention as an alpha-1,4-glucan which contains starch phosphate.

Basically, a protein identifiable using a method according to the invention can come from any organism. The protein preferably comes from plant organisms, preferably from starch-storing plants (maize, rice, wheat, rye, oats, barley, cassava, potato, sweet potato, sago, mung bean, banana, pea, *Arabidopsis, Curcuma* or sorghum), particularly preferably from potato, barley, sugar beet, *Arabidopsis* or rice plants and especially preferably *Arabidopsis* or rice plants.

In a further embodiment of the method according to the invention, the protein extracts come from eukaryotic cells, preferably from plant cells, particularly preferably from cells of starch-storing (maize, rice, wheat, rye, oats, barley, cassava, potato, sweet potato, sago, mung bean, banana, pea, *arabidopsis, curcuma* or sorghum) plants.

Basically all non-phosphorylated alpha-1,4-glucans are suitable for incubating protein extracts with non-phosphorylated alpha-1,4-glucans for implementing the method according to the invention. Preferably used is a non-phosphorylated plant starch, particularly preferably wheat starch and especially preferably granular leaf starch of the *Arabidopsis thaliana* mutant sex1-3 (Tien-Shin Yu et al., 2001, Plant Cell 13, 1907-1918).

Methods for isolating starch from plants, for example, are known to the person skilled in the art. All methods known to the person skilled in the art are basically suitable for isolating non-phosphorylated starch from appropriate plant species. Preferably, the method for isolating non-phosphorylated alpha-1,4-glucans described below is used (see General Methods Item 2)

Basically all alpha-1,4-glucans containing starch phosphate are suitable for incubating protein extracts with P-alpha-1,4-glucans for implementing the method according to the invention. Chemically phosphorylated starches can also be used in this case. Preferably used for incubation with protein extracts are plant P-alpha-1,4-glucans, particularly preferably a subsequently enzymatically phosphorylated plant starch, especially preferably a subsequently enzymatically phosphorylated plant granular starch which was isolated from a sex1-3 mutant of *Arabidopsis thaliana*.

A subsequent enzymatic phosphorylation of non-phosphorylated alpha-1,4-glucans can be carried out with any enzyme which transfers phosphate residues to non-phosphorylated alpha-1,4-glucans by introduction of covalent bonds. Preferably used for this purpose is an enzyme having the activity of a water glucan dikinase (R1 Protein, E.C.: 02.07.09.4) (Ritte et al., 2002, PNAS 99, 7166-7171; Mikkelsen et al., 2004, Biochemical Journal 377, 525-532). Preferably used for the subsequent enzymatic phosphorylation of non-phosphorylated alpha-1,4-glucans is a purified R1 protein, especially an R1 protein from potato produced by heterologous expression in *E. coli*.

Methods for purifying an R1 protein produced recombinantly by expression in *E. coli* are described in Ritte et al. (2002, PNAS 99, 7166-7171) and Mikkelsen et al. (2003, Biochemical Journal 377, 525-532).

When implementing the method according to the invention, P-alpha-1,4-glucan-protein complexes can be formed by incubation of protein extracts with P-alpha-1,4-glucans and/or non-phosphorylated alpha-1,4-glucans as a result of the binding of proteins to P-alpha-1,4-glucans and non-phosphorylated alpha-1,4-glucan-protein complexes can be formed as a result of the binding of proteins to non-phosphorylated alpha-1,4-glucans.

The proteins present in P-alpha-1,4-glucan-protein complexes or non-phosphorylated alpha-1,4-glucan-protein complexes when implementing the method according to the invention are dissolved, i.e., the binding of the proteins concerned to the respective alpha-1,4-glucans is broken. Dissolved P-alpha-1,4-glucan-binding proteins and/or dissolved non-phosphorylated alpha-1,4-glucan-binding proteins are thus obtained. Basically, all substances which prevent the existing protein-alpha-1,4-glucan interaction can be used to break the binding between the alpha-1,4-glucans concerned and the proteins bound to them. Preferred for this purpose are buffer solutions containing detergents, particularly preferably buffer solutions containing sodium lauryl sulphate (SDS), especially preferably the buffer solution described further below (see General Methods Item 8).

Any method which allows alpha-1,4-glucans to be separated from the dissolved substances, such as proteins and, for example, ATP of the incubation preparation, can be used to separate alpha-1,4-glucans from ATP and/or proteins. If soluble alpha-1,4-glucans are used for the incubation of protein extracts with alpha-1,4-glucans when implementing the method according to the invention, the separation can, for example, involve a precipitation of the alpha-1,4-glucans, preferably a precipitation with suitable solvents, particularly preferably a precipitation with alcohols. The separation of alpha-1,4-glucans by binding to substances which selectively bind alpha-1,4-glucans (e.g. Concavalin A) is also suitable for separating alpha-1,4-glucans from substances in solution.

Preferably used here for the separation of alpha-1,4-glucans is filtration, particularly preferably centrifugation, especially preferably the method described further below (see General Methods Item 8).

When implementing the method according to the invention, all methods known to the person skilled in the art, such as chromatographic methods, for example, precipitation and subsequent centrifugation of the alpha-1,4-glucan, enzymatic digestion of the alpha-1,4-glucans, gel filtration etc. which lead to separation of soluble proteins from alpha-1,4-glucans, can basically be used to separate soluble proteins from the alpha-1,4-glucans. The dissolved P-alpha-1,4-glucan-binding proteins and/or dissolved non-phosphorylated alpha-1,4-glucan-binding proteins are preferably separated from the alpha-1,4-glucans used in the method according to the invention with the aid of centrifugation.

In a further embodiment of the present invention when implementing the method according to the invention, centrifugation using a Percoll pad is used to separate P-alpha-1,4-glucan-protein complexes from proteins not contained in the complexes concerned.

The method described further below (see General Methods Item 8) is preferably used here to separate the proteins not bound to the alpha-1,4-glucans. After centrifugation has been carried out using a Percoll pad, the proteins not bound to P-alpha-1,4-glucans or not bound to non-phosphorylated alpha-1,4-glucans are located in the supernatant of the centrifugation medium whereas the P-alpha-1,4-glucan-protein complexes or non-phosphorylated alpha-1,4-glucan-protein complexes are present in the sedimented pellet. The supernatant of the centrifugation medium is discarded and the pellet is preferably washed with the buffer used for the incubation for further purification of the P-alpha-1,4-glucan-protein complexes or non-phosphorylated alpha-1,4-glucan-protein complexes. The pellet is preferably washed once, particularly preferably twice.

Basically any type of protein extract can be used to carry out the method according to the invention for identifying a protein which exhibits an alpha-1,4-glucan phosphorylating enzymatic activity and requires phosphorylated alpha-1,4-glucans as substrate. Both so-called protein raw extracts and partly or completely purified protein extracts can be involved here. Thus, for example, it is advantageous to use proteins which were identified using a method according to the invention for identifying a protein which exhibits an elevated binding activity towards phosphorylated alpha-1,4-glucans compared to non-phosphorylated alpha-1,4-glucans. Proteins which were identified using a method according to the invention for identifying a protein which exhibits an elevated binding activity towards phosphorylated alpha-1,4-glucans compared to non-phosphorylated alpha-1,4-glucans, can, for example, be used omitting process steps a) and b) directly in step c) of the method according to the invention for identifying a protein which exhibits alpha-1,4-glucan phosphorylating enzymatic activity and requires phosphorylated alpha-1,4-glucans as substrate.

Basically, all general methods known to the person skilled in the art, such as described, for example, in Scopes (1993, Protein Purification: Principles & Practice, ISSN: 038794072) are suitable for producing protein extracts from prokaryotic or eukaryotic cells for implementing the method according to the invention. Preferably used for implementing the method, however, are methods for the isolation of plant proteins (e.g. described in Bollag et al, 1996, in: "Protein Methods", 2nd Edition, Wiley, ISBN: 0-471-11837-0; Dennison, 2003, in: "A Guide to Protein Isolation" 2nd Edition, Kluwer Academic Publishers, ISBN 1-4020-1224-1), particularly preferably the method described further below (see General Methods Item 1).

The incubation of protein extracts for implementing the method according to the invention with P-alpha-1,4-glucans or non-phosphorylated alpha-1,4-glucans takes place in separate preparations. The relevant preparations for P-alpha-1,4-glucans or non-phosphorylated alpha-1,4-glucans are treated separately from one another during the implementation of the entire method. In this case, respectively the same quantities of protein extract are to be incubated with respectively the same quantities of P-alpha-1,4-glucans or non-phosphorylated alpha-1,4-glucans. Preferably, respectively 1 to 10 mg, particularly preferably 3 to 7 mg and especially preferably 4 to 6 mg of protein extract are incubated with P-alpha-1,4-glucans or non-phosphorylated alpha-1,4-glucans. The quantity of P-alpha-1,4-glucans or non-phosphorylated alpha-1,4-glucans used is preferably respectively 10 to 100 mg, particularly preferably 30 to 70 mg and especially preferably 45 to 55 mg.

Various buffers can be used for the incubation of protein extracts with P-alpha-1,4-glucans for implementing the method according to the invention. Basically all buffers which allow binding of the proteins to be identified to the substrate concerned are suitable. The buffer described further below (see General Methods Item 1) is preferably used.

The term "protein which exhibits an alpha-1,4-glucan phosphorylating enzymatic activity and requires phosphorylated alpha-1,4-glucans as substrate" should be understood in conjunction with the present invention as a protein which introduces phosphate residues covalently into P-alpha-1,4-glucans, that is uses P-alpha-1,4-glucans as a substrate for the transfer of phosphate residues Whereas non-phosphorylated P-alpha-1,4-glucans are not phosphorylated by a protein concerned, i.e., non-phosphorylated P-alpha-1,4-glucans do not serve as a substrate for a phosphorylation reaction.

In a further embodiment the method according to the invention for identifying a protein which exhibits an alpha-1,4-glucan phosphorylating enzymatic activity and requires phosphorylated alpha-1,4-glucans as substrate relates to a method for identifying a protein which uses ATP as a further substrate.

In this embodiment of the present invention, ATP is used as a further substrate (co-substrate) by the protein which exhibits an alpha-1,4-glucan phosphorylating enzymatic activity and requires phosphorylated alpha-1,4-glucans as substrate, i.e. the protein concerned transfers a phosphate residue from ATP to an already phosphorylated P-alpha-1,4-glucan.

The activity of a protein which uses ATP as co-substrate for the transfer of phosphate residues to P-alpha-1,4-glucans can be demonstrated, i.e. by using ATP which contains a labeled phosphate residue (labeled ATP). To be preferred is ATP in which the phosphate residue is specifically labeled in the beta-position, i.e., in which only the phosphate residue in the beta-position has a marking. Preferably radioactively labeled ATP, particularly preferably ATP, in which the phosphate residue is specifically radioactively labeled in the beta position, and especially preferably ATP, in which the phosphate residue is specifically labeled with $^{33}P$ in the beta position, is used. If a P-alpha-glucan phosphorylating protein is incubated with P-alpha-1,4-glucans in the presence of labeled ATP, labeled phosphate covalently bound to the P-alpha-1,4-glucan can then be detected. In this case, the P-alpha glucans used for the phosphorylation reaction can be present both in the form of starch-phosphate-containing plant starch (potato starch, starch from *Curcuma armada, C. zedoaria, C. longa*, rice, mung beans, tapioca etc) and also in the form of enzymatically phosphorylated P-alpha-1,4-glucans or chemically phosphorylated P-alpha-1,4-glucans. Preferably starch from leaves of *Arabidopsis thaliana*, particularly preferably starch from *Arabidopsis thaliana* sex1-3 mutants enzymatically phosphorylated by means of an R1 protein is used.

Labeled phosphate residues which can be incorporated into a P-alpha-1,4-glucan by a protein, e.g., after separation of the labeled P-alpha-1,4-glucan (e.g., by precipitation of the alpha-1,4-glucans by means of ethanol, filtration, chromatographic methods, centrifugation etc.) from the remainder of the reaction mixture and subsequent detection of the labeled phosphate residues in the relevant P-alpha-1,4-glucan fraction, can be demonstrated. At the same time, the labeled phosphate residues bound in the P-alpha-1,4-glucan fraction can be demonstrated, for example, by determining the amount of radioactivity present in the P-alpha-1,4-glucan fraction (e.g. by means of scintillation counters).

In a further embodiment, the method according to the invention for identifying a protein which exhibits an alpha-1,4-glucan phosphorylating enzymatic activity and requires phosphorylated alpha-1,4-glucans as substrate relates to a method wherein the protein having alpha-1,4-glucan phosphorylating enzymatic activity uses P-starch as substrate. Starch isolated from a sex1-3 mutant of *Arabidopsis thaliana*, which was subsequently enzymatically phosphorylated is particularly preferred. For implementing this preferred embodiment of the method according to the invention, a phosphorylated starch is accordingly used in the process steps c) i and a non-phosphorylated starch is used in process step c) ii.

It is thereby possible to identify proteins which phosphorylate P-starch. Such proteins are especially suitable for modifying starch in plant organisms by means of genetic manipulation of appropriate plants.

In a further embodiment the method according to the invention for identifying a protein which exhibits an alpha-1,4-glucan phosphorylating enzymatic activity and requires phosphorylated alpha-1,4-glucans as substrate relates to a method for identifying a protein wherein the protein occurs as a phosphorylated intermediate product during the transfer of a phosphate residue to a P-alpha-1,4-glucan. Said intermediate product is preferably formed by autophosphorylation of the protein concerned.

A phosphorylated protein which occurs as an intermediate product as a result of protein-mediated phosphorylation of P-alpha-1,4-glucans can be demonstrated as described in Ritte et al. (2002, PNAS 99, 7166-7171) for an R1 protein.

In order to detect the presence of an autophosphorylated intermediate product, a protein is first incubated in the absence of glucans with labeled ATP, preferably with ATP labeled specifically in the beta phosphate position, particularly preferably with ATP labeled specifically with $^{33}P$ in the beta phosphate position for 15 to 45 minutes, particularly preferably for 20 to 40 minutes and especially preferably for 25 to 30 minutes in a reaction preparation 1. Parallel to this, a reaction preparation 2 which contains corresponding quantities of non-labeled ATP instead of labeled ATP, is incubated under otherwise the same conditions. Non-labeled ATP is then added to reaction mixture 1 in excess and a mixture of non-labeled ATP and labeled ATP (the same quantity of labeled ATP as used previously in reaction mixture 1 and the same quantity of non-labeled ATP as added in excess to reaction mixture 1) is added to reaction mixture 2 and incubated for a further 1 minute to 5 minutes, preferably for 2 to 5 minutes and especially preferably for 3 minutes before P-alpha-1,4-glucans are added to a Part A of reaction mixture 1 (Part 1A) or to a Part A of reaction mixture 2 (Part 2A). The reaction in the remaining Part 1B and Part 2B of the reaction mixture is stopped by denaturing the protein. Part B of the reaction mixture can be stopped by the methods known to the person skilled in the art, which lead to the denaturing of proteins, preferably by adding sodium lauryl sulphate (SDS). Part 1A and Part 2A of the reaction mixtures are incubated for at least a further 10 minutes before these reactions are also stopped. The alpha-1,4-glucans present in Part A or Part B of the respective reaction mixtures are separated from the respective remainder of the reaction mixtures. If the respective alpha-1,4-glucans are separated by centrifugation, for example, then, on completion of centrifugation, the alpha-1,4-glucans of the respective Part A or Part B of the reaction mixture are to be found in the sedimented pellet, and the proteins in the respective reaction mixtures are to be found in the supernatant of the respective centrifugation. The supernatant of Part 1A or 2A and of Part 1B or 2B of the reaction mixture can then be analysed, for example, respectively in a denaturing acrylamide gel electrophoresis, followed by autoradiography of the acrylamide gel obtained. To quantify the amount of radioactively labeled proteins, which have been separated by means of acrylamide gel electrophoresis, the so-called "phospho-imaging" method, for example, known to the person skilled in the art, can be used. If the autoradiography or the analysis by means of the "phospho-imager" of proteins in the centrifugation supernatant of Part B of reaction mixture 1 shows a significantly increased signal compared with the centrifugation supernatant of Part A of reaction mixture 1, then this shows that a protein mediating a phosphorylation of alpha-glucans occurs as an autophosphorylated intermediate product. Parts A and B of reaction mixture 2 serve as a control and should therefore not exhibit a significantly increased signal in the centrifugation supernatant in the autoradiography or in the analysis by means of the "phospho-imager".

In addition, the alpha-1,4-glucans of the respective Part A of reaction mixtures 1 and 2 remaining in the respective sedimented pellet can be investigated, if necessary after subsequent washing of the respective alpha-1,4-glucans, for the presence of starch phosphate, which has a mark corresponding to the labeled ATP used. If the alpha-1,4-glucans of Part A of reaction mixture 1 contain labeled phosphate residues, and if the autoradiography of the centrifugation supernatant of Part B of reaction mixture 1 shows a significantly increased signal in the autoradiography compared with the centrifugation supernatant of Part A of reaction mixture 1, then this shows that a protein mediating a phosphorylation of alpha-glucans is present as an autophosphorylated intermediate product. Parts A and B of reaction mixture 2 serve as a control and should therefore not exhibit a significantly increased signal for alpha-1,4-glucans labeled with $^{33}P$ in the sedimented pellet containing alpha-1,4-glucans.

In a further embodiment the method according to the invention for identifying a protein which exhibits an alpha-1,4-glucan phosphorylating enzymatic activity and requires phosphorylated alpha-1,4-glucans as substrate relates to a method for identifying a protein which preferably introduces phosphate monoester bonds in the C-2 position or in the C-3 position, particularly preferably in the C-3 position of a glucose molecule of a P-alpha-1,4-glucan.

Which positions if the carbon atoms (C-2, C-3 or C-6) of the glucose monomers in the P-alpha-1,4-glucan are preferably phosphorylated by a protein or protein extract can be determined, for example, by analysing the P-alpha-1,4-glucans phosphorylated by a protein or protein extract, as described in Ritte et al. (2002, PNAS 99, 7166-7171). For this purpose P-alpha-1,4-glucans additionally phosphorylated by a protein or protein extract are hydrolysed using acid and then analysed by means of anion exchange chromatography.

The P-alpha-1,4-glucans phosphorylated by a protein are preferably analysed by means of NMR in order to determine which positions of the carbon atoms (C-2, C-3 or C-6) of the glucose monomers are phosphorylated in P-alpha-1,4-glucan.

Proteins of the method according to the invention for identifying a protein which exhibits an alpha-1,4-glucan phosphorylating enzymatic activity and requires phosphorylated alpha-1,4-glucans as substrate, which were obtained according to process step b) are incubated in step c) of the method according to the invention in separate preparations containing ATP and P-alpha-1,4-glucan or ATP and non-phosphorylated alpha-1,4-glucan. For implementing the method according to the invention it is preferable to use ATP which contains a labeled phosphate residue, particularly preferably a phosphate residue specifically labeled in the beta position, especially a phosphate residue specifically radioactively labeled in the beta position.

The incubation of dissolved proteins according to the invention with ATP and P-alpha-1,4-glucans according to process step c) i or non-phosphorylated alpha-1,4-glucans according to step c) ii of the method according to the invention for identifying a protein which exhibits an alpha-1,4-glucan phosphorylating enzymatic activity and requires phosphorylated alpha-1,4-glucans as substrate, preferably takes place at a temperature of 20° C. to 30° C., particularly preferably 23° C. to 27° C. and especially preferably 24° C. to 26° C. and is carried out for a duration of at least 15 minutes, preferably for at least 20 minutes, particularly preferably for at least 30 minutes. The quantity of ATPs used in this case is preferably at least 0.05 µM, particularly preferably at least 3 µM and especially preferably at least 5 µM. The concentration of the P-alpha-1,4-glucan used or the non-phosphorylated alpha-1,4-glucan used is in this case preferably at least 1 mg/ml, particularly preferably at least 10 mg/ml and especially preferably at least 25 mg/ml. After incubation has been completed, the reactions of protein extracts with P-alpha-1,4-glucans or non-phosphorylated alpha-1,4-glucans can be stopped. The respective reaction mixture can be stopped by methods known to the person skilled in the art which lead to denaturing of proteins, preferably by adding sodium lauryl sulphate and heating for 5 minutes at 95° C. When implementing step c) i or c ii) of the method according to the invention for identifying a protein which exhibits an alpha-1,4-glucan phosphorylating enzymatic activity and requires phosphorylated alpha-1,4-glucans as substrate, respectively the same incubation conditions for the respective incubation preparations should be carried out during the incubation of proteins with P-alpha-1,4-glucans or non-phosphorylated alpha-1,4-glucans.

The P-alpha-1,4-glucan obtained according to process step c) i or the non-phosphorylated alpha-1,4-glucan obtained according to process step c) ii after implementing the method according to the invention for identifying a protein which exhibits an alpha-1,4-glucan phosphorylating enzymatic activity and requires phosphorylated alpha-1,4-glucans as substrate, is investigated for the introduction of additional phosphate residues. In order to determine whether phosphate residues were additionally introduced into the alpha-1,4-glucans concerned by process steps c) i and/or c) ii, any method which is possible for the specific detection of the marking used for the labeled ATPs used in process steps c) i and c) ii can be used. If, for example, radioactively labeled ATP is used in process steps c) i or c) ii, this can be carried out using methods known to the person skilled in the art for the detection of radioactive elements, such as, for example, autoradiography, measurement of the radioactivity by means of suitable equipment (e.g. scintillation counters, "phosphoimagers" etc.).

Proteins used in process step b) of the method according to the invention for identifying a protein which exhibits alpha-1,4-glucan phosphorylating enzymatic activity and requires phosphorylated alpha-1,4-glucans as substrate, which have introduced significant quantities of phosphate residues into P-alpha-1,4-glucans in step c) i but in comparison thereto, have introduced no significant quantities of phosphate residues into non-phosphorylated alpha-1,4-glucans in step c) ii, can be identified by methods known to the person skilled in the art.

The term "significant quantities" should be understood in conjunction with the present invention as a quantity which is at least twice, preferably at least four times, particularly preferably at least six times and especially preferably at least eight times higher than the quantity determined in corresponding control experiments.

In this case, incubation preparations which contain completely inactivated protein extracts or no protein extracts instead of native protein extracts can be used as control experiments. Protein extracts in which no more alpha-1,4-glucan phosphorylating enzymatic activity can be detected are to be understood as "completely inactivated".

Identifying proteins when implementing the method according to the invention for identifying a protein which exhibits an elevated binding activity towards phosphorylated alpha-1,4-glucans compared to non-phosphorylated alpha-1,4-glucans can be made using methods known to the person skilled in the art such as, for example, determining the amino acid sequence of the proteins concerned using methods comprising Edmann degradation, mass analysis using MALDI-TOF-MS (Matrix Assisted Laser Desorption/Ionization-Time Of Flight-Mass Spectroscopy), followed by comparisons with data bases containing mass profiles of proteins, amino acid sequencing by means of Q-TOF analysis or TOF/TOF analysis etc. The proteins concerned are preferably identified by means of Q-TOF-MS-MS analysis, especially preferably the proteins are identified using the method described further below (see General Methods Item 10).

If proteins are determined by means of MALDI-TOF-MS, followed by comparisons with databases containing mass profiles of proteins, the proteins concerned are first enzymatically digested beforehand before the individual masses of the protein fragments (peptides) obtained from the digestion are analysed by means of MALDI-TOF-MS. A mass profile of the protein concerned is obtained. These mass profiles are very specific for a protein since sequence-specific proteases are used for the digestion of proteins which only cleave a peptide bond when it is contained in a specific amino acid sequence succession. If the special amino acid sequence which serves as a recognition sequence for a certain protease is known, a theoretical mass profile can be created from any arbitrary amino acid sequence by calculating the mass of the peptides which would be produced after digestion of the amino acid sequence with a specific protease. By comparing mass profiles of unknown proteins actually obtained using MALDI-TOF-MS with the theoretically determined mass profiles in corresponding databases, amino acid sequences can thus also be determined.

In a further embodiment the method according to the invention for identifying a protein which exhibits alpha-1,4-glucan phosphorylating enzymatic activity and requires phosphorylated alpha-1,4-glucans as substrate, the P-alpha-1,4-glucan-protein complexes obtained by incubating protein extracts with P-alpha-1,4-glucans according to step a) are separated from the proteins not bound to the alpha-1,4-glucans concerned.

In a further embodiment of the method according to the invention for identifying a protein which exhibits alpha-1,4-glucan phosphorylating enzymatic activity and requires phosphorylated alpha-1,4-glucans as substrate, the proteins dissolved according to step b) of the method according to the invention are separated from the P-alpha-1,4-glucans used in step a).

In a further embodiment the method according to the invention for identifying a protein which exhibits alpha-1,4-glucan phosphorylating enzymatic activity and requires phosphorylated alpha-1,4-glucans as substrate, the dissolved P-alpha-1,4-glucan-binding proteins, obtained when implementing the method according to the invention according to process step b), are separated from one another.

In a further embodiment of the method according to the invention for identifying a protein which exhibits alpha-1,4-glucan phosphorylating enzymatic activity and requires phosphorylated alpha-1,4-glucans as substrate, the glucans obtained by incubation of protein extracts with P-alpha-1,4-glucans according to step c) i or with non-phosphorylated alpha-1,4-glucans according to step c) ii are separated from the proteins present in the reaction mixture and/or the labeled ATP present in the reaction mixture.

Preferably used here for the separation of alpha-1,4-glucans is filtration, particularly preferably centrifugation, especially preferably the method described further below (see General Methods Item 8). After centrifugation has been carried out using a Percoll pad, soluble substances of the reaction mixtures are located in the supernatant of the centrifugation medium whereas the alpha-1,4-glucans are present in the sedimented pellet.

A further embodiment of the method according to the invention for identifying a protein which exhibits alpha-1,4-glucan phosphorylating enzymatic activity and requires phosphorylated alpha-1,4-glucans as substrate, relates to a method for identifying a protein which has a molecular weight derived from the amino acid sequence of 120 kDa to 145 kDa, preferably 120 kDa to 140 kDa, particularly preferably 125 kDa to 140 kDa, especially preferably 130 kDa to 135 kDa.

In a further embodiment of the method according to the invention for identifying a protein, after identification of the proteins concerned amino acid sequences which code for these proteins are determined.

The amino acid sequences can be determined according to the invention using any methods known to the person skilled in the art. Such methods are sufficiently described in the specialist literature (e.g. in Protein Sequencing and Identification Using Tandem Mass Spectrometry, 2000, John Wiley & Sons Inc, ISBN: 0-471-32249-0; Protein Sequencing Protocols, 2002, Smith (Ed.), Edition: $2^{nd}$, Humana Press, ISBN: 0-89603-975-7) and are basically suitable for implementing the method according to the invention. Also, the purification and/or sequencing of proteins is carried out as a contract service by many companies (e.g. Eurogentec, Searing, Belgium).

If necessary, proteins using a method according to the invention for identifying a protein can be subjected to further purification and/or concentration before determining their amino acid sequence. Methods for purification and/or concentration of proteins are sufficiently described in the specialist literature (e.g. in Methods in Enzymology: Guide to Protein Purification, Vol. 182 1990, Deutscher, Murray P. (Ed.), Academic Press, ISBN: 0-12-182083-1; Isolation and Purification of Proteins: Hatti-Kaul, 2003, Rajni (Ed.); Mattiasson, Bo (Edt), Marcel Dekker Inc, ISBN:0-8247-0726-5, Protein Purification Techniques: A Practical Approach. Roe, 2001, Simon (Ed.). The Practical Approach Series, 244. Edition: 2nd. Oxford Univ Press, ISBN: 0-19-963673-7) and are basically suitable for implementing the method according to the invention.

In a further embodiment of the method according to the invention for identifying a protein, methods according to the invention for identifying a protein whose encoding amino acid sequence has a phosphohistidine domain (Tien-Shin Yu et al., 2001, Plant Cell 13, 1907-1918) are used. The phosphohistidine domain preferably has an identity of at least 50% with the amino acid sequence of the phosphohistidine domain of the OK1 protein from *Arabidopsis thaliana* and *Oryza sativa* specified under SEQ ID NO 5, in particular of at least 60%, preferably of at least 70% and particularly preferably of at least 80% and especially preferably of at least 90%.

In a further embodiment of the method according to the invention for identifying a protein, methods according to the invention for identifying a protein whose encoding amino acid sequence has a phosphohistidine domain (Tien-Shin Yu et al., 2001, Plant Cell 13, 1907-1918) are used wherein the phosphohistidine domain contains two histidines.

Using the methods according to the invention, proteins which exhibit an elevated binding activity towards P-alpha-1,4-glucans compared to non-phosphorylated alpha-1,4-glucans can be identified.

Using the method according to the invention, proteins which exhibit alpha-1,4-glucan phosphorylating enzymatic activity and require phosphorylated alpha-1,4-glucans as substrate can be identified.

Thus, proteins obtainable by methods according to the invention for identifying a protein are also the object of the present invention.

A method for identifying a nucleic acid coding for a protein which exhibits alpha-1,4-glucan phosphorylating enzymatic activity is further an object of the present invention, wherein
a) a protein is identified using a method according to the invention for identifying a protein,
b) amino acid sequences coding for the protein identified according to step a) are determined and
c) nucleic acids are identified using the amino acids determined according to step b), which code for a protein identified according to step a).

The amino acid sequence of the proteins identified using a method according to the invention can be determined using methods known to the person skilled in the art, as already stated above.

On the basis of the amino acid sequences determined according to step b) of the method according to the invention for identifying a nucleic acid, coding for a protein which exhibits alpha-1,4-glucan-phosphorylating enzymatic activity, nucleic acids coding for a protein exhibiting alpha-1,4-glucan-phosphorylating enzymatic activity can be identified.

Nucleic acids coding for a protein exhibiting alpha-1,4-glucan-phosphorylating enzymatic activity can be identified, for example, by scrutinising databases such as those made available, for example by EMBL (www.ebi.ac.uk/Tools/index.htm) or NCBI (National Center for Biotechnology Information, www.ncbi.nlm.nih.gov/). In this case one or a plurality of amino acid sequences determined when implementing the method according to the invention, is pre-defined as a so-called query. This query sequence is then compared by means of statistical computer programs with sequences, which are contained in the selected databases. Such database queries (e.g. blast or fasta searches) are known to the person skilled in the art and can be carried out by various providers.

If such a database query is carried out, e.g. at the NCBI (National Center for Biotechnology Information, www.ncbi.nlm.nih.gov/), then the standard settings, which are specified for the particular comparison inquiry, should be used For protein sequence comparisons (blastp), these are the following settings: Limit entrez = not activated; Filter = low complexity activated; Expect value =10; word size =3; Matrix = BLOSUM62; Gap costs: Existence =11, Extension = 1.

During such a database search, for example, the amino acid sequences determined in the present invention when implementing the method according to the invention can be used as a query sequence in order to identify nucleic acid molecules coding for a protein which exhibits alpha-1,4-glucan phosphorylating enzymatic activity.

Using the method described, it is also possible to identify nucleic acid molecules and/or amino acid sequences which have a high degree of identity to nucleic acid molecules and/or proteins obtainable using the method according to the invention and coding for a protein which exhibits alpha-1,4-glucan phosphorylating enzymatic activity.

Methods are known to the person skilled in the art with which, starting from amino acid sequences, he can identify nucleic acids coding for these (see, for example, Sambrok et al., Molecular Cloning, A Laboratory Manual, 3rd edition (2001) Cold Spring Harbour Laboratory Press, Cold Spring Harbour, NY. ISBN: 0879695773, Ausubel et al., Short Protocols in Molecular Biology, John Wiley & Sons; 5th edition (2002), ISBN: 0471250929). From amino acid sequences coding for a protein which exhibits alpha-1,4-glucan phosphorylating enzymatic activity, nucleic acids coding for the amino acid sequences concerned can be derived in accordance with the genetic code. It is known to the person skilled in the art that the degenerated oligonucleotides obtained from the genetic code can basically also be used to identify nucleic acids. Oligonucleotides which constitute sequences derived from the amino acid sequences obtained when implementing the method according to the invention can then be synthesised. These synthetic oligonucleotides can be used to identify nucleic acids coding for the proteins from whose amino acid sequence the corresponding oligonucleotide sequences were derived. This can be achieved, for example, by searching gene libraries, said synthetic oligonucleotides being used as labeled probes in the form of hybridisation probes. A further possibility for identifying nucleic acids coding for a protein which exhibits alpha-1,4-glucan phosphorylating enzymatic activity involves using the synthetic oligonucleotides derived from amino acid sequences obtained when implementing the method according to the invention, by searching gene libraries using PCR based methods, wherein said synthetic oligonucleotides are used as so-called "primers". Gene libraries can be present, for example, in the form of cosmids, phagmids, plasmids, YACs or BACs. The DNA libraries can contain both genomic and also cDNA. For PCR-based searching methods when using the so-called RT (Reverse Transcription)

PCR, it is also possible to use mRNA The nucleic acids for the implementation of the method according to the invention for identifying a nucleic acid in gene libraries or present as mRNA can in this case come from any organism, preferably they come from eukaryotic, particularly preferably from plants, especially preferably from cereals.

For the implementation of the method according to the invention for identifying a nucleic acid coding for a protein which exhibits alpha-1,4-glucan-phosphorylating enzymatic activity, it is not necessary that the entire amino acid sequence coding for the protein concerned is determined in step b) of the method according to the invention but it can be sufficient if only parts of the amino acid sequences concerned, coding for a protein concerned, are determined.

A further embodiment of the present invention relates to a method for identifying a nucleic acid coding for a protein which exhibits alpha-1,4-glucan-phosphorylating enzymatic activity, wherein a) a protein is identified using a method according to the invention for identifying a protein,
b) amino acid sequences coding for the protein identified according to step a) are determined
c) oligonucleotides are synthesised starting from the amino acid sequences determined in step b) and
d) nucleic acids coding for a protein identified according to step a) are identified with the aid of the oligonucleotides synthesised according to step c)

A further object of the present invention relates to a method for identifying a nucleic acid coding for a protein which exhibits alpha-1,4-glucan-phosphorylating enzymatic activity, wherein a) a protein is identified using a method according to the invention for identifying a protein,
b) antibodies which react specifically with the protein identified according to step a) are produced and
c) nucleic acids are identified using the antibodies determined according to step b).

Methods for manufacturing antibodies, which react specifically with a certain protein, i.e. which bind specifically to said protein, are known to the person skilled in the art (see, for example, Lottspeich and Zorbas (Eds.), 1998, Bioanalytik, Spektrum akad, Verlag, Heidelberg, Berlin, ISBN 3-8274-0041-4). The manufacture of such antibodies is offered by some companies (e.g. Eurogentec, Belgium) as a contract service.

Methods for identifying nucleic acids using antibodies, frequently designated as "immunoscreening" in the specialist literature (see, for example Lottspeich und Zorbas (Eds.), 1998, Bioanalytik, Spektrum akad. Verlag., Heidelberg, Berlin, ISBN 3-8274-0041-4) are likewise known to the person skilled in the art and described in detail in the literature. So-called expression gene libraries, for example, can be used to implement such methods, in which the clones obtained are searched for the expression of a certain protein with the aid of a specific antibody directed against this protein. Materials for manufacturing such expression gene libraries, also containing instructions relating the method for the manufacture and also methods for searching such expression gene banks can be purchased (e.g. Stratagene).

Using methods according to the invention, it is possible to identify nucleic acids coding for proteins which exhibit elevated binding activity towards P-alpha-1,4-glucans compared to non-phosphorylated alpha-1,4-glucans and/or which exhibit alpha-1,4-glucan phosphorylating enzymatic activity and require phosphorylated alpha-1,4-glucans as substrate.

Thus, nucleic acids obtainable by methods according to the invention for identifying a nucleic acid, are also the object of the present invention.

A plasmid (A.t.-OK1-pGEM) containing a cDNA which codes for a protein according to the invention (A.t.-OK1) from *Arabidopsis thaliana* was deposited on 08.03.2004 under the number DSM16264 and a plasmid (pMI50) containing a cDNA which codes for further protein according to the invention (O.s.-OK1) from *Oryza sativa* was deposited on 24.03.2004 under the number DSM16302 under the Budapest Treaty at the German Collection of Microorganisms and Cell Cultures GmbH, Mascheroder Weg 1b, 38124 Braunschweig, Germany.

It was surprisingly found that genetically modified plant cells or plants which exhibit an elevated activity of a protein according to the invention, synthesise a modified starch which is modified in its physical-chemical properties, especially the content of starch phosphate or the phosphate distribution compared to starch synthesised in wild type plant cells or wild type plants so that this is better suited for special applications.

Thus, a further object of the present invention relates to genetically modified plant cells or genetically modified plants characterised in that they exhibit an elevated enzymatic activity of a protein according to the invention compared to corresponding non-genetically modified wild type plant cells or wild type plants.

In this case, the genetic modification can be any genetic modification, which leads to an increase in the activity of at least one protein according to the invention in comparison with corresponding wild type plant cells or wild type plants that have not been genetically modified.

In conjunction with the present invention, the term "wild type plant cell" means that the plant cells concerned were used as starting material for the manufacture of the plant cells according to the invention, i.e. their genetic information, apart from the introduced genetic modification, corresponds to that of a plant cell according to the invention.

In conjunction with the present invention, the term "wild type plant" means that the plants concerned were used as starting material for the manufacture of the plants according to the invention, i.e. their genetic information, apart from the introduced genetic modification, corresponds to that of a plant according to the invention.

In conjunction with the present invention, the term "corresponding" means that, in the comparison of several objects, the objects concerned that are compared with one another have been kept under the same conditions. In conjunction with the present invention, the term "corresponding" in conjunction with wild type plant cell or wild type plant means that the plant cells or plants, which are compared with one another, have been raised under the same cultivation conditions and that they have the same (cultivation) age.

The term "elevated activity" in the framework of the present invention means in this case an increase in the expression of endogenous genes coding for proteins according to the invention and/or an increase in the quantity of proteins according to the invention in the cells and/or an increase in the enzymatic activity of proteins according to the invention in the cells.

The increase in the expression can, for example, be determined by measuring the quantity of transcripts coding for proteins according to the invention, e.g. using Northern blot analysis or RT-PCR. Nucleic acid molecules which were identified using methods according to the invention for identifying a nucleic acid are preferably used in this case to determine an elevated expression of proteins according to the invention. Here, an increase preferably means an increase in the amount of transcripts in comparison with corresponding cells that have not been genetically modified by at least 50%, in particular by at least 70%, preferably by at least 85% and particularly preferably by at least 100%. An increase in the quantity of transcripts coding for a protein according to the invention also means that plants which have no detectable transcripts coding for a protein according to the invention, after genetic modification according to the invention, have a detectable quantity of transcripts coding for a protein according to the invention.

The increase in the amount of protein of a protein according to the invention, which results in an increased activity of this protein in the plant cells concerned, can, for example, be determined by immunological methods such as Western Blot analysis, ELISA (Enzyme Linked Immuno Sorbent Assay) or RIA (Radio ImmunoAssay). The manufacture of an antibody which can be used to measure the increase in the amount of protein using immunological methods is described further below as an example (see Example 11). Here, an increase preferably means an increase in the amount of a protein according to the invention in comparison with corresponding cells that have not been genetically modified by at least 50%, in particular by at least 70%, preferably by at least 85% and particularly preferably by at least 100%. An increase in the amount of a protein according to the invention also means that plants which have no detectable amount of a protein according to the invention, after genetic modification according to the invention, have a detectable amount of protein according to the invention.

It was surprisingly also found that genetically modified plant cells or plants which exhibit a reduced activity of a protein according to the invention, synthesise a modified starch which is modified in its physical-chemical properties, especially relating to the phosphate distribution compared to starch synthesised in wild type plant cells or wild type plants so that this is better suited for special applications.

Thus, a further object of the present invention relates to genetically modified plant cells or genetically modified plants, characterised in that they exhibit a reduced enzymatic activity of a protein according to the invention compared to corresponding wild type plant cells or wild type plants which have not been genetically modified.

Plants which exhibit a reduced activity of a protein according to the invention, exhibit a high starch (starch excess) phenotype. Furthermore, plants which exhibit a reduced activity of a protein according to the invention, exhibit normal growth compared to wild type plants, i.e., the plants are not hindered in their growth by the reduced activity of a protein according to the invention. Therefore, plants which exhibit a reduced activity of a protein according to the invention, are suitable for cultivation in agriculture since they contain more starch and therefore more carbohydrate and at the same time show no reduction in growth rate.

The present invention therefore also relates to plant cells and plants according to the invention which exhibit a starch excess phenotype. Plant cells according to the invention and plants according to the invention have at least twice, preferably at least four times, particularly preferably at least six times and especially preferably, at least eight times more starch in their leaves at the end of the dark phase than corresponding wild type plant cells or wild type plants.

Plant cells according to the invention and plants according to the invention have at least 1.2 times, preferably at least 1.5 times, particularly preferably at least 1.8 times and especially preferably at least twice more starch in their leaves at the end of the light phase than corresponding wild type plant cells or wild type plants.

The plant cells according to the invention and plants according to the invention which exhibit a reduced activity of a protein according to the invention, can be manufactured by various methods known to the person skilled in the art. These include, for example, the expression of a corresponding antisense RNA, or a double-stranded RNA construct, the preparation of molecules or vectors which impart a co-suppression effect, the expression of a correspondingly constructed ribozyme which specifically cleaves transcripts which code for a protein according to the invention or the so-called "in vivo mutagenesis". Moreover, the reduction of the activity of a protein according to the invention in plant cells and plants can also be brought about by the simultaneous expression of sense and antisense RNA molecules of the respective target gene to be repressed, preferably the OK1 gene.

It is additionally known that the in planta formation of double-stranded RNA molecules of promoter sequences in trans can lead to a methylation and a transcriptional inactivation of homologous copies of this promoter (Mette et al., EMBO J. 19, (2000), 5194-5201).

Another possible method for reducing the enzymatic activity of proteins in plant cells or plants is the so-called immunomodulation method. It is known that an in planta expression of antibodies which specifically recognise a plant protein results in a reduction in the activity of the relevant protein in corresponding plant cells as a result of the formation of a protein antibody complex (Conrad and Manteufel, Trends in Plant Science 6, (2001), 399-402; De Jaeger et al., Plant Molecular Biology 43, (2000), 419-428; Jobling et al., Nature Biotechnology 21, (2003), 77-80).

All these methods are based on the introduction of a foreign or a plurality of foreign nucleic acid molecules into the genome of plant cells or plants and are therefore fundamentally suitable for manufacturing plant cells according to the invention and plants according to the invention.

In a further embodiment of the present invention, the plant cells according to the invention or plants according to the invention comprise plant cells of starch-storing plants or starch-storing plants. Starch-storing plants are, for example, maize, rice, wheat, rye, oats, barley, cassava, potato, sweet potato, sago, mung bean, banana, pea, *Arabidopsis, curcuma* or sorghum plants. Particularly preferred are rice, especially preferred are wheat plants.

A further embodiment of the present invention relates to a genetically modified plant cell according to the invention or a genetically modified plant according to the invention, wherein the genetic modification consists in the introduction of at least one foreign nucleic acid molecule into the genome of the plant.

In this context, the term "genetic modification" means the introduction of homologous and/or heterologous foreign nucleic acid molecules into the genome of a plant cell or into the genome of a plant, wherein said introduction of these molecules leads to an increase or reduction in the activity of a protein according to the invention.

The plant cells according to the invention or plants according to the invention are modified with regard to their genetic information by the introduction of a foreign nucleic acid molecule. The presence or the expression of the foreign nucleic acid molecule leads to a phenotypic change. "Phenotypic" change preferably means in this case a measurable change in one or a plurality of functions of the cells. For example, the genetically modified plant cells according to the invention and the genetically modified plants according to the invention exhibit an increase or reduction in the activity of a protein according to the invention due to the presence or on the expression of the introduced nucleic acid molecule.

In conjunction with the present invention, the term "foreign nucleic acid molecule" is understood to mean such a molecule that either does not occur naturally in the corresponding wild type plant cells, or that does not occur naturally in the specific spatial arrangement in wild type plant cells, or that is localised at a place in the genome of the wild type plant cell at which it does not occur naturally. Preferably, the foreign nucleic acid molecule is a recombinant molecule, which consists of different elements, the combination or specific spatial arrangement of which does not occur naturally in plant cells.

In principle, the foreign nucleic acid molecule can be any nucleic acid molecule, which effects an increase in the activity of a protein according to the invention in the plant cell or plant.

In conjunction with the present invention, the term "genome" is to be understood to mean the totality of the genetic material present in a plant cell. It is known to the person skilled in the art that, as well as the cell nucleus, other compartments (e.g. plastids, mitochondria) also contain genetic material.

A preferred embodiment of the present invention relates to a genetically modified plant cell according to the invention or a genetically modified plant according to the invention, wherein the genetic modification consists in the introduction of at least one foreign nucleic acid molecule into the genome of the plant and the foreign nucleic acid molecule codes for a protein according to the invention.

A further embodiment of the present invention relates to a genetically modified plant cell according to the invention or a genetically modified plant according to the invention, wherein the genetic modification consists in the introduction of at least one foreign nucleic acid molecule into the genome of the plant and wherein the foreign nucleic acid molecule comprises a nucleic acid molecule according to the invention, preferably a nucleic acid molecule according to the invention, isolated from *Arabidopsis thaliana*, particularly preferably isolated from rice.

A large number of techniques are available for the introduction of DNA into a plant host cell. These techniques include the transformation of plant cells with T-DNA using *Agrobacterium tumefaciens* or *Agrobacterium rhizogenes* as the transformation medium, the fusion of protoplasts, injection, the electroporation of DNA, the introduction of DNA by means of the biolistic approach as well as other possibilities.

The use of *agrobacteria*-mediated transformation of plant cells has been intensively investigated and adequately described in EP 120516; Hoekema, in: The Binary Plant Vector System Offsetdrukkerij Kanters B. V., Alblasserdam (1985), Chapter V; Fraley et al., Crit. Rev. Plant Sci. 4, 1-46 and by An et al. EMBO J. 4, (1985), 277-287. For the transformation of potato, see Rocha-Sosa et al., EMBO J. 8, (1989), 29-33, for example.

The transformation of monocotyledonous plants by means of vectors based on *Agrobacterium* transformation has also been described (Chan et al., Plant Mol. Biol. 22, (1993), 491-506; Hiei et al., Plant J. 6, (1994) 271-282; Deng et al, Science in China 33, (1990), 28-34; Wilmink et al., Plant Cell Reports 11, (1992), 76-80; May et al., Bio/Technology 13, (1995), 486-492; Conner and Domisse, Int. J. Plant Sci. 153 (1992), 550-555; Ritchie et al, Transgenic Res. 2, (1993), 252-265). 153 (1992), 550-555; Ritchie et al, Transgenic Res. 2, (1993), 252-265). An alternative system to the transformation of monocotyledonous plants is transformation by means of the biolistic approach (Wan and Lemaux, Plant Physiol. 104, (1994), 37-48; Vasil et al., Bio/Technology 11 (1993), 1553-1558; Ritala et al., Plant Mol. Biol. 24, (1994), 317-325; Spencer et al., Theor. Appl. Genet. 79, (1990), 625-631), protoplast transformation, electroporation of partially permeabilised cells and the introduction of DNA by means of glass fibres. In particular, the transformation of maize has been described in the literature many times (cf. e.g. WO95/06128, EP0513849, EP0465875, EP0292435; Fromm et al., Biotechnology 8, (1990), 833-844; Gordon-Kamm et al., Plant Cell 2, (1990), 603-618; Koziel et al., Biotechnology 11 (1993), 194-200; Moroc et al., Theor. Appl. Genet. 80, (1990), 721-726).

The successful transformation of other types of cereal has also already been described, for example, for barley (Wan and Lemaux, see above; Ritala et al., see above; Krens et al., Nature 296, (1982), 72-74) and for wheat (Nehra et al., Plant J. 5, (1994), 285-297). All the above methods are suitable within the framework of the present invention.

Amongst other things, the plant cells according to the invention and the plants according to the invention can be differentiated from wild type plant cells and wild type plants respectively in that they contain a foreign nucleic acid molecule, which does not occur naturally in wild type plant cells or wild type plants, or in that such a molecule is present integrated at a place in the genome of the plant cell according to the invention or in the genome of the plant according to the invention at which it does not occur in wild type plant cells or wild type plants, i.e. in a different genomic environment. Furthermore, plant cells according to the invention and plants according to the invention of this type differ from wild type plant cells and wild type plants respectively in that they contain at least one copy of the foreign nucleic acid molecule stably integrated within their genome, possibly in addition to naturally occurring copies of such a molecule in the wild type plant cells or wild type plants. If the foreign nucleic acid molecule(s) introduced into the plant cells according to the invention or into the plants according to the invention is (are) additional copies of molecules already occurring naturally in the wild type plant cells or wild type plants respectively, then the plant cells according to the invention and the plants according to the invention can be differentiated from wild type plant cells or wild type plants respectively in particular in that this additional copy or these additional copies is (are) localised at places in the genome at which it does not occur (or they do not occur) in wild type plant cells or wild type plants. This can be verified, for example, by using a Southern blot analysis.

Furthermore, the plant cells according to the invention and plants according to the invention can be differentiated from wild type plant cells or wild type plants respectively preferably by at least one of the following features: If the foreign nucleic acid molecule that has been introduced is heterologous with respect to the plant cell or plant, then the plant cells according to the invention or plants according to the invention have transcripts of the introduced nucleic acid molecules. These can be verified, for example, by Northern blot analysis or by RT-PCR (Reverse Transcription Polymerase Chain Reaction). Preferably, the plant cells according to the invention and the plants according to the invention which exhibit an elevated activity of a protein according to the invention, contain a protein, which is coded for by an introduced nucleic acid molecule. This can be demonstrated by immunological methods, for example, in particular by a Western blot analysis. Plant cells according to the invention and plants according to the invention which exhibit a reduced activity of a protein according to the invention, show a reduced quantity of the relevant protein compared to corresponding wild type plant cells or wild type plants which have not been genetically modified, when investigated using said immunological methods.

If the foreign nucleic acid molecule that has been introduced is homologous with respect to the plant cell or plant, the plant cells according to the invention or plants according to the invention can be differentiated from wild type plant cells or wild type plants respectively due to the additional expression of the introduced foreign nucleic acid molecule, for example. The plant cells according to the invention and the plants according to the invention preferably contain transcripts of the foreign nucleic acid molecules. This can be demonstrated by Northern blot analysis, for example, or using so-called quantitative PCR.

In a special embodiment, the plant cells according to the invention and the plants according to the invention are transgenic plant cells or transgenic plants respectively In a further embodiment of the present invention, plant cells according to the invention and plants according to the invention synthesise a modified starch compared to starch isolated from wild type plant cells or wild type plants which have not been genetically modified.

In conjunction with the present invention, the term "modified starch" means that the starch has changed physical-chemical characteristics compared with non-modified starch obtainable from corresponding wild type plant cells or wild type plants.

In a further embodiment, the plant cells according to the invention or the plants according to the invention synthesise a modified starch which has an elevated content of starch phosphate and/or a modified phosphate distribution compared with starch isolated from corresponding wild type plant cells or wild type plants.

In a further embodiment of the method according to the present invention, the plant cells according to the invention or the plants according to the invention synthesise a modified starch which has a modified C-3/C-6 ratio of the starch phosphate compared with corresponding wild type plants cells which have not been genetically modified or plants which have not been genetically modified. Especially preferred in this case are starches which exhibit an elevated fraction of starch phosphate bound in the C-3 position compared with starch phosphate bound in the C-6 position, in comparison to corresponding starches isolated from wild type plant cells which have not been genetically modified or plants which have not been genetically modified.

In conjunction with the present invention, the term "phosphate distribution" should be understood as the fraction of the starch phosphate bound in the C-2 position, C-3 position or C-6 position of a glucose molecule relative to the total starch phosphate content of alpha-1,4-glucans.

In conjunction with the present invention, the term "C-2/C-3/C-6 ratio" should be understood as the fraction of the starch phosphate in which the starch phosphate of an alpha-1,4-glucan bound respectively in the C-2 position, C-3 position or C-6 position contributes to the total starch phosphate content of the alpha-1,4-glucan concerned (C-2 position+C-3 position+C-6 position).

In conjunction with the present invention, the term "C-3/C-6 ratio" should be understood as the fraction of the starch phosphate in which the starch phosphate of an alpha-1,4-glucan bound respectively in the C-3 position and in the C-6 position contributes to the sum of the starch phosphate bound in the C-3 position and in the C-6 position (C-3 position+C-6 position) of the alpha-1,4-glucan concerned.

A further object of the present invention is plant cells according to the invention or plants according to the invention which synthesise a modified starch, wherein the modified starch is characterised in that it has an elevated content of phosphate covalently bound to the starch in the C-3 position of the glucose molecule compared to starch from corresponding wild type plant cells or wild type plants.

A further object of the present invention is plants containing plant cells according to the invention.

Description of Sequences

SEQ ID NO 1: Nucleic acid sequence containing the coding region of the A.t.-OK1 protein from *Arabidopsis thaliana*. This sequence is inserted in the vectors OK1-pGEM-T and OK1-pDEST™17.

SEQ ID NO 2: Amino acid sequence coding for the A.t.-OK1 protein from *Arabidopsis thaliana*. This sequence can be derived from the nucleic acid sequence shown under SEQ ID NO 1.

SEQ ID NO 3: Nucleic acid sequence containing the coding region of the O.s.-OK1 protein from *Oryza sativa*. This sequence is inserted in the vector M150.

SEQ ID NO 4: Amino acid sequence coding for the O.s.-OK1 protein from *Oryza sativa*. This sequence can be derived from the nucleic acid sequence shown under SEQ ID NO 3.

SEQ ID NO 5: Peptide sequence coding for the phospho-histidine domain of the OK1 proteins from *Arabidopsis thaliana, Oryza sativa* and *Sorghum bicolor*.

SEQ ID NO 6: Peptide sequence contained in the amino acid sequence coding for an H.v.-OK1 protein from barley.

SEQ ID NO 7: Peptide sequence contained in the amino acid sequence coding for an H.v.-OK1 protein from barley.

SEQ ID NO 8: Peptide sequence contained in the amino acid sequence coding for an H.v.-OK1 protein from barley.

SEQ ID NO 9: Partial nucleic acid sequence coding for an H.v.-OK1 protein from barley. This nucleic acid sequence has been identified by means of the peptide sequences shown under SEQ ID NO 6, SEQ ID NO 7 and SEQ ID NO 8 using the "Blast search" facility in the TIGR database.

SEQ ID NO 10: Partial amino acid sequence coding for an H.v.-OK1 protein from barley. The amino acid sequence shown can be derived from the nucleic acid sequence shown under SEQ ID NO 9.

SEQ ID NO 11: Peptide sequence contained in the amino acid sequence coding for an S.t.-OK1 protein from potato.

SEQ ID NO 12: Peptide sequence contained in the amino acid sequence coding for an S.t.-OK1 protein from potato.

SEQ ID NO 13: Peptide sequence contained in the amino acid sequence coding for an S.t.-OK1 protein from potato.

SEQ ID NO 14: Peptide sequence contained in the amino acid sequence coding for an S.t.-OK1 protein from potato.

SEQ ID NO 15: Partial nucleic acid sequence coding an S.t.-OK1 protein from potato. This nucleic acid sequence has been identified by means of the peptide sequences shown under SEQ ID NO 11, SEQ ID NO 12, SEQ ID NO 13 and SEQ ID NO 14 using the "Blast Search" facility in the TIGR database.

SEQ ID NO 16: Partial amino acid sequence coding for an S.t.-OK1 protein from potato. The amino acid sequence shown can be derived from the nucleic acid sequence shown under SEQ ID NO 15.

SEQ ID NO 17: Peptide sequence contained in the amino acid sequence coding for an S.b.-OK1 protein from millet.

SEQ ID NO 18: Peptide sequence contained in the amino acid sequence coding for an S.b.-OK1 protein from millet.

SEQ ID NO 19: Peptide sequence contained in the amino acid sequence coding for an S.b.-OK1 protein from millet.

SEQ ID NO 20: Peptide sequence contained in the amino acid sequence coding for an S.b.-OK1 protein from millet.

SEQ ID NO 21: Partial nucleic acid sequence coding for an S.b.-OK1 protein from millet. This nucleic acid sequence has been identified by means of the peptide sequences shown under SEQ ID NO 17, SEQ ID NO 18, SEQ ID NO 19 and SEQ ID NO 20 using the "Blast Search" facility in the TIGR database.

SEQ ID NO 22: Partial amino acid sequence coding for an S.b.-OK1 protein from millet. The amino acid sequence shown can be derived from the nucleic acid sequence shown under SEQ ID NO 21.

SEQ ID NO 23: Peptide sequence contained in the amino acid sequence coding for a T.a.-OK1 protein from wheat.

SEQ ID NO 24: Peptide sequence containing the amino acid sequence coding for a T.a.-OK1 protein from wheat.

SEQ ID NO 25: Partial nucleic acid sequence coding for a T.a.-OK1 protein from wheat. This nucleic acid sequence has been identified by means of the peptide sequences shown under SEQ ID NO 23 and SEQ ID NO 24 using the "Blast Search" facility in the TIGR database.

SEQ ID NO 26 Partial amino acid sequence coding for a T.a.-OK1 protein from wheat. The amino acid sequence shown can be derived from the nucleic acid sequence shown under SEQ ID NO 25.

DESCRIPTION OF THE FIGURES

FIG. 2A) shows a denaturing (SDS) acrylamide gel stained with Coomassie Blue on completion of the electrophoresis. FIG. 2 B) shows the autoradiography of a denaturing (SDS) acylamide gel. The same amounts of the same samples were applied to each of the two gels. M: Standard protein molecular weight marker; R1: Sample from reaction vessel 1 according to Example 7 (after incubating an OK1 protein with ATP); R2: Sample from reaction vessel 2 according to Example 7 (after incubating an OK1 protein with ATP the protein was heated to 95° C.); R3: Sample from reaction vessel 3 according to Example 7 (after incubating an OK1 protein with ATP the protein was incubated in 0.5 M HCl); R4: Sample from reaction vessel 4 according to Example 7 (after incubating an OK1 protein with ATP the protein was incubated in 0.5 M NaOH).

FIG. 5 A) shows a Western Blot. FIG. 5 B) shows the autoradiography of a denaturing (SDS) acrylamide gel. The same amounts of the same samples were applied to each of the two gels. The OK1 protein was incubated either with randomised radioactively labeled ATP or with ATP specifically radioactively labeled in the gamma position. On completion of incubation, the proteins were either heated to 30° C. or 95° C., or incubated in 0.5 M NaOH or 0.5 M HCl respectively.

GENERAL METHODS

Figure 1:
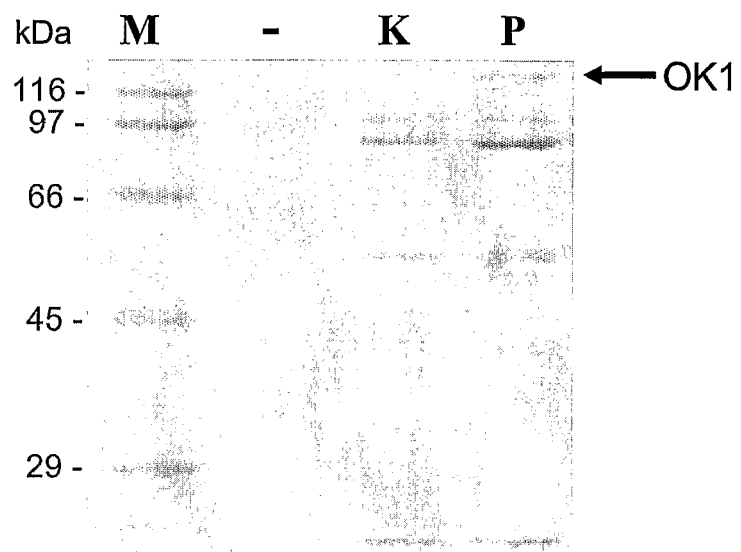
FIG. 1: Denaturing acrylamide gel for identifying proteins from *Arabidopsis thaliana*, which preferably bind to non-phosphorylated starch in comparison with phosphorylated starch. A standard protein molecular weight marker is shown in trace "M". Proteins obtained after incubating control preparation C from Example 1d) are shown in trace "-". Protein extracts of *Arabidopsis thaliana*, obtained after incubation with non-phosphorylated starch, isolated from leaves of an *Arabidopsis thaliana* sex1-3 mutant (Preparation B, Example 1d)), are shown in trace "K". Protein extracts of *Arabidopsis thaliana*, obtained after incubation with starch, isolated from leaves of an *Arabidopsis thaliana* sex1-3 which was phosphorylated retrospectively in vitro with an R1 protein (Preparation A, Example 1 d), are shown in trace "P". On completion of electrophoresis, the acrylamide gel was stained with Coomassie Blue.

In the following, methods are described, which can be used for carrying out the method according to the invention. These methods constitute specific embodiments of the present invention but do not restrict the present invention to these methods. The person skilled in the art knows that he can implement the invention in the same way by modifying the methods described and/or by replacing individual parts of the methods by alternative parts of the methods.

1. Manufacture of Protein Extracts from Plant Tissue a) Manufacture of Protein Extracts from Plant Tissues Leaf material is frozen in liquid nitrogen immediately after harvesting and subsequently homogenised in the mortar under liquid nitrogen. The reduced leaf material is mixed with ca. 3.5 times the volume (relative to the weight of the leaf material used) of cold (4° C.) binding buffer and macerated for 2×10 s using an Ultraturrax (maximum speed). After the first treatment with an Ultraturrax, the reduced leaf material is cooled on ice before the second treatment is carried out. The treated leaf material is then passed through a 100 µm nylon mesh and centrifuged for 20 min (50 ml centrifuge vessel, 20,000×g, 4° C.).

b) Precipitation of the Proteins Contained in the Protein Extracts

The supernatant obtained following centrifugation according to Step a) is removed and its volume determined. To precipitate proteins, ammonium sulphate is added continuously to the supernatant over a period of 30 minutes while stirring on ice down to a final concentration of 75% (weight/volume). The supernatant is subsequently incubated for a further hour on ice while stirring. The proteins precipitated from the supernatant are pelletised at 20,000×g and 4° C. for 10 min and the pellet subsequently absorbed in 5 ml of binding buffer, i.e. the proteins present in the pellet are dissolved.

c) Desalting of the Precipitated Proteins

The dissolved proteins are desalted using a PD10 column filled with Sephadex G25 (Amersham Bioscience, Freiburg, Prod. No. columns: 17-0851-01, Prod. No. Sephadex G25-M: 17-0033-01) at a temperature of 4° C., i.e. the ammonium sulphate used for the precipitation under step b) is separated from the dissolved proteins. The PD10 column is equilibrated with binding buffer before the proteins dissolved in accordance with Step b) are applied. For this purpose, 5 ml of binding buffer are spread over the column in each case. Subsequently, 2.5 ml of the protein solution obtained in accordance with Step b) are added to each column before proteins are eluted from the column with 3.5 ml binding buffer.

d) Determination of the Protein Concentration

The protein concentration is determined with a Bradford assay (Biorad, Munich, Prod. No. 500-0006 (Bradford, 1976, Anal. Biochem. 72, 248-254)).

e) Composition of the Binding Buffer [

| Binding buffer: | 50 mM | HEPES/NaOH (or KOH), pH 7.2 |
|---|---|---|
| | 1 mM | EDTA |
| | 2 mM | Dithioerythritol (DTE) |
| | 2 mM | Benzamidine |
| | 2 mM | ε-aminocaproic acid |
| | 0.5 mM | PMSF |
| | 0.02% | Triton X-100 |

2. Isolation of Leaf Starch a) Isolation of Starch Granules from Plant Tissues

Leaf material is frozen immediately after harvesting in liquid nitrogen. The leaf material is homogenised in portions in the mortar under liquid nitrogen and absorbed into a total of ca. 2.5-times the volume (weight/volume) of starch buffer. In addition, this suspension is again homogenised in a Waring blender for 20 s at maximum speed. The homogenate is passed through a nylon mesh (100 µm mesh width) and centrifuged for 5 minutes at 1,000×g. The supernatant with the soluble proteins is discarded.

b) Purifying the Starch Isolated from the Plant Tissues

After removing the green material lying on top of the starch by rinsing off the green material with starch buffer, the pellet containing the starch obtained from Step a) is absorbed in starch buffer and successively passed through nylon meshes with different mesh widths (in the order 60 µm, 30 µm, 20 µm). The filtrate is centrifuged using a 10 ml Percoll cushion (95% (v/v) Percoll (Pharmacia, Uppsala, Sweden), 5% (v/v) 0.5M HEPES-KOH pH7.2) (Correx tube, 15 min, 2,000×g). The sediment obtained after this centrifugation is resuspended once in starch buffer and centrifuged again (5 min, 1,000×g).

c) Removal of the Proteins Bound to the Starch

Following Step b), starch granules are obtained, which contain proteins bound to the starch. The proteins bound to the surface of the starch granules are removed by incubating four times with 0.5% SDS (sodium lauryl sulphate) for 10-15 minutes in each case at room temperature under agitation. Each washing step is followed by a centrifugation (5 min, 5,000×g), in order to separate the starch granules from the respective wash buffer.

d) Purifying the Starch that has been Freed of Proteins

The starch obtained from Step c), which has been freed from the proteins bound to its surface, is subsequently removed by incubating four times with wash buffer for 10-15 minutes in each case at room temperature under agitation. Each washing step is followed by a centrifugation (5 min, 1000×g), in order to separate the starch granules from the respective wash buffer. These purification steps serve mainly to remove the SDS used in the incubations in Step c).

e) Determination of the Concentration of Isolated Starch

The amount of starch isolated in Step d) is determined photometrically. After suitable dilution, the optical density of the starch suspension is measured against a calibration curve at a wavelength of 600 nm. The linear range of the calibration curve is located between 0 and 0.3 extinction units.

To produce the calibration curves, starch, for example isolated from leaves of an *Arabidopsis thaliana* sex1-3 mutant, is dried under vacuum, weighed and absorbed in a defined volume of water. The suspension so obtained is diluted with water in several steps in a ratio of 1 to 1 in each case until a suspension of ca. 5 µg starch per ml of water is obtained. The suspensions obtained by the individual dilution steps are measured in the photometer at a wavelength of 600 nm. The absorption values obtained for each suspension are plotted against the concentration of starch in the respective suspension. The calibration curve obtained should follow a linear mathematical function in the range from 0 µg starch per ml of water to 0.3 µg starch per ml of water.

f) Storage of Isolated Starch

The starch can either be used directly without further storage for further tests, or stored in aliquots in 1.5 mL Eppendorf vessels at −20° C. Both the frozen starch and the non-stored, freshly isolated starch can be used, if required, for the methods described in the present invention relating to in vitro phosphorylation and/or binding test, for example.

g) Composition of Buffers Used

| 1× starch buffer: | 20 mM | HEPES-KOH, pH 8.0 |
|---|---|---|
| | 0.2 mM | EDTA |
| | 0.5% | Triton X-100 |
| Wash buffer: | 50 mM | HEPES/KOH, pH 7.2 |

3. Recombinant Expression of an Identified Starch-Phosphorylating Protein a) Manufacture of a Bacterial Expression Vector Containing a cDNA, which Codes for a Starch-Phosphorylating Protein The cDNA coding for a starch-phosphorylating protein can be amplified, for example, using mRNA or poly-A-plus-mRNA from plant tissues as a "template", by means of a polymerase chain reaction (PCR). For this purpose, a reverse transcriptase is first used for the manufacture of a cDNA strand, which is complementary to an mRNA, which codes for a starch-phosphorylating protein, before the cDNA strand concerned is amplified by means of DNA polymerase. So-called "kits" containing substances, enzymes and instructions for carrying out PCR reactions are available for purchase (e.g. SuperScript™ One-Step RT-PCR System, Invitrogen, Prod. No.: 10928-034. The amplified cDNA coding a starch phosphorylating protein can then be cloned in a bacterial expression vector e.g. PDEST™17 (Invitrogen). PDEST™17 contains the T7 promoter which is used to initiate the transcription of the T7-RNA polymerase. Furthermore, the expression vector PDEST™17 contains a Shine Dalgarno sequence in the 5'-direction of the T7 promoter followed by a start codon (ATG) and by a so-called His tag. This His tag consists of six codons directly following one another, which each code for the amino acid histidine and are located in the reading frame of the said start codon. The cloning of a cDNA coding for a starch-phosphorylating protein in pDEST™17 is carried out in such a way that a translational fusion occurs between the codons for the start codon, the His tag and the cDNA coding for a starch-phosphorylating protein. As a result of this, following transcription initiated on the T7 promoter, and subsequent translation, a starch-phosphorylating protein is obtained, which contains additional amino acids containing the His tag on its N-terminus.

However, other vectors, which are suitable for expression in microorganisms, can also be used for the expression of a starch-phosphorylating protein. Expression vectors and associated expression strains are known to the person skilled in the art and are also available for purchase from the appropriate dealer in suitable combinations.

b) Manufacture of Expression Clones in *Escherichia coli*

First of all, an appropriate transformation-competent *E. coli* strain, which chromosomally codes for a T7-RNA polymerase, is transformed with the expression plasmid manufactured under Step a), and subsequently incubated overnight at 30° C. on culture medium solidified with agar. Suitable expression strains are, for example, BL21 strains (Invitrogen Prod. No.: C6010-03), which chromosomally code for a T7-RNA polymerase under the control of an IPTG-inducible promoter (lacZ).

Bacteria colonies resulting from the transformation can be investigated using methods known to the person skilled in the art to see whether they contain the required expression plasmid containing a cDNA coding for the starch-phosphorylating protein. At the same time, expression clones are obtained.

c) Expression of a Starch-Phosphorylating Protein in *Escherichia coli*

First of all, a preliminary culture is produced. To do this, an expression clone obtained in accordance with Step b) is seeded in 30 ml Terrific Broth (TB medium) containing an antibiotic for selection on the presence of the expression plasmid, and incubated overnight at 30° C. under agitation (250 rpm).

A main culture for the expression of a starch-phosphorylating protein is then produced. To do this, in each case, 1 liter Erlenmeyer flasks, each containing 300 ml of TB medium, pre-heated to 30° C., and an antibiotic for selection on the presence of the expression plasmid are each seeded with 10 ml of an appropriate pre-culture and incubated at 30° C. under agitation (250 rpm) until an optical density (measured at a wavelength of 600 nm ($OD_{600}$) of ca. 0.8 is achieved.

If, for the expression of a starch-phosphorylating protein, an expression plasmid is used, in which the expression of the starch-phosphorylating protein is initiated by means of an inducible system (e.g. the expression vector pDEST™17 in BL21 *E. coli* strains, inducible by means of IPTG), then on reaching an $OD_{600}$ of ca. (0.8, the inductor concerned (e.g. IPTG) is added to the main culture. After adding the inductor, the main culture is incubated at 30° C. under agitation (250 rpm) until an $OD_{600}$ of ca. 1.8 is achieved. The main culture is then cooled for 30 minutes on ice before the cells of the main culture are separated from the culture medium by centrifugation (10 minutes at 4,000×g and 4° C.).

4. Purification of a Starch-Phosphorylating Protein a) Breaking Down of Cells Expressing a Starch-Phosphorylating Protein The cells obtained in Step c), Item 3 General Methods are resuspended in lysis buffer. In doing so, ca. 4 ml lysis buffer is added to about 1 g of cells. The resuspended cells are then incubated for 30 minutes on ice before they are broken down using an utrasonic probe (Baudelin Sonoplus UW 2070, Baudelin electronic, Berlin, settings: Cycle 6, 70%, 1 minute) under continuous cooling by means of the ice. Care must be taken here to ensure that the cell suspension is not heated too much during the ultrasonic treatment. The suspension obtained after the ultrasonic treatment is centrifuged (12 minutes at 20,000×g, 4° C.) and the supernatant obtained after centrifugation is filtered using a filter with a pore size of 45 μm.

b) Purification of the Starch-Phosphorylating Protein

If the starch-phosphorylating protein expressed in *E. coli* cells is a fusion protein with a His tag, then purification can take place using nickel ions, to which the His tag binds with greater affinity. To do this, 25 ml of the filtrate obtained in Step d) is mixed with 1 ml Ni-agarose slurry (Qiagen, Prod. No.: 30210) and incubated for 1 hour on ice. The mixture of Ni-agarose slurry and filtrate is subsequently spread over a polystyrene column (Pierce, Prod. No.: 29920). The product, which runs through the column, is discarded. The column is next washed by adding 8 ml of lysis buffer, the product, which runs through the column, again being discarded. Elution of the starch-phosphorylating protein then takes place by fractionated addition to the column of 1 ml E1 buffer twice, followed by 1 ml E2 buffer once and subsequently 1 ml E3 buffer five times. The product, which runs through the column, which is produced by adding the individual fraction of the appropriate elution buffer (E1, E2, E3 buffer) to the column, is collected in separate fractions. Aliquots of these fractions are subsequently analysed by means of denaturing SDS acrylamide gel electrophoresis followed by Coomassie Blue staining. The fractions, which contain the starch-phosphorylating protein in sufficient quantity and satisfactory purity, are purified and concentrated using pressurised filtration at 4° C. Pressurised filtration can be carried out, for example, using an Amicon cell (Amicon Ultrafiltration Cell, Model 8010, Prod. No.: 5121) using a Diaflo PM30 membrane (Millipore, Prod. No.: 13212) at 4° C. Other methods known to the person skilled in the art can also be used for concentration however.

c) Composition of Buffers Used

| Lysis buffer: | 50 mM | HEPES |
|---|---|---|
| | 300 mM | NaCl |
| | 10 mM | Imidazole |
| pH 8.0 (adjust with NaOH) | | |
| | 1 mg/ml | Lysozyme (add immediately before using the buffer) |

-continued

¼ tablet per 10 ml of protease inhibitors Complete EDTA free, (Roche Product No.: 1873580) (add immediately before using the buffer)

| Elution buffer E1: | 50 mM | HEPES |
| --- | --- | --- |
| | 300 mM | NaCl |
| | 50 mM | Imidazole |
| | pH 8.0 (adjust with NaOH) | |
| Elution buffer E2: | 50 mM | HEPES |
| | 300 mM | NaCl |
| | 75 mM | Imidazole |
| | pH 8.0 (adjust with NaOH) | |
| Elution buffer E3: | 50 mM | HEPES |
| | 300 mM | NaCl |
| | 250 mM | Imidazole |
| | pH 8.0 (adjust with NaOH) | |

5. Recombinant Expression of an R1 Protein

The recombinant expression of an R1 protein is described in the literature (Ritte et al., 2002, PNAS 99, 7166-7171; Mikkelsen et al., 2004, Biochemical Journal 377, 525-532), but can also be carried out in accordance with the methods relating to the recombinant expression of a starch-phosphorylating protein described above under Item 3, General Methods.

6. Purification of an R1 Protein

The purification of an R1 protein is described in the literature (Ritte et al., 2002, PNAS 99, 7166-7171; Mikkelsen et al., Mikkelsen et al., 2004, Biochemical Journal 377, 525-532), but can also be carried out in accordance with the methods relating to the purification of a starch-phosphorylating protein described above under Item 4, General Methods if an R1 fusion protein, which contains a His tag, is produced by expression of R1 in E. coli cells.

7. In Vitro Manufacture of Phosphorylated Starch Starting from Non-Phosphorylated Starch a) In Vitro Phosphorylation of Non-Phosphorylated Starch Starch, which does not contain starch phosphate (e.g. isolated from leaves of Arabidopsis thaliana sex1-3 mutants using the methods described above under Item 2, General Methods), is mixed with R1 buffer and with purified R1 protein (ca. 0.25 μg R1 protein per mg starch) in order to produce a starch content of 25 mg per ml. This reaction preparation is incubated overnight (ca. 15 h) at room temperature under agitation. R1 bound to the starch present in the reaction preparation is removed on completion of the reaction by washing four times with ca. 800 μl 0.5% SDS in each case. Subsequently, the SDS still present in the in vitro phosphorylated starch is removed by washing five times with 1 ml wash buffer in each case. All washing steps are carried out at room temperature for 10 to 15 minutes under agitation. Each washing step is followed by a centrifugation (2 min, 10,000× g), in order to separate the starch granules from the respective SDS buffer or wash buffer.

b) Composition of Buffers Used

| R1 buffer: | 50 mM | HEPES/KOH, pH 7.5 |
| --- | --- | --- |
| | 1 mM | EDTA |
| | 6 mM | MgCl$_2$ |
| | 0.5 mM | ATP |
| Wash buffer: | 50 mM | HEPES/KOH, pH 7.2 |

8. Binding of Proteins to Phosphorylated Starch or Non-Phosphorylated Starch a) Isolation of P-Starch Protein Complexes or Non-Phosphorylated Starch Protein Complexes Ca. 50 mg of P-starch or ca. 50 mg of non-phosphorylated starch are resuspended in separate preparations in ca. 800 μl of protein extract in each case. The protein concentration of the protein extracts should be ca. 4 mg to 5 mg per ml in each case. The incubation of the P-starch or non-phosphorylated starch with protein extracts is carried out at room temperature for 15 minutes at 4° C. under agitation. On completion of the incubation, the reaction preparations are centrifuged out using a Percoll cushion (4 ml) (15 minutes, 3500 rpm, 4° C.). After centrifugation, proteins that are not bound to phosphorylated starch or P-starch will be found in the supernatant and can be removed with a Pasteur pipette. The supernatant is discarded. The sedimented pellet containing P-starch and non-phosphorylated starch, including the proteins bound to the respective starches (P-starch protein complexes or non-phosphorylated starch protein complexes respectively), obtained after centrifugation is washed twice with 1 ml of wash buffer in each case (see above, General Methods under item 7.b) by incubating for 3 minutes at 4° C. in each case under agitation. The washing step is followed by a centrifugation (5 minutes, 8000 rpm, 4° C. in a table centrifuge, Hettich EBA 12R) in order to separate the P-starch or non-phosphorylated starch respectively from the wash buffer.

b) Dissolving the Proteins Bound in the P-Starch Protein Complexes or Non-Phosphorylated Starch Protein Complexes Respectively The P-starch protein complexes or non-phosphorylated starch protein complexes respectively obtained in Step a) are resuspended in ca. 150 μl SDS test buffer and incubated at room temperature for 15 minutes under agitation. The P-starch or non-phosphorylated starch respectively is subsequently removed from the dissolved proteins by centrifugation (1 minute, 13,000 rpm, room temperature, Eppendorf table centrifuge). The supernatant obtained after centrifugation is centrifuged again in order to remove any residues of P-starch or non-phosphorylated starch respectively (1 minute, 13,000 rpm, room temperature, Eppendorf table centrifuge) and removed. As a result, dissolved proteins, which bind to the P-starch or non-phosphorylated starch respectively, are obtained.

c) Composition of Buffers Used

| SDS test buffer: | 187.5 mM | Tris/HCl pH 6.8 |
| --- | --- | --- |
| | 6% | SDS |
| | 30% | Glycerine |
| | ~0.015% | Bromophenol blue |
| | 60 mM | DTE (add fresh) |
| Percoll: | Percoll is dialysed overnight against a solution consisting of and 25 mM HEPES/KOH, pH 7.0 | |

9. Separation of Proteins, which Bind to P-Starch and/or Non-Phosphorylated Starch The dissolved proteins obtained in Step c) under Item 8. General Methods relating to the binding of proteins to P-starch or non-phosphorylated starch respectively are incubated for 5 minutes at 95° C. in each case and subsequently separated using denaturing polyacrylamide gel electrophoresis. In doing so, an equal volume is applied to the acrylamide gel in each case for the dissolved proteins obtained by binding to P-starch and for those obtained by binding to non-phosphorylated starch. The gel obtained on completion of electrophoresis is stained at least overnight with colloidal Coomassie (Roth, Karlsruhe, Roti-Blue Rod. No.: A152.1) and subsequently decolourised in 30% methanol, 5% acetic acid, or in 25% methanol.

10. Identification and Isolation of Proteins, which Bind to P-Starch and/or Non-Phosphorylated Starch a) Identification of Proteins with Increased Binding Activity Towards P-Starch in Comparison with Phosphorylated Starch Proteins, which, after separation by means of acrylamide gel electrophoresis and subsequent visualisation by staining (see above, Item 9, General Methods), exhibit an increased signal after binding to P-starch in comparison with a corresponding signal after binding to non-phosphorylated starch, have increased bonding activity towards P-starch in comparison with non-phosphorylated starch. By this means, it is possible to identify proteins, which have increased binding activity towards, P-starch in comparison with non-phosphorylated starch. Proteins, which have increased binding activity towards P-starch in comparison with non-phosphorylated starch, are excised from the acrylamide gel.

b) Identification of proteins, which have increased binding activity towards P-starch in comparison with non-phosphorylated starch Proteins identified in accordance with Step a) are digested with ttypsin and the peptides obtained are analysed by means of MALDI-TOF to determine the masses of the peptides obtained. Trypsin is a sequence-specific protease, i.e. trypsin only splits proteins at a specified position when the proteins concerned contain certain amino acid sequences. Trypsin always splits peptide bonds when the amino acids arginine and lysine follow one another starting from the N-terminus. In this way, it is possible to theoretically determine all peptides that would be produced following the trypsin digestion of an amino acid sequence. From the knowledge of the amino acids coding for the theoretically determined peptides, the masses of the peptides, which are obtained after theoretical trypsin digestion, can also be determined. Databases (e.g. NCBInr prospector.ucsf.edu/ucsfhtm14.0/msfit.htm; Swissprot cbrg. inf.ethz.ch/Server/MassSearch.html), which contain information concerning the masses of peptides after theoretical trypsin digestion, can therefore be compared with the real masses of peptides of unknown proteins obtained with MALDI-TOF-MS. Amino acid sequences, which have the same peptide masses after theoretical and/or real trypsin digestion, are to be looked upon as being identical. The databases concerned contain both peptide masses of proteins, the function of which has already been shown, and also peptide masses of proteins, which up to now only exist hypothetically by derivation from amino acid sequences starting from nucleic acid sequences obtained in sequencing projects. The actual existence and the function of such hypothetical proteins has therefore seldom been shown and, if there is a function at all, then this is usually based only on predictions and not on an actual demonstration of the function.

Bands containing proteins obtained in accordance with Step a) are excised from the acrylamide gel; the excised acrylamide piece is reduced and decolourised by incubating for approximately half an hour at 37° C. in ca. 1 ml 60% 50 mM $NH_4HCO_3$, 40% acetonitrile. The decolourising solution is subsequently removed and the remaining gel dried under vacuum (e.g. Speedvac). After drying, trypsin solution is added to digest the proteins contained in the gel piece concerned. Digestion takes place overnight at 37° C. After digestion, a little acetonitrile is added (until the acrylamide gel is stained white) and the preparation dried under vacuum (e.g. Speedvac). When drying is complete, just enough 5% formic acid is added to cover the dried constituents and incubated for a few minutes at 37° C. The acetonitrile treatment followed by drying is repeated once more. The dried constituents are subsequently absorbed in 0.1% TFA (trifluoroacetic acid, 5 µl to 10 µl) and dripped onto a carrier in ca. 0.5 µl portions. Equal amounts of matrix (ε-Cyano-4-hydroxy-cinnamic acid) are also applied to the carrier After crystallising out the matrix, the masses of peptides are determined by means of MALDI-TOF-MS-MS (e.g. Burker Reflex™ II, Bruker Daltonic, Bremen) With the masses obtained, databases are searched for amino acid sequences, which give the same masses after theoretical trypsin digestion. In this way, amino acid sequences can be identified, which code for proteins, which preferably bind to phosphorylated alpha-1,4-glucans and/or which need P-alpha-1,4-glucans as a substrate.

11. Method for Demonstrating Starch-Phosphorylating Activity of a Protein a) Incubation of Proteins with P-Starch and/or Non-Phosphorylated Starch In order to demonstrate whether a protein has starch-phosphorylating activity, proteins to be investigated can be incubated with starch and radioactively labeled ATP. To do this, ca. 5 mg of P-starch or ca. 5 mg of non-phosphorylated starch are incubated with the protein to be investigated (0.01 µg to 5.0 µg per mg of starch used) in 500 µl phosphorylation buffer for 10 minutes to 30 minutes at room temperature under agitation. The reaction is subsequently stopped by the addition of SDS up to a concentration of 2% (weight/volume). The starch granules in the respective reaction mixture are centrifuged out (1 minute, 13,000×g), and washed once with 900 µl of a 2% SDS solution and four times each with 900 µl of a 2 mM ATP solution. Each washing step is carried out for 15 minutes at room temperature under agitation. After each washing step, the starch granules are separated from the respective wash buffer by centrifugation (1 min, 13,000×g).

In addition, when carrying out an experiment to demonstrate starch-phosphorylating activity of a protein, further reaction preparations, which do not contain protein or contain inactivated protein, but which are otherwise treated in the same way as the reaction preparations described, should be processed as so-called controls.

b) Determination of the Amount of Phosphate Residues Incorporated in the P-Starch and/or Non-Phosphorylated Starch Due to Enzymatic Activity The starch granules obtained in accordance with Step a) can be investigated for the presence of radioactively labeled phosphate residues. To do this, the respective starch is resuspended in 100 µl of water and mixed with 3 ml of scintillation cocktail in each case (e.g. Ready Safe™, BECKMANN Coulter) and subsequently analysed using a scintillation counter (e.g. LS 6500 Multi-Purpose Scintillation Counter, BECKMANN COULTER™).

c) Identification of Proteins, which Preferably Use P-Starch as a Substrate

If a protein is incubated in separate preparations, once with P-starch and once with non-phosphorylated starch, in accordance with the method described under a), then, by comparing the values for the presence of starch phosphate obtained according to Step b), it can be determined whether the protein concerned has incorporated more phosphate in P-starch in comparison with non-phosphorylated starch. Thus, proteins which can introduce phosphate into P-starch but not into non-phosphorylated starch can also be identified, i.e., proteins which already require phosphorylated starch as substrate for a further phosphorylation reaction can be identified.

d) Composition of Buffers Used

| Phosphorylation buffer: | 50 mM | HEPES/KOH, pH 7.5 |
|---|---|---|
| | 1 mM | EDTA |
| | 6 mM | $MgCl_2$ |
| | 0.01 to 0.5 mM | ATP |

0.2 to 2 µCi per ml randomised $^{33}$P-ATP (alternatively, ATP, which contains a phosphate residue, which is specifically labeled in the gamma position, can also be used)

In conjunction with the present invention, the term "randomised ATP" is to be understood to mean ATP, which contains labeled phosphate residues both in the gamma position and in the beta position (Ritte et al. 2002, PNAS 99, 7166-7171). Randomised ATP is also described in the scientific literature as beta/gamma ATP. A method for manufacturing randomised ATP is described in the following.

i) Manufacture of Randomised ATP

The method described here for manufacturing randomised ATP using enzyme catalysed reactions is based on the following reaction mechanisms:

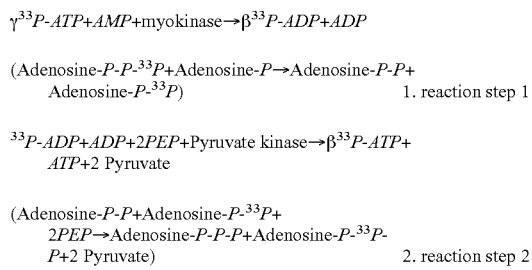

$\gamma^{33}$P-ATP+AMP+myokinase→$\beta^{33}$P-ADP+ADP (Adenosine-P-P-$^{33}$P+Adenosine-P→Adenosine-P-P+
Adenosine-P-$^{33}$P)  1. reaction step 1

$^{33}$P-ADP+ADP+2PEP+Pyruvate kinase→$\beta^{33}$P-ATP+
ATP+2 Pyruvate (Adenosine-P-P+Adenosine-P-$^{33}$P+
2PEP→Adenosine-P-P-P+Adenosine-P-$^{33}$P-
P+2 Pyruvate)  2. reaction step 2

The reaction equilibria lie on the product side but, in spite of this, this reaction produces a mixture consisting mainly of $\beta^{33}$P-ATP and some $\gamma^{33}$P-ATP.

ii) Carrying Out the 1st Reaction Step

ATP (100 µCi, 3000 Ci per mmol), which contains a phosphate residue labeled with $^{33}$P in the gamma position (Hartmann Analytic, 10 µCi/µl), is incubated with 2 µl myokinase (AMP-phosphotransferase, from rabbit muscle; SIGMA, Prod. Nd.: M3003 3.8 mg/ml, 1,626 units/mg) in 90 µl randomising buffer for 1 hour at 37° C. The reaction is subsequently stopped by incubating for 12 minutes at 95° C. before the reaction preparation is purified by means of centrifugal filtration using a Microcon YM 10 filter (Amicon, Millipore Prod. No. 42407) at 14,000×g for at least 10 minutes.

iii) Carrying Out the 2nd Reaction Step

2 µl pyruvate kinase (see below for how to manufacture an appropriate solution) and 3 µl 50 mM PEP (phosphoenolpyruvate) are added to the filtrate obtained in Step ii). This reaction mixture is incubated for 45 minutes at 30° C. before the reaction is stopped by incubating at 95° C. for 12 minutes. The reaction mixture is subsequently centrifuged (2 minutes, 12,000 rpm in an Eppendorf table centrifuge). The supernatant containing randomised ATP obtained after centrifugation is removed, aliquoted and can be stored at −20° C.

Manufacture of the Pyruvate Kinase Solution

15 µl pyruvate kinase (from rabbit muscle, Roche, Prod. No. 12815, 10 mg/ml, 200 units/mg at 25° C.) are centrifuged out, the supernatant discarded and the pellet absorbed in 27 µl pyruvate kinase buffer.

iv) Buffers Used

| Pyruvate kinase buffer: | 50 mM | HEPES/KOH pH 7.5 |
| | 1 mM | EDTA |
| Randomising buffer: | 100 mM | HEPES/KOH pH 7.5 |
| | 1 mM | EDTA |
| | 10% | Glycerol |
| | 5 mM | MgCl$_2$ |
| | 5 mM | KCl |
| | 0.1 mM | ATP |
| | 0.3 mM | AMP |

12. Demonstration of the Autophosphorylation of a Protein

In order to demonstrate whether a protein has autophosphorylating activity, proteins to be investigated can be incubated with radioactively labeled ATP. To do this, proteins to be investigated (50 µg to 100 µg) are incubated in 220 µl phosphorylation buffer (see above, Item 12 d), General Methods) for 30 minutes to 90 minutes at room temperature under agitation. The reaction is then stopped by adding EDTA up to a final concentration of 0.11 M. Ca. 2 µg to 4 µg of protein is then separated using denaturing polyacrylamide electrophoresis (7.5% acrylamide gel). The gel obtained after polyacrylamide gel electrophoresis is subjected to autoradiography. Proteins, which exhibit a signal in the autoradiography, carry a radioactive phosphate residue.

13. Identification of the C-Atom Positions of the Glucose Molecules of an Alpha-1,4-Glucan, into which Phosphate Residues are Introduced by a Starch-Phosphorylating Protein Which C-atom positions of the glucose molecules of an alpha-1,4-glucan are phosphorylated by a protein can be demonstrated in a controlled manner by hydrolysis of the phosphorylated glucans obtained by means of an appropriate protein in vitro, subsequent separation of the glucose monomers obtained after hydrolysis, followed by measurement of the phosphate incorporated by an appropriate protein in certain fractions of the glucose molecules.

a) Total Hydrolysis of the Alpha-1,4-Glucans

Water suspensions containing alpha-1,4-glucan are centrifuged, the sedimented pellet subsequently resuspended in 0.7 M HCl (Baker, for analysis) and incubated for 2 hours at 95° C. under agitation. On completion of incubation, the samples are briefly cooled and centrifuged (e.g. 2 minutes 10,000×g). The supernatant obtained is transferred to a new reaction vessel and neutralised by the addition of 2 M NaOH (Baker, for analysis). If a pellet remains, it is resuspended in 100 µl of water and the quantity of labeled phosphate present therein is determined as a control.

The neutralised supernatant is subsequently centrifuged over a 10 kDa filter. By measuring an aliquot of the filtrate obtained, the quantity of labeled phosphate in the filtrate is determined using a scintillation counter, for example.

b) Fractionation of the Hydrolysis Products and Determination of the Phosphorylated C-Atom Positions The neutralised filtrates of the hydrolysis products obtained by means of Step a) can be separated (when using radioactively labeled ATP about 3000 cpm) using high-pressure anion exchange chromatography (HPAE), for example. The neutralised filtrate can be diluted with H$_2$O to obtain the volume required for HPAE. In addition, glucose-6-phosphate (ca. 0.15 mM) and glucose-3-phosphate (ca. 0.3 mM) are added to the appropriate filtrates in each case as an internal control. Separation by means of HPAE can be carried out, for example, using a Dionex DX 600 Bio Lc system using a CarboPac PA 100 column (with appropriate pre-column) and a pulsed amperometric detector (ED 50). In doing so, before injecting the sample, the column is first rinsed for 10 minutes with 99% eluent C and 1% eluent D. A sample volume of 60 µl is then injected. The elation of the sample takes place under the following conditions:

| Flow rate: | 1 ml per minute | | |
| Gradient: | linearly increasing from 0 minutes to 30 minutes | | |
| | | Eluent C | Eluent D |
| | 0 minutes | 99% | 1% |
| | 30 minutes | 0% | 100% |
| | 35 Minutes | 0% | 100% |
| | Run terminated | | |

The hydrolysis products eluted from the column are collected in individual fractions of 1 ml each. As, in each case, non-labeled glucose-3-phosphate (Ritte et al. 2002, PNAS 99, 7166-7171) and non-labeled glucose-6-phosphate (Sigma, Prod. No.: G7879) have been added to the injected samples of hydrolysis products as internal standards, the fractions, which contain either glucose-3-phosphate or glucose-6-phosphate, can be determined by means of pulsed amperometric detection. By measuring the amount of labeled phosphates in the individual fractions and subsequently comparing with the fractions, which contain glucose-3-phosphate or glucose-6-phosphate, this can be used to determine those fractions, containing labeled glucose-6-phosphate or labeled glucose-3-phosphate. The amount of labeled phosphate in the fraction concerned is determined. From the ratios of the amounts of glucose-3-phosphate to glucose-6-phosphate measured for labeled phosphate in the individual hydrolysis products, it can now be determined which C-atom position is preferably phosphorylated by an alpha-1,4-glucan phosphorylating enzyme.

c) Buffers Used

| | |
|---|---|
| Eluent C: | 100 mM NaOH |
| Eluent D: | 100 mM NaOH |
| | 500 mM sodium acetate |

14. Preparation of the Samples for the Sequencing Using Q-TOF-MS-MS a) General Remarks Isolated proteins which can also be present in the form of bands excised from polyacrylamide gels, are first cleaved into smaller fragments by means of a trypsin digestion. The peptides formed are introduced into a hybrid mass spectrometer in which a time-of-flight (TOF) mass spectrometer is coupled to a quadrupole mass spectrometer. In the first phase of the measurement the first mass spectrometer (the quadrupole) is "switched off" and the masses of the peptides formed in the digestion can be determined in the TOF mass spectrometer. In the second phase a selected peptide is "filtered out" in the quadrupole, i.e., only this peptide can pass the quadrupole, all the others are deflected. The peptide is then broken by colliding with charged gas molecules in the "collision cell". In this case the "breaks" occur mainly at the peptide bonds. As a result, more or less statistically distributed peptide fragments which differ in mass are formed. The amino acid sequence of the peptides can then be determined by "sorting" these fragments. If overlapping peptides are obtained, the amino acid sequence of a protein can thus be obtained. The use of mass spectroscopy for identification and sequencing is known to the person skilled in the art and is sufficiently described in the specialist literature [e.g. P. Michael Conn (Ed.), 2003, Humana Press, New Jersey, ISBN: 1-58829-340-8]; J. R. Chapman (Ed.), 2000, Humana Press, SBN: 089603609X].

b) Reduction and Alkylation of Cysteine Residues of Proteins

The cysteine residues containing the amino acid sequences of the proteins to be analysed can be reduced/alkylated by means of gel electrophoresis before separation of the proteins. For this purpose, the proteins which are to be separated by means of gel electrophoresis are mixed with SDS sample buffer (must not contain any DTT or beta-mercaptoethanol). Freshly prepared DTT is then added to these samples up to a final concentration of 10 mM and the sample incubated for 3 minutes at 95° C. After cooling the sample to room temperature, freshly prepared iodacetamide is added up to a final concentration of 20 mM. The sample is incubated for 20 minutes at room temperature in the dark. The proteins present in the samples are then separated by means of acrylamide gel electrophoresis.

c) Isolation of the Proteins from the Acrylamide Gel

Protein bands containing proteins whose sequences are to be determined are excised using a clean scalpel as "edgeless" as possible and reduced (ca. 1 $mm^3$-cube). The reduced gel pieces are placed in a 0.5 ml or 1.5 ml reaction vessel and sedimented by short centrifugation.

d) Decolourisation of the Excised Gel Pieces

If gels stained using silver ions were used, the gel pieces obtained according to step c) are completely covered with a solution containing 30 mM K-ferricyanide and 100 mM Na-thiosulphate in the ratio 1:1 and agitated (Vertex) until the gel pieces are completely decolourised. The decolourising solution is then removed and the gel pieces are washed three times with 200 μl of high-purity water in each case (conductivity ca. 18 MOhm).

If gels stained with Coomassie Blue were used, the gel pieces; obtained according to step c) are incubated with a solution containing high-purity water and acetonitrile (degree of purity: at least HPLC pure) in the ratio 1:1 twice for 15 minutes in each case under agitation. The volume of the decolourising solution should correspond to ca. twice the volume of the gel. The washing solution is removed after each washing step.

After decolourisation has been completed, the gel pieces are mixed with one volume (relative to the gel pieces) of acetonitrile and incubated for 15 minutes at room temperature under agitation. The acetonitrile is removed and the gel pieces mixed with one volume of 100 mM ammonium bicarbonate, mixed and incubated for 5 minutes at room temperature. Acetonitrile is then added so as to give a ratio of 1:1 relative to the quantity of ammonium bicarbonate and acetonitrile. Incubation is carried out for a further 15 minutes at room temperature before the solution is removed and the remaining gel pieces are dried under vacuum (e.g. Speedvac).

e) Trypsin Digestion of the Proteins in the Gel Pieces

Trypsin solution (10 ng of trypsin per μl of 50 mM ammonium bicarbonate) is added in 10 μl portions to the dry gel pieces obtained according to step d). After every addition of trypsin solution, incubation on ice is carried out for 10 minutes in each case. Trypsin solution is added in portions until the gel pieces do not swell any further and are completely covered by trypsin solution. The trypsin solution is then removed and the gel pieces are incubated overnight at 37° C.

f) Isolation of the Peptides from the Acrylamide Gel

The samples obtained according to step e) are briefly centrifuged in order to collect the liquid contained in the reaction vessel, the liquid is removed and transferred to a new reaction vessel. The gel pieces are treated for 2 minutes with ultrasound (ultrasound water bath). The remaining gel pieces are then mixed with once their volume of 25 mM ammonium bicarbonate solution and incubated for 20 minutes under agitation. Acetonitrile is then added so that a ratio of ammonium bicarbonate to acetonitrile of 1:1 is adjusted and incubation is carried out at room temperature for a further 15 minutes under agitation. After incubation has been completed, the samples are treated with ultrasound again for 2 minutes before the liquid is removed and combined with the liquid which had been removed previously. The remaining gel pieces are mixed with once their volume of a solution containing 5% formic acid and acetonitrile in the ratio 1:1 and incubated for 15 minutes at room temperature under agitation. The liquid is removed and combined with the liquid which had been removed previously. The incubation of the gel pieces in 5% formic acid/acetonitrile (ratio 1:1) is repeated and the liquid obtained is likewise added to the previously collected liquids. The combined supernatants contain the peptides to be sequenced and are concentrated to ca. 15 µl in the vacuum centrifuge (Speedvac) at 60° C. The peptides thus obtained can be stored at 20° C. until they are analysed using Q-TOF. Before the proteins can be sequenced in the mass analysis, they can be desalted using methods known to the person skilled in the art.

15. Transformation of Rice Plants

Rice plants were transformed in accordance with the methods described by Hiei et al. (1994, Plant Journal 6(2), 271-282).

16. Transformation of Potato Plants

Potato plants were transformed using *agrobacterium* as described by Rocha-Sosa et al. (EMBO J. 8, (1989), 23-29).

17. Determination of the Starch Phosphate Content

Determination of the C-6 Phosphate Content

In the starch the positions C2, C3 and C6 of the glucose units can be phosphorylated. 50 mg of starch was hydrolysed in 500 µl of 0.7 M HCl for 4 h at 95° C. to determine the C6-P content of the starch. The preparations were then centrifuged for 10 min at 15,500 g and the supernatants removed. From the supernatants 7 µl is mixed with 193 µl of imidazole buffer (100 mM imidazole, pH 7.4; 5 mM $MgCl_2$, 1 mM EDTA and 0.4 mM NAD). The measurement was made using a photometer at 340 mm. After a base absorption had been established, the enzyme reaction was started by adding 2 units of glucose-6-phosphate dehydrogenase (from *Leuconostoc mesenteroides*, Boehringer Mannheim). The change in absorption is directly proportional to the concentration of the G-6-P content of the starch.

b) Determination of the Total Phosphate Content

The total phosphate content was determined using the Ames method (Methods in Enzymology VIII, (1966), 115-118).

Approximately 50 mg of starch is mixed with 30 µl of ethanol magnesium nitrate solution and ashed for three hours at 500° C. in a muffle furnace. The residue is mixed with 300 µl of 0.5 M hydrochloric acid and incubated for 30 min at 60° C. An aliquot is then made up to 300 µl of 0.5 M hydrochloric acid, added to a mixture of 100 µl of 10% ascorbic acid and 600 µl of 0.42% ammonium molybdate in 2 M sulphuric acid and incubated for 20 min at 45° C.

c) Determination of the Content of C-6 Phosphate and C-3 Phosphate

To determine the content of phosphate bound in the C-6 position and in the C-3 position of the glucose molecules of an alpha-1,4-glucan, the glucans concerned can be separated using HPAE after total hydrolysis using the method specified under General Methods Item 13. The quantities of glucose-6-phosphate and glucose-3-phosphate can be determined by integrating the individual peak areas obtained after HPEA separation. The quantity of glucose-6-phosphate and glucose-3-phosphate in the samples to be studied can be determined by comparing the peak area for glucose-6-phosphate and glucose-3-phosphate obtained in the unknown samples, with the peak areas obtained after separation using HPAE with known quantities of glucose-6-phosphate and glucose-3-phosphate.

EXAMPLES

1. Isolation of a Protein from *Arabidopsis thaliana*, Which has Increased Binding Activity with Respect to P-Starch in Comparison with Non-Phosphorylated Starch a) Manufacture of Protein Extracts from *Arabidopsis thaliana*

Protein extracts were manufactured from approximately 7 g of leaves (fresh weight) of *Arabidopsis thaliana* (Ökotyp Columbia, Col-O) in accordance with the method described under Item 1, General Methods.

b) Isolation of Starch Granules from Leaves of Sex1-3 Mutants of *Arabidopsis thaliana*

Starch granules were isolated from approximately 20 g (fresh weight) of leaves of a sex1-3 mutant of *Arabidopsis thaliana* in accordance with the method described under Item 2, General Methods.

c) In Vitro Phosphorylation of Starch Isolated from a Sex1-3 Mutant of *Arabidopsis Thaliana* with Purified R1 Protein.

About 30 mg of non-phosphorylated starch isolated from a sex1-3 mutant of *Arabidopsis thaliana* was phosphorylated in accordance with the method described under Item 7, General Methods, by means of an R1 protein recombinantly expressed in *E. coli* and purified. The methods described in Ritte et al. (2002, PNAS 99, 7166-7171) were used for the expression of the R1 protein in *E. coli* and for the subsequent purification.

d) Isolation of Proteins, which Bind to P-Starch and/or Non-Phosphorylated Starch Protein extracts of *Arabidopsis thaliana*, obtained in accordance with Step a), were incubated and washed in a Preparation A with 50 mg of the in vitro phosphorylated starch manufactured in accordance with Step c) using the method described under Item 8 a), General Methods.

In a second Preparation B, protein extracts of *Arabidopsis thaliana*, obtained in accordance with Step a), were incubated and washed with 50 mg of the non-phosphorylated starch manufactured in accordance with Step b) using the method described under Item 8 a), General Methods.

Subsequently, the proteins bound to the P-starch of Preparation A and to the non-phosphorylated starch of Preparation B were dissolved in accordance with the method described under Item 8 b), General Methods.

In a third Preparation C, 50 mg of the in vitro phosphorylated starch manufactured in accordance with Step c) were incubated and washed using the method described under Item 8 a), General Methods. Preparation C contained no protein extracts however.

e) Separation of the Proteins Obtained in Accordance with Step D) by Means of Acrylamide Gel Electrophoresis The proteins of Preparations A, B and C obtained in Step d) were separated by means of a 9% acrylamide gel under denaturing conditions (SDS) using the method described under Item 9, General Methods, and subsequently stained with Coomassie Blue. The stained gel is shown in FIG. 1. It can be clearly seen that a protein, which has a molecular weight of ca. 130 kDa in denaturing acrylamide gel referred to a protein standard marker (Trace M), preferably binds to phosphorylated starch (Trace P) in comparison with non-phosphorylated starch (K).

The band of the protein with a molecular weight of ca. 130 kDa identified in Step e) was excised from the gel. The protein was subsequently released from the acrylamide as described under General Methods 10 b), digested with trypsin and the peptide masses obtained determined by means of MALD-TOF-MS. The so-called "fingerprint" obtained by MALDI-TOF-MS was compared with fingerprints of theoretically digested amino acid molecules in databases (Mascot: www.matrixscience.com/search_form_select.html; ProFound: 129.85.19.192/profound_bin/WebProFound.exe; PepSea: 195.41.108.38/PepSeaIntro.html). As such a fingerprint is very specific to a protein, it was possible to identify an amino acid molecule. Using the sequence of this amino acid molecule, it was possible to isolate a nucleic acid sequence from Arabidopsis thaliana coding for an OK1 protein. The protein identified using this method was designated as A.t.-OK1. After analysing the amino acid sequence from Arabidopsis thaliana, it was found that this deviates from the sequence present in the database (NP 198009, NCBI). The amino acid sequence shown in SEQ ID No 2 codes for the A.t.-OK1 protein. SEQ ID No 2 contains deviations when compared with the sequence in the database (Acc.: NP 198009.1, NCBI). The amino acids 519 to 523 (WRLCE) and 762 to 766 (VRARQ) contained in SEQ ID No 2 are not in the sequence, which is present in the database (ACC.: NP 198009.1). NP 198009.1). Compared to version 2 of the database sequence (Acc.: NP 198009.2) the amino acid sequence shown in SEQ ID NO 2 contains the additional amino acids 519 to 523 (WRLCE).

2. Cloning of a cDNA, which Codes for the Identified OK1 Protein

The A.t.-OK1 cDNA was isolated using reverse PCR using mRNA isolated from leaves of Arabidopsis thaliana. To do this, a cDNA Strand was synthesised by means of reverse transcriptase (SuperScript™ First-Strand Synthesis System for RT PCR, Invitrogen Prod. No.: 11904-018), which was then amplified using DNA polymerase (Expand High Fidelity PCR Systems, Roche Prod. No.: 1732641). The amplified product obtained from this PCR reaction was cloned into the vector pGEM®(-T (Invitrogen Prod. No.: A3600). The plasmid obtained is designated A.t.-OK1-pGEM®-T, the cDNA sequence coding for the A.t.-OK1 protein was determined and is shown under SEQ ID NO. 1.®

The sequence shown under SEQ ID NO 1 is not the same as the sequence, which is contained in the database. This has already been discussed for the amino acid sequence coding for an A.t.-OK1 protein.

Conditions Used for the Amplification of the cDNA Coding for the A.t.-OK1 Protein First Strand Synthesis:

The conditions and buffer specified by the manufacturer were used. In addition, the reaction preparation for the first strand synthesis contained the following substances:

```
3 µg    Total RNA (SEQ ID NO: 27)
5 µM    3'-primer
        (OK1rev1: 5'-GACTCAACCACATAACACACAAAGATC)

0.83 µM dNTP Mix
```

The reaction preparation was incubated for 5 minutes at 75° C. and subsequently cooled to room temperature.

The 1$^{st}$ strand buffer, RNase inhibitor and DTT were then added and incubated for 2 minutes at 42° C. before 1 µL, Superscript RT DNA polymerase was added and the reaction preparation incubated for 50 minutes at 42° C.

Conditions for the amplification of the first strand by means of PCR:

```
1 µL     of the reaction preparation of the
         first strand synthesis (SEQ ID NO: 28)
0.25 uM  3'Primer
         (OK1rev2: 5'- TGGTAACGAGGCAAATGCAGA)

(SEQ ID NO: 29)
0.25 uM  5'Primer
         (OK1fwd2: 5'-ATCTCTTATCACACCACCTCCAATG)
```

Reaction Conditions:

| Step 1 | 95° C. 2 min |
| Step 2 | 94° C. 20 sec |
| Step 3 | 62° C. 30 sec |
| Step 4 | 68° C. 4 minutes |
| Step 5 | 94° C. 20 sec |
| Step 6 | 56° C. 30 sec |
| Step 7 | 68° C. 4 minutes |
| Step 8 | 68° C. 10 minutes |

The reaction was first carried out in accordance with Steps 1 to 4. Ten repeats (cycles) were carried out between Step 4 and Step 2, the temperature of Step 3 being reduced by 0.67° C. after each cycle. This was subsequently followed by the reaction in accordance with the conditions specified in Steps 5 to 8. Twenty five repeats (cycles) were carried out between Step 7 and Step 5, the time of Step 7 being increased by 5 sec on each cycle. On completion of the reaction, the reaction was cooled to 4° C.

3. Manufacture of a Vector for the Recombinant Expression of cDNA of the OK1 Protein Following amplification by means of PCR by using the plasmid A.t.-OK1-pGEM® as a template using Gateway Technology (Invitrogen), the sequence coding the OK1 protein from Arabidopsis thaliana was first cloned in the vector pDONOR™ 201 (Invitrogen Prod. No.: 11798-014). Subsequently, the coding region of the OK1 protein from the vector obtained was cloned by sequence-specific recombination into the expression vector pDEST™17 (Invitrogen Prod. No.: 11803-014). The expression vector obtained is designated as A.t.-OK1-pDEST™1. The cloning resulted in a translational fusion of the cDNA coding for the A.t-OK1 protein with the nucleotides present in the expression vector PDEST™17 The nucleotides originating from the vector pDEST17™17, which are translationally fused with the cDNA coding the A.t.-OK1 protein, code for 21 amino acids. These 21 amino acids include, amongst others, the start codon (ATG) and a so-called His tag (6 histidine residues directly after one another). After translation of these translationally fused sequences, this results in an A.t.-OK1 protein, which has the additional 21 amino acids coded for by nucleotides originating from the vector at its N-terminus. The recombinant A.t.-OK1 protein resulting from this vector therefore contains 21 additional amino acids originating from the vector pDEST™17 at its N-terminus.

4. Heterologous Expression of the OK1 Protein in E. Coli

The expression vector A.t.-OK1-pDEST™17 obtained in accordance with Example 3 was transformed in the E. coli strain BL21 Star™ (DE3) (Invitrogen, Prod. No. C6010-03). A description of this expression system has already been given above (see Item 3, General Methods). Bacteria clones, containing the vector A.t.-OK1-pDEST™17, resulting from the transformation were first used to manufacture a preliminary culture, which was subsequently used for inoculating a main culture (see Item 3.c, General methods). The preliminary culture and the main culture were each incubated at 30° C. under agitation (250 rpm). When the main culture had reached an OD$_{600}$ of ca. 0.8, the expression of the recombinant A.t.-OK1 protein was induced by the addition of IPTG (isopropyl-beta-D-thiogalactopyranoside) until a final concentration of 1 mM was achieved. After the addition of IPTG, the main culture was incubated at 30° C. under agitation (250 rpm) until an OD$_{600}$ of ca. 1.8 was achieved. The main culture was then cooled for 30 minutes on ice before the cells of the main culture were separated from the culture medium by centrifugation (10 minutes at 4,000×g and 4° C.).

5. Purification of the Recombinantly Expressed OK1 Protein

The purification and concentration of the A.t.-OK1 protein from cells obtained in accordance with Example 4 was carried out using the method described under Item 4, General Methods.

6. Demonstration of Starch-Phosphorylating Activity of the OK1 Protein

The starch-phosphorylating activity of the A.t.-OK1 protein was demonstrated in accordance with the method described under Item 11, General Methods. In doing so, 5 µg of purified A.t.-OK1 protein manufactured in accordance with Example 5 was in each case incubated in a Preparation A with 5 mg of starch isolated from a sex1-3 mutant of *Arabidopsis thaliana* in accordance with Example 1b) and in a Preparation B with 5 mg of starch obtained by enzymatic phosphorylation in accordance with Example 1c), in each case in 500 µl of phosphorylation buffer containing 0.05 mM radioactively ($^{33}$P) labeled, randomised ATP (in total 1,130, 00 cpm, ca. 0.55 µCi) for 30 minutes at room temperature under agitation. A Preparation C which corresponded to the Preparation B but contained no OK1 protein but was otherwise treated, in the same manner as Preparations A and B was used as control. For all the preparations (A, B, C) two tests were carried out independently of one another in each case.

Figure 3:
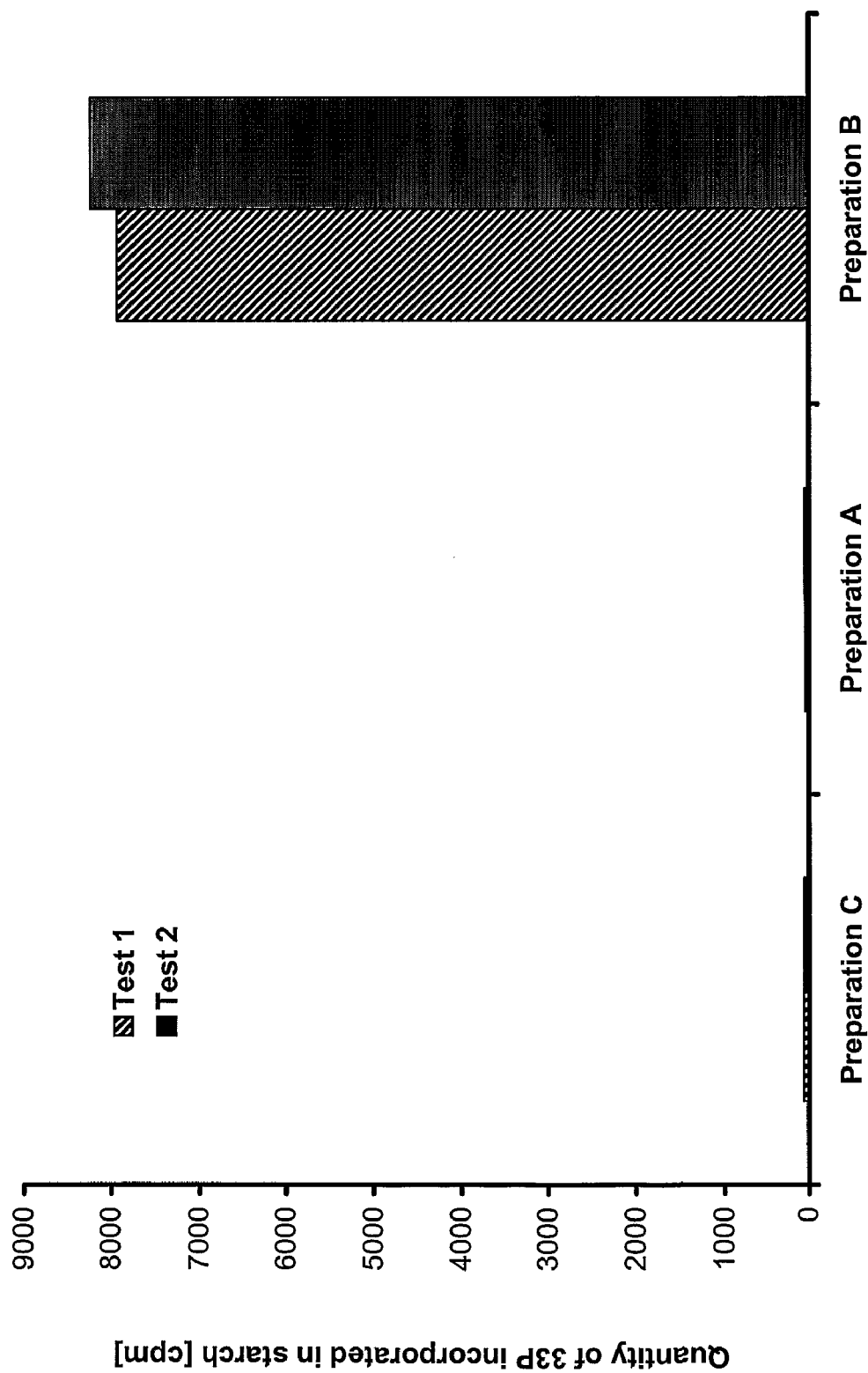
FIG. 3: Demonstration of the starch-phosphorylating activity of an OK1 protein (see Example 6). OK1 protein was incubated with non-phosphorylated starch isolated from leaves of an *Arabidopsis thaliana* sex1-3 mutant (Preparation A) and starch isolated from leaves of an *Arabidopsis thaliana* sex1-3 mutant, which was phosphorylated retrospectively in vitro with an R1 protein (Preparation B). Preparation C is the Same as Preparation B, Except that this Preparation C was incubated without OK1 protein. Two independent tests were carried out for each preparation (A, B, C) (Test 1 and Test 2). The respective amounts are shown, measured in cpm (counts per minute), on $^{33}$P labeled phosphate, which was introduced into non-phosphorylated starch (Preparation A) and phosphorylated starch (Preparation B).
Figure 4:
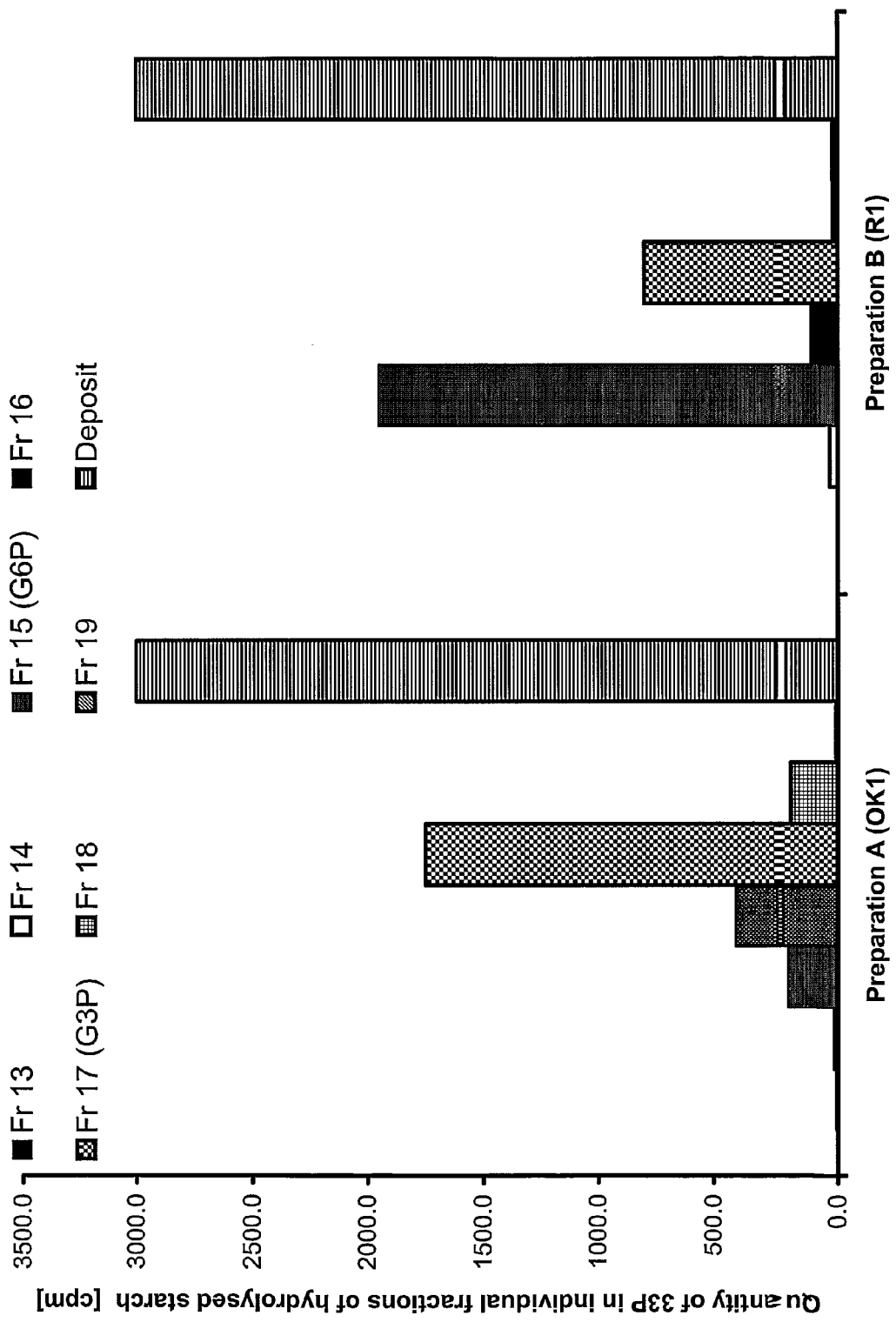
FIG. 4: Comparison of the C-atom positions of glucose molecules of the starch, which was phosphorylated from an R1 protein and an OK1 protein respectively (see Example 9). OK1 protein (Preparation A) was incubated in the presence of ATP labeled with $^{33}$P with starch isolated from leaves of an *Arabidopsis thaliana* sex1-3 mutant, which was phosphorylated retrospectively in vitro with an R1 protein.). R1 protein (preparation B) was incubated in the presence of ATP labeled with $^{33}$P with starch isolated from leaves of an *Arabidopsis thaliana* sex1-3 mutant. After incubation had been completed, a total hydrolysis of the starch was carried out and the hydrolysis products obtained were separated using HPAE chromatography. As standard, glucose-6-phosphate and glucose-3-phosphate were added to the hydrolysis products before separation. The hydrolysis products separated by means of HPAE chromatography were collected in individual fractions. The added glucose-6-phosphate eluted with fraction 15 and the added glucose-3-phosphate with fraction 17. The fractions obtained were subsequently investigated for the presence of radioactively labeled phosphate. The amount of $^{33}$P labeled phosphate measured in the individual fractions, measured in cpm (counts per minute), which was introduced into the hydrolysis products of the phosphorylated starch by the OK1 protein or the R1 protein, is shown graphically.

Using a scintillation counter, the starches from Preparations A, B, and C were investigated for the presence of radioactively labeled phosphate (see Item 11 b), General Methods). The results are shown in Table 1 and in FIG. 3.

TABLE 1

Demonstration of starch-phosphorylating activity of the OK1 protein

|  | Measured radioactivity [cpm] | |
| --- | --- | --- |
|  | Test 1 | Test 2 |
| Preparation A (non-phosphorylated starch + OK1) | 42 | 47 |
| Preparation B (phosphorylated starch + OK1) | 7921 | 8226 |
| Preparation C (phosphorylated starch without protein) | 56 | 53 |

From the results obtained, it can be seen that the OK1 protein does not transfer phosphate groups from ATP to starch when non-phosphorylated starch is provided as a substrate, as the quota of phosphate groups transferred to non-phosphorylated starch by means of an OK1 protein, measured in cpm, does not exceed the quota of radioactively labeled phosphate groups in Preparation C (control). If, on the other hand, P-starch is provided as a substrate, the quota of radioactive phosphate groups, measured in cpm, which are transferred from ATP to P-starch, is significantly higher. From this, it can be seen that the OK1 protein requires P-starch as a substrate and that non-phosphorylated starch is not accepted as a substrate by the OK1 protein.

If the test described above is carried out with ATP specifically labeled in the gamma position with $^{33}$P, then it is not possible to establish any incorporation of radioactively labeled phosphate in the starch. From this, it can be seen that the beta phosphate residue of ATP is transferred from an OK1 protein to starch. The results of such a test are shown.

7. Demonstration of Autophosphorylation

Autophosphorylation of the A.t.-OK1 protein was demonstrated by means of the methods described above (see Item 12, General Methods). Here, 50 µg of purified A.t.-OK1 protein were incubated with radioactively labeled, randomised ATP in 220 µl of phosphorylation buffer (see above, Item 12 d), General Methods) at room temperature for 60 minutes under agitation. Subsequently, 100 µl in each case was removed from the incubation preparations and transferred to four fresh reaction vessels. In reaction vessel 1, the reaction was stopped by the addition of 40 µl 0.11 M EDTA. Reaction vessel 2 was incubated at 95° C. for 5 minutes. HCl was added to reaction vessel 3 up to a final concentration of 0.5 M, and NaOH was added to reaction vessel 4 up to a final concentration of 0.5 M. Reaction vessels 3 and 4 were each incubated for 25 minutes at 30° C. Subsequently, 50 µl in each case was removed from reaction vessels 1, 2, 3 and 4, mixed with SDS test buffer and separated by means of SDS acrylamide gel electrophoresis (7.5% acrylamide gel). For this purpose, samples from the reaction vessels were applied to each of two identical acrylamide gels. One of the gels obtained on completion of electrophoresis was subjected to autoradiography, while the second gel was stained with Coomassie Blue.

Figure 2:
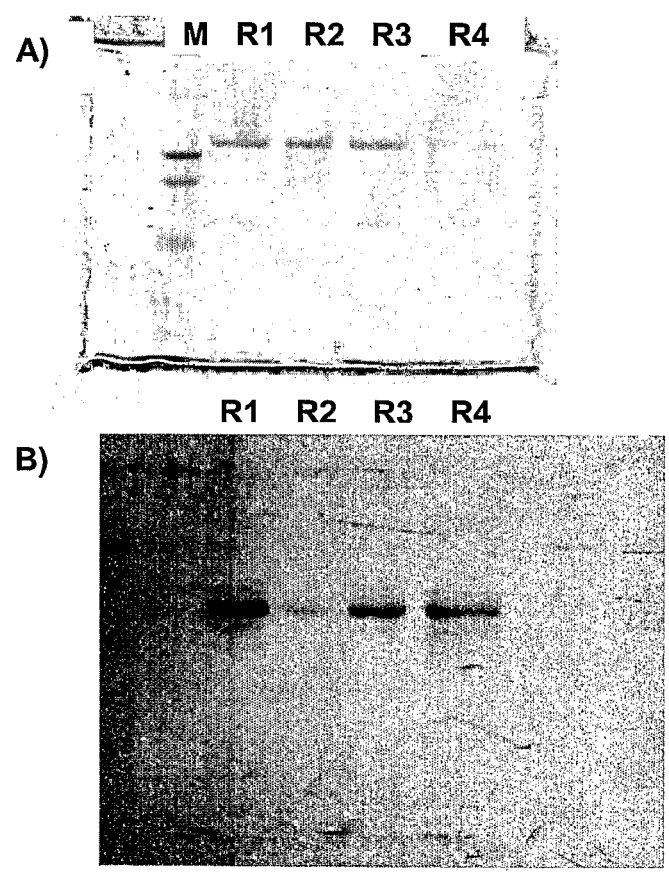
FIG. 2: Demonstration of the autophosphorylating activity of the OK1 protein.

In the gel stained with Coomassie Blue (see FIG. 2A)), it can be clearly seen that treatment with 0.5 M NaOH leads to degradation of the OK1 protein. The OK1 protein must therefore be described as unstable towards NaOH. Incubations at 30° C., 95° C. and with 0.5 M HCl show that the OK1 protein is relatively stable under the stated incubation conditions. This can be concluded from the fact that, under these incubation conditions, in each case approximately the same amounts of OK1 protein can be demonstrated in the gel concerned after staining with Coomassie Blue.

In the autoradiography (see FIG. 2B)), it can be seen by comparison with the phosphorylated OK1 protein incubated at 30° C. that an incubation of the phosphorylated OK1 protein at 95° C. leads to a significant reduction in the phosphate, which has bound to the OK1 protein. The binding between the phosphate residue and an amino acid of the OK1 protein must therefore be described as heat-unstable. Furthermore, a slight reduction of the phosphate bound to the OK1 protein can also be seen for the incubation with 0.5 M HCl and 0.5 M NaOH in comparison with phosphorylated OK1 protein incubated at 30° C. If the fact is taken into account that the quantity of OK1 protein in the autoradiography after treatment with 0.5 M NaOH is significantly less than in the samples treated with heat and acid on account of the instability of the OK1 protein towards NaOH, then it can be concluded that the binding between the phosphate residue and an amino acid of the OK1 protein will be relatively stable with respect to bases. As the sample treated with acid contains approximately the same amounts of protein as the samples incubated at 30° C. and at 95° C., and yet has a significantly lower signal in the autoradiography than the sample treated at 30° C., it must be assumed that acid incubation conditions also split the bond between a phosphate residue and an amino acid of the OK1 protein to a certain extent. An instability of the binding between a phosphate residue and an amino acid of the OK1 protein could therefore also be established in the tests carried out. At the same time, the instability with respect to acids is significantly less labeled than the instability with respect to heat.

The binding between the amino acid histidine and phosphate are heat-unstable, acid-unstable but base-stable (Rosenberg, 1996, Protein Analysis and Purification, Birkhäuser, Boston, 242-244). The results described above are therefore an indication that a phosphohistidine is produced by the autophosphorylation of an OK1 protein.

Figure 5:
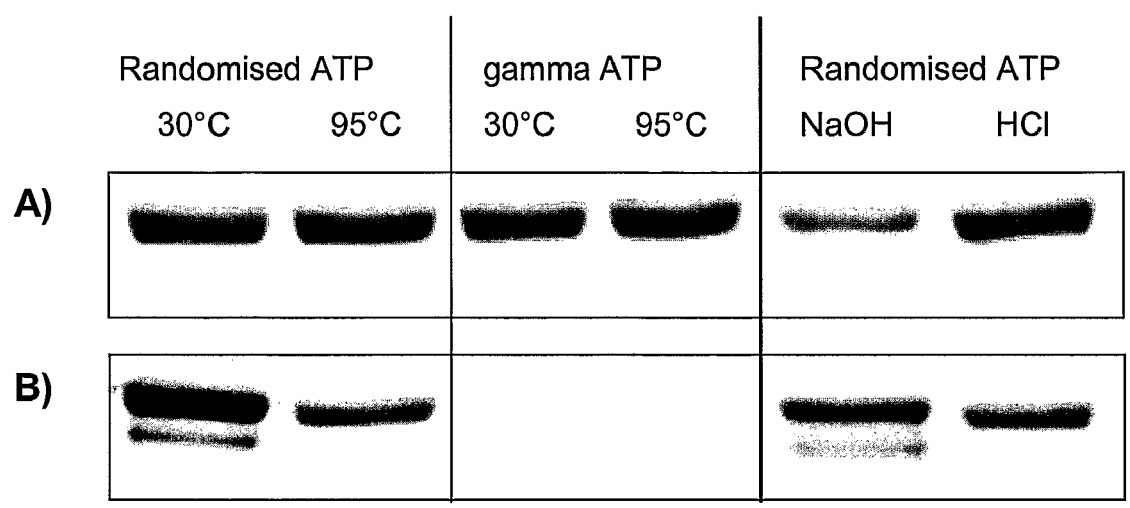
FIG. 5 Demonstration of the autophosphorylation of the OK1 protein.
Figure 6:
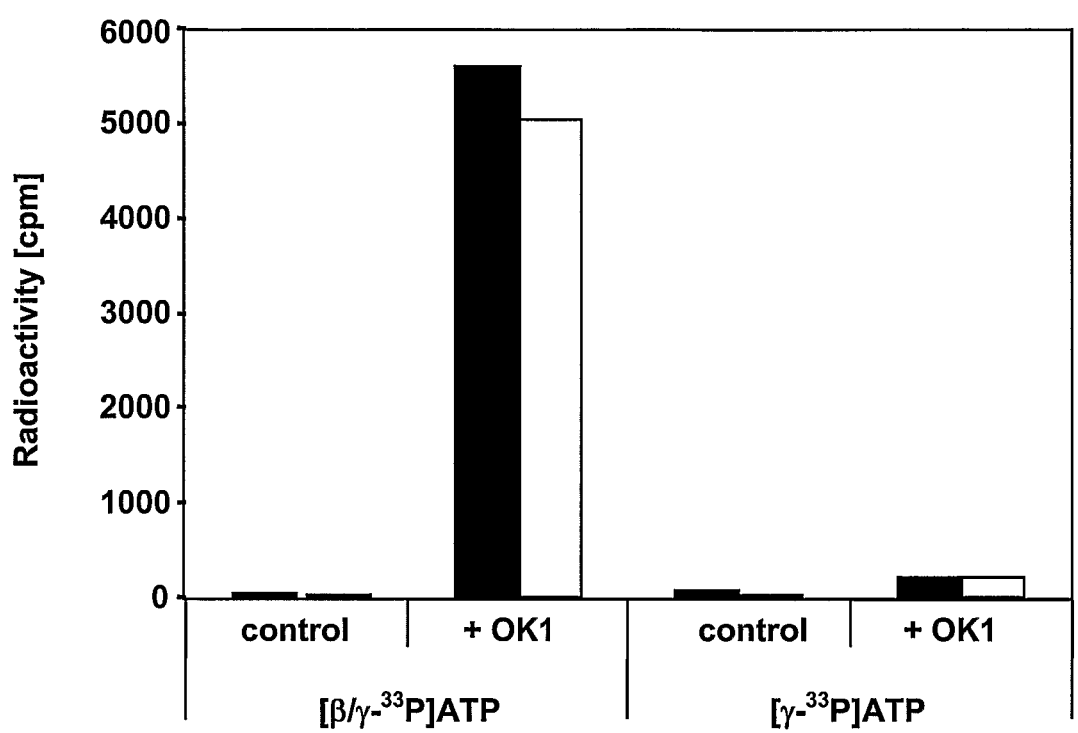
FIG. 6 Demonstration of the transfer of the beta-phosphate residue of ATP to starch in a reaction catalysed by an OK1 protein. Either ATP specifically labeled with $^{33}$P in the gamma position or randomised $^{33}$P ATP was used to phosphorylate starch, which had been phosphorylated in vitro by means of an R1 protein and isolated from leaves of an *Arabidopsis thaliana* sex1-3 mutant, by means of an OK1 protein. No OK1 protein was added in any of the experiments designated as "control". Each preparation was tested twice, independently of one another. The results of both tests are shown.

If recombinantly expressed OK1 protein is incubated as described above with ATP specifically labeled with $^{33}$P in the gamma position, no autophosphorylation can be established. FIG. 5 A) shows the amount of protein which can be detected in the respective reaction preparation by means of Western Blot analysis after the relevant incubation steps. FIG. 5 B) shows an autoradiography of protein from the individual reaction preparations. It can be seen that, when ATP specifically labeled in the gamma position is used, no autophosphorylation of the OK1 protein can be demonstrated, whereas, when randomised ATP is used, autophosphorylation can be demonstrated. This means that when an OK1 protein is autophosphorylated, the phosphate residue of the beta position of the ATP is covalently bound to an amino acid of the OK1 protein.

8. Demonstration of the C-Atom Positions, Which are Phosphorylated by an OK1 Protein, of the Glucose Molecules of Starch a) Manufacture of Phosphorylated Starch Phosphorylated starch was manufactured in accordance with Item 7, General Methods. To do this, 5 mg of non-phosphorylated starch, isolated from leaves of a sex1-3 mutant of *Arabidopsis thaliana* was used in a Preparation A with 25 µg of purified A.t.-OK1 protein and, in a second Preparation B, 5 mg of in vitro phosphorylated starch originally isolated from leaves of a sex1-3 mutant of *Arabidopsis thaliana* was used with 5 µg of purified R1 protein. The reaction was carried out in 500 µl of phosphorylation buffer in each case, which, in each case contained $^{33}$P labeled ATP (ca. $2.5 \times 10^6$ cpm), by incubating at room temperature for 1 hour under agitation. In addition, a control preparation was used, which contained 5 mg of starch isolated from leaves of a sex1-3 mutant of *Arabidopsis thaliana* and the said phosphorylation buffer, but no protein. The control preparation was treated in exactly the same way as preparations A and B. The individual reactions were stopped by adding 125 µl of 10% SDS in each case and washing was carried out once with 2% SDS, five times with 2 mM ATP and twice with $H_2O$, using 900 µl in each case. Centrifugation was carried out after each washing step (2 minutes in an Eppendorf table centrifuge at 13,000 rpm in each case). The starch pellets obtained were resuspended 1 ml $H_2O$ in each case and 100 µl of each preparation was mixed after the addition of 3 ml of scintillation cocktail (Ready Safe™, BECKMANN) and subsequently measured using a scintillation counter (LS 6500 Multi-Purpose Scintillation Counter, BECKMANN COULTER™).

The measurement gave the following results:

| | | |
|---|---|---|
| Control: | 63 cpm/100 µL | 630 cpm/1000 µl |
| Preparation A (OK1): | 1351 cpm/100 µl | 13512 cpm/1000 µl |
| Preparation B (R1): | 3853 cpm/100 µl | 38526 cpm/1000 µl | b) Total hydrolysis of the P-starch

The suspensions of Preparations A, B and C obtained in accordance with Step a) were centrifuged again (5 minutes in an Eppendorf table centrifuge at 13,000 rpm), the pellets obtained resuspended in 90 µl 0.7 M HCl (Baker, for analysis) and subsequently incubated for 2 hours at 95° C. Preparations A, B and C were then centrifuged again (5 minutes in an Eppendorf table centrifuge at 13,000 rpm), and the supernatant transferred to a new reaction vessel. Sedimented residues of the preparations were resuspended in 100 ml $H_2O$ in each case and after the addition of 3 ml of scintillation cocktail (Ready Safe™, BECKMANN) were measured using a scintillation counter (LS 6500 Multi-Purpose Scintillation Counter, BECKMANN COULTER™). Significant amounts of radioactivity could not be demonstrated in any of the residues, which means that all the hydrolysis products labeled with radioactive phosphate are located in the supernatant.

This was followed by neutralisation of the individual supernatants containing the hydrolysis products by the addition in each case of 30 µl 2 M NaOH (the amount of NaOH required for neutralisation was tested out in advance on blank samples). The neutralised hydrolysis products were placed on a 10 kDa Microcon filter, which had previously been rinsed twice with 200 µl $H_2O$ in each case, and centrifuged for ca. 25 minutes at 12,000 rpm in an Eppendorf table centrifuge. 10 µl was taken from the filtrate obtained (ca. 120 µl in each case) and, after the addition of 3 ml of scintillation cocktail (Ready Safe™, BECKMANN), were measured using a scintillation counter (LS 6500 Multi-Purpose Scintillation Counter, BECKMANN COULTER™). The determination of the activity present in the individual preparations gave the following results:

| | | | |
|---|---|---|---|
| Preparation A (OK1): | 934 cpm/10 µl | 11,208 cpm/120 µl | 93 cpm/µl |
| Preparation B (R1): | 2518 cpm/10 µl | 30,216 cpm/120 µl | 252 cpm/µl | c) Separation of the Hydrolysis Products

The hydrolysis products obtained in accordance with Step b) were separated by means of HPAE using a Dionex system under the conditions stated above (see General Methods, Item 13 c)). The samples for separating the filtered supernatants of Preparations A and B obtained in accordance with Step b) were composed as follows:

Preparation A (OK1): 43 µl of the supernatant of Preparation A obtained in accordance with Step b) (equivalent to ca. 4,000 cpm), 32 µl $H_2O$, 2.5 µl 2.5 mM glucose-6-phosphate and 2.5 µl 5 mM glucose-3-phosphate (Σ Volume=80 µl).

Preparation B (R1): 16 µl of the supernatant of Preparation B obtained in accordance with Step b) (equivalent to ca. 4,000 cpm), 59 µl $H_2O$, 2.5 µl 2.5 mM glucose-6-phosphate and 2.5 µl 5 mM glucose-3-phosphate (E Volume=80 µl).

In each case 60 µl, containing ca. 3,000 cpm, of the corresponding samples was injected for separation using HPAE. The HPAE was carried out in accordance with the conditions specified under Point 23 c). After passing through the HPAE column, the elution buffer was collected in fractions, each of 1 ml. Collection of the fractions was begun 10 minutes after injecting the sample. Based on the signal received from the PAD detector used, the elution of glucose-6-phosphate was assigned to fraction 15 and the elution of glucose-3-phosphate to fraction 17. In each case, 500 µl of the individual fractions were mixed with 3 ml of scintillation cocktail (Ready Safe™, BECKMANN) and subsequently measured using a scintillation counter (LS 6500 Multi-Purpose Scintillation Counter, BECKMANN COULTER™). The following measurements were obtained for the individual fractions:

TABLE 4

Measured amounts of radioactivity [cpm] in individual fractions of hydrolysis products obtained by hydrolysis of starch phosphorylated by means of an OK1 protein or R1 protein.

| | Total cpm per fraction | |
|---|---|---|
| | Preparation A (OK1) | Preparation B (R1) |
| Fr 13 | 8.7 | 3.3 |
| Fr 14 | 13.1 | 32.2 |
| Fr 15 (G6P) | 207.3 | 1952.8 |
| Fr 16 | 3998 | 112.3 |
| Fr 17 (G3P) | 1749.2 | 801.6 |

TABLE 4-continued

Measured amounts of radioactivity [cpm] in individual fractions of hydrolysis products obtained by hydrolysis of starch phosphorylated by means of an OK1 protein or R1 protein.

| | Total cpm per fraction | |
| --- | --- | --- |
| | Preparation A (OK1) | Preparation B (R1) |
| Fr 18 | 196.7 | 17.3 |
| Fr 19 | 6.7 | 18.9 |
| Total | 2581.5 | 2938.3 |
| Deposit | 3000.0 | 3000.0 |
| Recovery | 86.0% | 97.9% |

The results are also shown graphically in FIG. 5.

After phosphorylation of starch catalysed by R1 protein, ca. 66% of the radioactively labeled phosphate, referred to the total measured radioactive phosphate in the analysed fractions, eluted after hydrolysing the starch with the fraction which contained glucose-6-phosphate as standard, and ca. 27% with the fraction which contained glucose-3-phosphate as standard. After phosphorylation of starch catalysed by OK1 protein, ca. 67% of the radioactively labeled phosphate, referred to the total measured radioactive phosphate in the analysed fractions, eluted after hydrolysing the starch with the fraction which contained glucose-3-phosphate as standard, and ca. 8% with the fraction which contained glucose-6-phosphate as standard. From this, it can be concluded that glucose molecules of the starch of R1 proteins are preferably phosphorylated in the C-6 position, whereas from OK1 proteins glucose molecules of the starch are preferably phosphorylated in the C-3 position.

9. Identification of an OK1 Protein in Rice

Using the methods described under Items 1 to 13, General Methods, it was also possible to identify a protein from *Oryza sativa* (variety M202), which transfers a phosphate residue from ATP to P-starch. The protein was designated as O.s.-OK1. Non-phosphorylated starch is not used by the O.s.-OK1 protein as a substrate, i.e. the O.s.-OK1 protein also does need P-starch as a substrate. The nucleic acid sequence defining the identified O.s.-OK1 protein is shown under SEQ ID NO 3 and the amino acid sequence coding for the O.s.-OK1 protein is shown under SEQ ID NO. 4. The amino acid sequence coding for the O.s.-OK1 protein shown under SEQ ID NO 4 has an identity of 57% with the amino acid sequence coding for the A.t.-OK1 protein shown under SEQ ID NO 2. The nucleic acid sequence coding for the O.s.-OK1 protein shown under SEQ ID NO 3 has an identity of 61% with the nucleic acid sequence coding for the A.t.-OK1 protein shown under SEQ ID NO 1.

Manufacture of the plasmid pMI50 containing the nucleic acid sequence coding for an OK1 protein from *Oryza sativa*

The vector pMI50 contains a DNA fragment, which codes for the complete OK1 protein from rice of the variety M202.

The amplification of the DNA from rice was carried out in five sub-steps.

The part of the open reading frame from position -11 to position 288 of the sequence specified under SEQ ID NO: 3 was amplified using reverse transcriptase and polymerase chain reaction using the synthetic oligonucleotides Os_ok1-R9 (GGAACCGATAATGCCTACATGCTC) (SEQ ID NO: 30) and Os_ok1-F6 (AAAACTCGAGGAGGATCAAT-GACGTCGCTGCGGCCCCTC) (SEQ ID NO: 31) as a primer on RNA of immature rice seeds. The amplified DNA fragment was cloned into the vector pCR2.1 (Invitrogen catalogue number K2020-20). The plasmid obtained was designated as pML123.

The part of the open reading frame from position 250 to position 949 of the sequence specified under SEQ ID NO: 3 was amplified using reverse transcriptase and polymerase chain reaction using the synthetic oligonucleotides Os_ok1-F4 (CCAGGTTAAGITTGGTGAGCA) (SEQ ID NO: 32) and Os_ok1-R6 (CAAAGCACGATATCTGACCTGT) (SEQ ID NO: 33) as a primer on RNA of immature rice seeds. The amplified DNA fragment was cloned into the vector pCR2.1 (Invitrogen catalogue number K2020-20). The plasmid obtained was designated as pML120.

The part of the open reading frame from position 839 to position 1761 of the sequence specified under SEQ ID NO: 3 was amplified using reverse transcriptase and polymerase chain reaction using the synthetic oligonucleotides Os_ok1-F7 (TTGTTCGCGGGATATTGTCAGA) (SEQ ID NO: 34) and Os_ok1-R7 (GACAAGGGCATCAAGAGTAGTATC) (SEQ ID NO: 35) as a primer on RNA of immature rice seeds. The amplified DNA fragment was cloned into the vector pCR2.1 (Invitrogen catalogue number K2020-20). The plasmid obtained was designated as pML121.

The part of the open reading frame from position 1571 to position 3241 of the sequence specified under SEQ ID NO: 3 was amplified using reverse transcriptase and polymerase chain reaction using the synthetic oligonucleotides Os_ok1-F8 (ATGATGCGCCTGATAATGCT) (SEQ ID NO: 36) and Os_ok1-R4 (GGCAAACAGTATGAAGCACGA) (SEQ ID NO: 37) as a primer on RNA of immature rice seeds. The amplified DNA fragment was cloned into the vector pCR2.1 (Invitrogen catalogue number K2020-20). The plasmid obtained was designated as pML119.

The part of the open reading frame from position 2777 to position 3621 was amplified using polymerase chain reaction using the synthetic oligonucleotides Os_ok1-F3 (CATTTG-GATCAATGGAGGATG) (SEQ ID NO: 38) and Os_ok1-R2 (CTATGGCTGTGGCCTGCTTTGCA) (SEQ ID NO: 39) as a primer on genomic DNA of rice. The amplified DNA fragment was cloned into the vector pCR2.1 (Invitrogen catalogue number K2020-20). The plasmid obtained was designated as pML122.

The cloning together of the sub-parts of the open reading frame of OK1 was carried out as follows.

A 700 base pair long ApaI fragment of pML120, containing part of the open reading frame of OK1, was cloned in the ApaI site of pML121. The plasmid obtained was designated as pMI47.

A 960 base pair long fragment containing the regions of the vectors from pML120 and pML123 coding for OK1 was amplified by means of polymerase chain reaction. In doing so, the primers Os_OK1-F4 (see above) and Os_OK1-R9 (see above), each in a concentration of 50 nm, and the primers Os_OK1-F6 and Os_OK1-R6, each in a concentration of 500 nm, were used. The amplified DNA fragment was cloned into the vector pCR2.1 (Invitrogen catalogue number K2020-20). The plasmid obtained was designated as pMI44.

An 845 base pair long fragment of pML122 was reamplified for introducing a XhoI site after the stop codon with the primers Os ok1-F3 (see above) and Os_ok1-R2Xho (AAAACTCGAGCTATGGCTGTGGCCTGCTTTGCA) (SEQ ID NO: 40) and cloned into the vector pCR2.1 (Invitrogen catalogue number K2020-20). The plasmid obtained was designated as t pMI45.

A 1671 base pair long fragment containing part of the open reading frame of OK1 was obtained from pML119 by digesting with the restriction enzymes SpeI and PstI. The fragment was cloned into pBluescript II SK+ (Genbank Acc.: X52328). The plasmid obtained was designated as pMI46.

A 1706 base pair long fragment containing part of the open reading frame of OK1 was excised with the restriction enzymes SpeI and XhoI from pMI46 and cloned into the vector pMI45, which had been excised with the same restriction enzymes. The plasmid obtained was designated as pMI47.

A 146 base pair long fragment containing part of the open reading frame of OK1 was excised with the restriction enzymes AflIII/NotI from pMI43 and cloned into the vector pMI44, which had been excised with the same restriction enzymes. The plasmid obtained was designated as pMI49.

A 1657 base pair long fragment containing part of the open reading frame of OK1 was excised with the restriction enzymes NotI and NarI from the vector pMI49 and cloned into the vector pMI47, which had been excised with the same restriction enzymes. The plasmid obtained was designated as pMI50 and contains the whole coding region of the OK1 protein identified in rice.

10. Identification of Further OK1 Proteins From Various Plant Species

Using the methods described under Items 1 to 13, General Methods, proteins which transfer a phosphate residue from ATP to P-starch were also identified in barley (*Hordeum vulgare*), potato (*Solanum tuberosum*), wheat (*Triticum aestivum*) and millet (*Sorghum bicolor*). Non-phosphorylated starch is not used as substrate by these proteins, i.e., these proteins require P-starch as substrate.

The proteins were isolated using the method described under Item 14, General Methods, digested with trypsin, dissolved out of the gel and sequenced using Q-TOF-MS-MS. Using the peptide sequences obtained, it was possible to determine EST nucleic acid sequences which code for the relevant Oki proteins from barley, potato, wheat or millet by means of database comparisons (blast searches).

The nucleic acid sequence shown in SEQ ID NO 9 codes for a part of an OK1 protein from barley and was traced under "Accession" No.: TC117610 in the TIGR (tigrblast.tigr.org/tgi/) database by means of a database comparison (blast search). Those peptides which were obtained by sequencing the OK1 protein isolated from barley using Q-TOF-MS-MS and were used to identify the EST nucleic acid sequence shown under SEQ ID NO 9, are specified in SEQ ID NO 6, SEQ ID NO 7 and SEQ ID NO 8. The amino acid sequence shown in SEQ ID NO 10 codes for a part of an OK1 protein from barley and can he derived from the nucleic acid sequence shown in SEQ ID NO 10.

The nucleic acid sequence shown in SEQ ID NO 15 codes for a part of an OK1 protein from potato and was found under "Accession" No.: BF054632 in the TIGR (tigrblast.tigr.org/tgi/) database by means of a database comparison (blast search). Those peptides which were obtained by sequencing the OK1 protein isolated from potato using Q-TOF-MS-MS and were used to identify the EST nucleic acid sequence shown under SEQ ID NO 15, are specified in SEQ ID NO 11, SEQ ID NO 12, SEQ ID NO 13 and SEQ ID NO 14. The amino acid sequence shown in SEQ ID NO 16 codes for a part of an OK1 protein from potato and can be derived from the nucleic acid sequence shown in SEQ ID NO 15.

The nucleic acid sequence shown in SEQ ID NO 21 codes for a part of an OK1 protein from millet and was found under "Accession" No.: TC77219 in the TIGR (tigrblast.tigr.org/tgi/) database by means of a database comparison (blast search). Those peptides which were obtained by sequencing the OK1 protein isolated from millet using Q-TOF-MS-MS and were used to identify the EST nucleic acid sequence shown under SEQ ID NO 21, are specified in SEQ ID NO 17, SEQ ID NO 18, SEQ ID NO 19 and SEQ ID NO 20. The amino acid sequence shown in SEQ ID NO 22 codes for a part of an OK1 protein from millet and can be derived from the nucleic acid sequence shown in SEQ ID NO 21.

The nucleic acid sequence shown in SEQ ID NO 25 codes for a part of an OK1 protein from wheat and was found under "Accession" No.: CA74319 in the TIGR (tigrblast.tigr.org/tgi) database by means of a database comparison (blast search). Those peptides which were obtained by sequencing the OK1 protein isolated from wheat using Q-TOF-MS-MS and were used to identify the EST nucleic acid sequence shown under SEQ ID NO 25, are specified in SEQ ID NO 23 and SEQ ID NO 24. The amino acid sequence shown in SEQ ID NO 26 codes for a part of an OK1 protein from wheat and can be derived from the nucleic acid sequence shown in SEQ ID NO 25.

The following settings were selected to carry out the database comparisons:

| Program: | tblastn |
|---|---|
| Matrix: | blosum62 |
| Expect: | 100 |
| Echofilter: | disabled |
| Descriptions: | 20 |

All other settings read "default".

11. Manufacture of an Antibody, which Specifically Recognises an OK1 Protein

As an antigen, ca. 100 μg of purified A.t.-OK1 protein was separated by means of SDS gel electrophoresis, the protein bands containing the A.t.-OK1 protein excised and sent to the company EUROGENTEC S.A. (Belgium), which carried out the manufacture of the antibody under contract. First, the preimmune sera of rabbits were investigated to see whether they would already recognise a protein from an A.t. total extract before immunisation with recombinant OK1. The preimmune sera of two rabbits recognised no proteins in the range 100-150 kDa and were thus chosen for immunisation. Four injections of 100 μg of protein (day 0, 14, 28, 56) were given to each rabbit. Four blood samples were taken from each rabbit: (day 38, day 66, clay 87 and the final bleeding). Serum obtained after the first bleeding, already showed a specific reaction with OK1 antigen in Western blot. However, in all further tests, the final bleeding of a rabbit was used 12. Manufacture of Transgenic Rice Plants Which Have an Elevated or a Reduced Activity of an OK1 Protein a) Manufacture of the Plasmid pGlo-A.t.-OK1

The plasmid pIR94 was obtained by amplifying the promoter of the globulin gene from rice by means of a polymerase chain reaction (30 ×20 sec 94 ° C., 20 sec 62 ° C., 1 min 68 ° C., 4 mM Mg2SO4) with the primers glb1-F2 (AAAACAATTGGCGCCTGGAGGGAGGAGA) (SEQ ID NO: 41) and glb1-R1 (AAAACAATTGATGATCAATCA-GACAATCACTAGAA) (SEQ ID NO: 42) on the genomic DNA of rice of the variety M202 with High Fidelity Taq Polymerase (Invitrogen, catalogue number 11304-011) and cloned into pCR2.1 (Invitrogen catalogue number K2020-20).

The plasmid pLR115 was obtained by cloning a synthetic piece of DNA consisting of the two oligonucleotides X1 (TGCAGGCTGCAGAGCTCCTAGGCTC-GAGTTAACACTAGTAAGCTTAATTAAGATAT CATT-TAC) (SEQ ID NO: 43) and X2 (AATTGTAAATGATATCT- TAATTAAGCTTACTAGTGTTAACTCGAGCCTAGGAG CTCT GCAGCCTGCA) (SEQ ID NO: 44) into the vector pGSV71 excised with SdaI and MunI.

The plasmid pIR115 obtained was excised with SdaI, the protruding 3'-ends smoothed with T4 DNA polymerase and a 197-base-pair HindIII/SphI fragment from pBinAR (Hofgen and Willmitzer, 1990, Plant Science 66, 221-230), smoothed by means of T4 DNA polymerase and containing the termination signal of the octopine synthase gene from *Agrobacterium tumefaciens*, was inserted. The plasmid obtained was designated as pIR96.

The plasmid pIR103 was obtained by cloning a 986-base-pair long DNA fragment from pIR94, containing the promoter of the globulin gene from rice, into the plasmid pIR96.

pGSV71 is a derivative of the plasmid pGSV7, which is derived from the intermediary vector pGSV1. pGSV1 is a derivative of pGSC1700 whose construction has been described by Cornelissen and Vanderwiele (Nucleic Acid Research 17, (1989), 19-25). pGSV1 was obtained from pGSC1700 by deletion of the carbenicillin resistance gene, as well as deletion of the T-DNA sequences of the TL-DNA region of the plasmid pTiB$_6$S3.

pGSV7 contains the replication origin of the plasmid pBR322 (Bolivar et al., Gene 2, (1977), 95-113) as well as the replication origin of the *Pseudomonas* plasmid pVS1 (Itoh et al., Plasmid 11, (1984), 206). pGSV7 also contains the selectable marker gene aadA, from the transposon Tn1331 from *Klebsiella pneumoniae*, which imparts resistance to the antibiotics spectinomycin and streptomycin (Tolmasky, Plasmid 24 (3), (1990), 218-226; Tolmasky and Crosa, Plasmid 29(1), (1993), 31-40)

The plasmid pGSV71 was obtained by cloning a chimeric bar gene between the border regions of pGSV7. The chimeric bar gene contains the promoter sequence of the cauliflower mosaic virus for initiation of the transcription (Odell et al., Nature 313, (1985), 180), the bar gene from *Streptomyces hygroscopicus* (Thompson et al., Embo J. 6, (1987), 2519-2523) and the 3'-untranslated region of the nopaline synthase gene of the T-DNA of pTiT37 for termination of the transcription and polyadenylation. The bar gene provides tolerance against the herbicide glufosinate ammonium.

A DNA fragment which contains the complete open reading frame of the OK1 protein from *Arabidopsis* was excised from the vector A.t.-OK1-pGEM-T and cloned into the vector pIR103. For this purpose the plasmid A.t.-OK1-pGEM-T was excised with the restriction enzyme Bsp120I, the ends smoothed with T4-DNA polymerase and subsequently excised with SalI. The DNA fragment coding for the OK1 protein from *Arabidopsis thaliana* was cloned into the vector pIR103 excised with Ecl13611 and XhoI. The plasmid obtained was designated as pGlo-A.t.-OK1.

b) Manufacture of a Construct for Inhibiting the OK1 Protein in Rice by Means of RNAi Technology The plasmid pML125, which was used for the transformation of rice plants, was obtained by specific recombination of the plasmids pML124 and pIR115 using the Gateway™ cloning system (Invitrogen).

pML124 was obtained by cloning a 359 base pair long DNA fragment of pML119 (see above, Example 9), containing part of the open reading frame which codes for the OK1 protein from rice, into the vector pENTR-1A (Invitrogen, product number 11813-011) excised with EcoRI.

The plasmid pIR87 was obtained by amplifying the intron 1 of the gene coding for alcohol hydrogenase from maize with the primers Adh(i)-1 (TTTTCTCGAGGTCCGCCT-TGTTTCTCCT) (SEQ ID NO: 45) and Adh(i)-2 (TTTTCTCGAGCTGCACGGGTCCAGGA) (SEQ ID NO: 46) on the genomic DNA of maize. The product of the polymerase chain reaction (30 ×30 sec 94 ° C., 30 sec 59 ° C., 1 min 72 ° C., 2.5 mM MgCl$_2$) was digested with the restriction enzyme XhoI and cloned into the vector pBluescript II SK+ (Genbank Acc.: X52328), which had been excised with the same enzyme.

A 986 base pair long DNA fragment from pIR94, containing the promoter of the globulin gene from rice, was cloned into the vector pIR96. The plasmid obtained was designated as pIR103.

The plasmid pIR107 was obtained by cloning the "RfA cassette" (see above) into the plasmid pIR103 excised with the restriction enzyme EcoRV.

A 540 base pair long fragment containing the intron 1 of the gene coding for alcohol dehydrogenase from maize was excised from the plasmid pIR87 with the restriction enzyme XhoI and cloned into the plasmid pIR107 likewise excised with XhoI. The plasmid obtained was designated as piR114. The plasmid pIR115 was obtained by cloning the "RfA cassette" (see above) into the plasmid piR114 excised with Ec/13611.

c) Transformation of Rice Plants

Rice plants (variety M202) were transformed using *Agrobacterium* (containing either the plasmid pGlo-A.t.-OK1 or the plasmid pML125) using the method described in Hiei et al. (1994, Plant Journal 6(2), 271-282).

d) Analysis of the Transgenic Rice Plants which Expressed the A.t.-OK1 Protein and the Starch Synthesised by These Plants Plants transformed with the plasmid pGlo-A.t.-OK1 which exhibited an expression of the heterologous A.t.-OK1 protein were identified by means of a Northern Blot analysis.

Plants which exhibited a detectable quantity of mRNA coding for A.t.-OK1 protein were cultivated in the greenhouse. Grains of these plants were harvested. Starch from these grains showed an elevated content of phosphate covalently bound to the starch concerned.

e) Analysis of the Transgenic Rice Plants in Which the Expression of the Endogenous OK1 Protein was Repressed by Means of RNAi Technology and the Starch Synthesised From These Plants Rice plants which were transformed with the plasmid pML125 and exhibited a reduced expression of the endogenous mRNA coding for the OK1 protein were identified by means of Northern Blot analysis.

13. Manufacture of Transgenic Potato Plants Which Have an Elevated or a Reduced Activity of an OK1 Protein a) Manufacture of the Plasmid pBinB33-Hyg Starting from the plasmid pBinB33, the EcoRI-HindIII fragment including the B33 promoter, a part of the polylinker, and the ocs terminator were excised and ligated into the correspondingly excised vector pBIB-Hyg (Becker, 1990, Nucl. Acids Res. 18, 203). Acids Res. 18, 203).

The plasmid pBinB33 was obtained by ligating the promoter of the patatin gene B33 from *Solanum tuberosum* (Rocha-Sosa et al., 1989) as a DraI fragment (nucleotide-1512-+14) into the vector pUC19 excised with SstI, the ends of which had been smoothed using the T4 DNA polymerase. This resulted in the plasmid pUC19-B33. The B33 promoter was excised from this plasmid with EcoRI and SmaI and ligated into the correspondingly excised vector pBinAR (Höfgen and Willmitzer, 1990, Plant Science 66, 221-230). This resulted in the plant expression vector pBinB33.

b) Manufacture of the Vector A.t.-OK1-pBinB33-Hyg

The coding sequence of the A.t.-OK1 protein was excised with the restriction endonucleases Bsp1201 and SalI from the plasmid OK1-pGEM and ligated into the vector pBinB33-

Hyg excised with SmaI and SalI. The plasmid obtained was designated as A.t.-OK1-pBinB33-Hyg.

c) Transformation of Potato Plants

*Agrobacterium tumefaciens* (strain GV2260) was transformed with the plasmid A.t.-OK1-pBinB33-Hyg. Potato plants of the Désirée variety were then transformed using *agrobacteria* containing the plasmid A.t.-OK1-pBinB33-Hyg using the method described in Rocha-Sosa et al. (EMBO J. 8, (1989), 23-29) and plants regenerated. The plants obtained from this transformation event were designated 385JH.

d) Analysis of the Transgenic Potato Plants and the Starch Synthesised by These

Plants which exhibited an elevated activity of the heterologously expressed A.t.-OK1 protein and also plants in which the activity of the endogenous OK1 protein was reduced by a co-suppression effect were identified by means of a Western Blot analysis. The Western Blot analysis was carried out using the antibody described under Example 11

Figure 7:
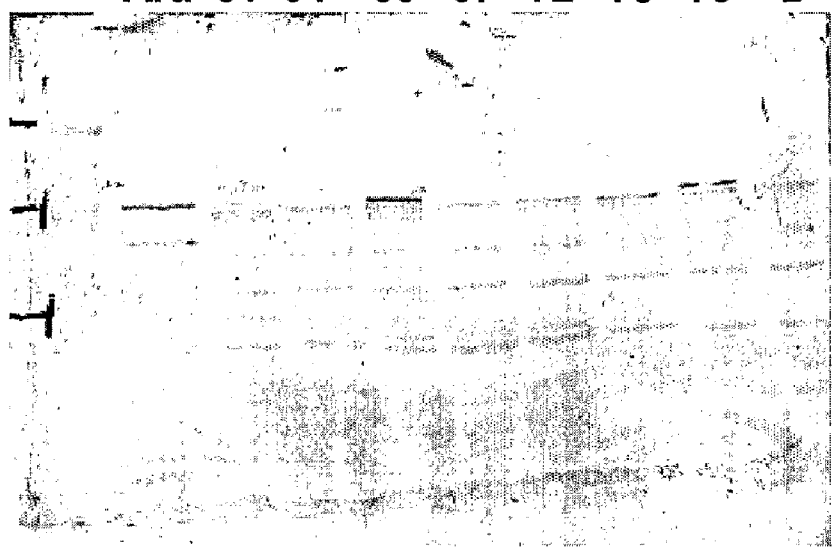
FIG. 7 Western Blot analysis of protein extracts from plants using an antibody against the OK1 protein from *Arabidopsis thaliana*. Protein extracts from leaves of the following plants are shown: Ara, *Arabidosis thaliana*; 51, 54, 55, 67, 72, 73, 79, 62, 63, 64, 65, 69, 66, 68 are independent lines of the transformation 385JH; D wildtype *Solanum tuberosum* cv Désirée.
Figure 7:
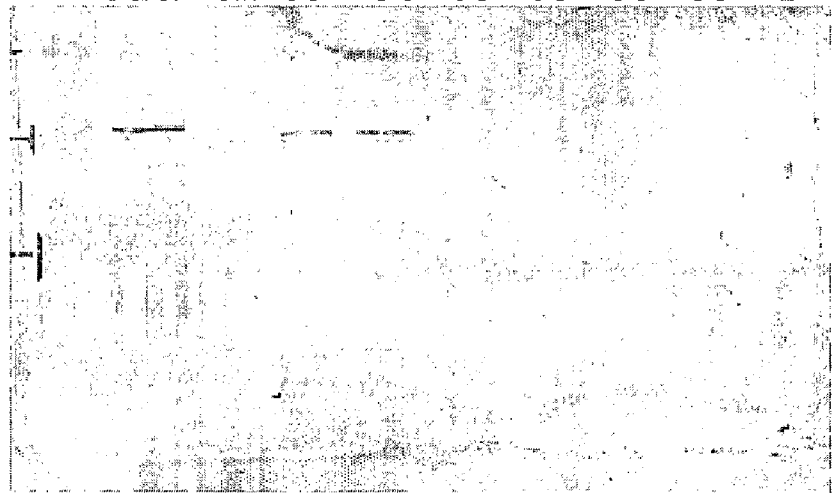

FIG. 7 exemplary shows the detection of the A.t.-OK1 Protein in single plants from the transformation event 385JH by means of Western Blot analysis. For induction of the B33 Promotor in leaf tissue single lines of the transformation event 385JH were cultivated on solidified Musharige Skoog medium containing 100 mM sucrose in tissue culture for two days. After harvest protein extracts were produced from leaf tissue of these plants according to the method described under General Methods, Item 1a). After separation of the proteins by means of denaturing polyacrylamide gel electrophoreses 40 μg protein extract of each line was analysed by means of Western Blot analysis using the antibody described under Examples, Item 10. As control samples, protein extracts from *Arabidopsis* plants and from potato wildtype plants (cv Désirée) were also analysed.

Plants which exhibited an elevated quantity of A.t.-OK1 protein compared to the corresponding wild type plants were cultivated in the greenhouse. Starch which was isolated from tubers of these plants showed an elevated content of phosphate covalently bound to the starch compared to the starch isolated from non-transformed wild type plants.

A. 14. Analysis of *Arabidopsis thalliana* plants which exhibit a reduced activity of a protein according to the invention T-DNA insertion mutants of *Arabidopsis thaliana* (available from the Salk Institute Genomic Analysis Laboratory, 10010 N. Torrey Pines Road, La Jolla, CA 92037, signal-.salk.edu/under ACC. No.: Salk_110814, Alias N610814), which were homozygotic with respect to insertion in the OK1 gene, were grown under the following conditions:

Light phase: 16 hours, 20° C.
Dark phase: 8 hours, 16° C.
Shortly before the flowers developed, the plants were cultivated in a light phase of 12 hours at 20° C. and a dark phase of 12 hours at 17° C.

Plants of the mutant line obtained (Salk_110814) were cultivated from 3 different seeds of the original seed material (Salk_110814-1, Salk_110814-2, Salk_110814-3) for analysis.

At the end of the dark phase, 10 leaves were removed in each case from 6 wild type plants (Ökotyp Columbia) and decolourised in 70% ethanol at 50° C. Furthermore, 6 leaves were removed in each case from respectively 4 different plants of the mutant lines Salk_110814-1, Salk_110814-2 or Salk_110814-3 which were in each case homozygotic with respect to T-DNA insertion in an OK1 gene, and these were decolourised in 70% ethanol at 50° C. The leaves were then incubated for 10 minutes in Lugol's solution before excess Lugol's solution was rinsed off the leaves with tap water. All leaves from wild type plants showed no staining with Lugol's solution. On the other hand, all leaves of the mutant lines Salk_110814-1, Salk_110814-2 or Salk_110814-3 showed a dark brown or black colouration (see FIG. 7). The mutant lines therefore showed a starch excess phenotype compared to the wild type plants. During cultivation no differences relating to the growth could be established between the mutant lines and the wild type plants.

Genetically modified *Arabidopsis thaliana* plants which were transformed with an RNAi construct containing "inverted repeats" of the coding region of an OK1 gene under control of the 35S promoter, were analysed with the aid of Western blot analysis using the antibody described in Example 10. Several independent lines which exhibited a reduced quantity of OK1 protein compared to wild type plants were identified. These lines were cultivated under the culture conditions specified above. In each case, 5 leaves of the individual lines were removed at the end of the dark phase (12 hours at 17° C.), decolourised in ethanol and stained with Lugol's solution. All the plants showed a starch excess phenotype compared to corresponding wild type plants. During cultivation no differences relating to growth could be established between the genetically modified plants and the wild type plants. The plants genetically modified by means of RNAi technology thus showed the same properties as the mutant lines Salk_110814-1, Salk_110814-2 or Salk_110814-3.

In each case four *Arabidopsis thaliana* plants of the lines A.t.-alpha-OK1-1, A.t.-alpha-OK1-2, A.t.-alpha-OK1-3, A.t.-alpha-OK1-4, A.t.-alpha-OK1-5, resulting from independent transformation events, in which the quantity of OK1 protein is reduced by means of RNAi technology, were investigated for their starch content at different times. The reduction in the quantity of OK1 protein in the respective lines was demonstrated by means of Western blot analysis (see FIG. 8). The leaf starch content of the individual lines was determined using the starch kits from Boehringer Mannheim (Product No.: 0207748). For this purpose, in each case all the leaves of four plants of the individual lines were harvested and the leaves were homogenised using mortars. 40 mg to 60 mg of the homogenised leaf material was washed twice with 80% ethanol in each case and the supernatant was discarded. The remaining material, which is not soluble in ethanol, was freeze-dried after being washed once in 1 ml of water, then dissolved in 0.5 ml of 0.2M KOH at 95° C. for 1 h and the solution obtained was adjusted to pH 7 using 88 μL of 1 M acetic acid. 25 μl of the respective solution obtained was mixed with 50 μl of amyloglucosidase solution (Starch-Kit from Boehringer Mannheim, Product No.: 0207748), to which 1 unit of alpha-amylase (from *Bacillus amyloliquefaciens*, Boehringer, Prod-No. 161764) had been added and was incubated for 1 h at 55° C. 20 μl of the solution treated with amyloglucosidase and alpha-amylase was then used to determine the glucose using an enzymatic coupled photometric test (see product information sheet for the determination of native starch from Boehringer Inmgelheim, Product No.: 0207748) At the same time as the transgenic lines, the starch content was also determined in leaves of *Arabidopsis thaliana* wild type plants (Ecotype Columbia). The wild type plants and the transgenic plants were cultivated under the same conditions: 12 hours light phase followed by 12 hours dark phase.

Leaves of the respective transgenic plant lines and wild type plants were harvested in each case ca. 4.5 weeks after seed germination after the end of the dark phase, after the end of a light phase and after the end of a second dark phase which directly followed the light phase. For each transgenic plant line, two independent extracts were produced in each case, from which two measurements of the starch content were made in each case. For wild type plants four extracts were produced in each case from which two measurements of the starch content were made in each case. The determination of the leaf starch contents yielded the following results:

TABLE 4

Quantity of leaf starch in *Arabidopsis thaliana* plants in which the quantity of OK1 protein is reduced using RNAi technology.

| | Line | Starch content (mg/g FW) | Standard deviation* |
|---|---|---|---|
| End dark phase 1 | A.t.-alpha-OK1-1 | 4.09 | 0.55 |
| | A.t.-alpha-OK1-2 | 4.93 | 0.94 |
| | A.t.-alpha-OK1-3 | 5.59 | 0.52 |
| | A.t.-alpha-OK1-4 | 6.36 | 0.87 |
| | A.t.-alpha-OK1-5 | 1.49 | 0.99 |
| | Wild type | 0.78 | 0.14 |
| End light phase | A.t.-alpha-OK1-1 | 9.30 | 0.96 |
| | A.t.-alpha-OK1-2 | 9.86 | 1.45 |
| | A.t.-alpha-OK1-3 | 11.68 | 1.60 |
| | A.t.-alpha-OK1-4 | 9.53 | 1.25 |
| | A.t.-alpha-OK1-5 | 6.61 | 0.71 |
| | Wild type | 5.61 | 0.72 |
| End dark phase 2 | A.t.-alpha-OK1-1 | 3.92 | 0.83 |
| | A.t.-alpha-OK1-2 | 4.35 | 1.07 |
| | A.t.-alpha-OK1-3 | 6.00 | 0.63 |
| | A.t.-alpha-OK1-4 | 5.34 | 1.35 |
| | A.t.-alpha-OK1-5 | 1.46 | 0.56 |
| | Wild type | 0.62 | 0.18 |

*Standard deviation using the general formula: root $[(n\Sigma x^2 - (\Sigma x)^2)/n(n-1)]$ 15. Analysis of Starch Isolated from Plants Which Exhibit a Reduced Activity of an OK1 Protein Starch was isolated from leaves of the plants described in Example 14 and hydrolysed using the method described under General Methods, Item 13 and then separated by means of HPAE analysis. The areas of the separated signals obtained by means of HPAE analysis for C-3 phosphate and C-6 phosphate were calculated (Software: Chromelion 6.20 from Dionex, USA) and the values obtained were given as the ratio to one another. The ratio of C-6 phosphate to C-3 phosphate in wild type plants was 2.1. In the plants described in Example 14 in which the activity of the OK1 protein was reduced by means of RNAi technology, on the other hand, the average ratio of C-6 phosphate to C-3 phosphate determined by analysing the starch isolated from the lines A.t.-alpha-OK1-1, A.t.-alpha-OK1-2, A.t.-alpha-OK1-3, A.t.-alpha-OK1-4 und A.t.-alpha-OK1-5 was 2.5. The analysis of starch from the line A.t.-alpha-OK1-5 yielded the lowest ratio of C-6 phosphate to C-3 phosphate (ratio of 2.2), starch from the line A.t.-alpha-OK1-1 yielded the highest ratio (ratio of 2.7).

Starch isolated from leaves of the mutants described in Example 13 which exhibit a reduced activity of an OK1 protein showed an increase in the ratio of C-6 phosphate to C-3 phosphate in the starch concerned.

The invention claimed is:

1. A method for identifying a protein which has an elevated binding activity towards phosphorylated alpha-1,4-glucans, compared to non-phosphorylated alpha-1,4 glucans, comprising
   a) incubating protein extracts in preparations separate from one another with
      i. phosphorylated alpha-1,4-glucans and
      ii. non-phosphorylated alpha-1,4-glucans,
   b) dissolving proteins specifically bound to the
      i. phosphorylated alpha-1,4-glucans from step a) i and
      ii. proteins specifically bound to the non-phosphorylated alpha-1,4-glucans from step a) ii
      in preparations separate from one another and
   c) identifying proteins which exhibit an elevated binding activity towards phosphorylated alpha-1,4-glucans used in step b) i, compared to non-phosphorylated alpha-1,4-glucans used in step b) ii.

2. An isolated protein obtained by the method of claim 1, wherein the isolated protein is an OK1 protein and wherein said OK1 protein comprises SEQ ID No.: 5.

3. A method for identifying a nucleic acid molecule coding for a protein which exhibits alpha-1,4-glucan phosphorylating enzymatic activity,
   a) identifying a protein by a method according to claim 1,
   b) determining amino acid sequences coding for the protein identified according to step a) and
   c) identifying nucleic acid molecules using the amino acids determined according to step b).

4. The method according to claim 3, wherein nucleic acid oligonucleotides based on the amino acid sequence determined according to step b) are manufactured to identify said nucleic acid molecule according to step c).

5. The method for identifying a nucleic acid molecule coding for a protein which exhibits alpha-1,4-glucan phosphorylating enzymatic activity, comprising
   a) identifying a protein by a method according to claim 1,
   b) producing antibodies which react specifically with the protein identified according to step a) and
   c) identifying nucleic acid molecules using the antibodies produced according to step b).

6. A method for identifying a protein which exhibits alpha-1,4-glucan phosphorylating enzymatic activity and requires phosphorylated alpha-1,4-glucans as substrate, comprising
   a) incubating protein extracts with phosphorylated alpha-1,4-glucans,
   b) dissolving proteins specifically bound to the phosphorylated alpha-1,4-glucans from step a), c) incubating proteins obtained according to step b) respectively with
  i. ATP and phosphorylated alpha-1,4-glucans and
  ii. ATP and non-phosphorylated alpha-1,4-glucans in preparations separated from one another,
d) examining the respective alpha-1,4-glucan obtained after incubation in step c) i or step c) ii for introduction of further phosphate groups and
e) identifying proteins which in the incubation preparation according to c) i have introduced significant quantities of phosphate groups into alpha-1,4-glucans and in the incubation preparation according to c) ii have introduced no significant quantities of phosphate groups into alpha-1,4-glucans.

7. The method according to claim 6, wherein the protein with alpha-1,4-glucan phosphorylating enzymatic activity uses phosphorylated starch as substrate.

8. The method according to claim 7, wherein the protein with alpha-1,4-glucan phosphorylating enzymatic activity originates from a plant.

9. An isolated protein obtained by the method claim 6, wherein the isolated protein is an OK1 protein, and wherein said OK1 protein requires phosphorylated α-1,4 glucans as a substrate and comprises SEQ ID No.: 5.

10. A method for identifying a nucleic acid molecule coding for a protein which exhibits alpha-1,4-glucan phosphorylating enzymatic activity, comprising
  a) identifying a protein by a method according to claim 6,
  b) determining amino acid sequences coding for the protein identified according to step a) and
  c) identify nucleic acid molecules using the amino acids determined according to step b).

11. The method according to claim 10, wherein nucleic acid oligonucleotides based on the amino acid sequence determined according to step b) are manufactured to identify said nucleic acid molecule according to step c).

12. The method for identifying a nucleic acid molecule coding for a protein which exhibits alpha-1,4-glucan phosphorylating enzymatic activity, comprising
  a) identify a protein by a method according to claim 6,
  b) producing antibodies which react specifically with the protein identified according to step a) and
  c) identify nucleic acid molecules using the antibodies produced according to step b).

13. The isolated protein of claim 2, wherein the protein comprises SEQ ID No.: 4.

14. The isolated protein of claim 9, wherein the protein introduces phosphate monoester bonds into the C-3 position of a glucose molecule of a P-α-1,4 glucan.

* * * * *

SEQUENCE LISTING

```
<160> NUMBER OF SEQ ID NOS: 46

<210> SEQ ID NO 1
<211> LENGTH: 3591
<212> TYPE: DNA
<213> ORGANISM: Arabidopsis thaliana
<220> FEATURE:
<221> NAME/KEY: CDS
<222> LOCATION: (1)..(3591)
<223> OTHER INFORMATION:

<400> SEQUENCE: 1 atg gag agc att ggc agc cat tgt tgc agc tct cct ttc acc ttc atc      48
Met Glu Ser Ile Gly Ser His Cys Cys Ser Ser Pro Phe Thr Phe Ile
1               5                   10                  15 act aga aac tca tca tca tca ctt cct aga ctc gtt aac atc act cac      96
Thr Arg Asn Ser Ser Ser Ser Leu Pro Arg Leu Val Asn Ile Thr His
            20                  25                  30 aga gtt aat ctc agc cac caa tct cac cga ctc aga aac tcc aat tct     144
Arg Val Asn Leu Ser His Gln Ser His Arg Leu Arg Asn Ser Asn Ser
        35                  40                  45 cgt ctc act tgc act gct act tct tct tcc acc att gag gaa caa cgg     192
Arg Leu Thr Cys Thr Ala Thr Ser Ser Ser Thr Ile Glu Glu Gln Arg
    50                  55                  60 aag aag aaa gat gga tca gga acg aaa gtg agg ttg aat gtg agg tta     240
Lys Lys Lys Asp Gly Ser Gly Thr Lys Val Arg Leu Asn Val Arg Leu
65                  70                  75                  80 gat cat caa gtt aat ttt ggt gac cat gtg gct atg ttt gga tca gct     288
Asp His Gln Val Asn Phe Gly Asp His Val Ala Met Phe Gly Ser Ala
                85                  90                  95 aaa gag att ggt tca tgg aaa aag aaa tcg cct ttg aat tgg agt gag     336
Lys Glu Ile Gly Ser Trp Lys Lys Lys Ser Pro Leu Asn Trp Ser Glu
            100                 105                 110 aat gga tgg gtt tgt gag ttg gaa ctt gac ggt ggt cag gtt ttg gag     384
Asn Gly Trp Val Cys Glu Leu Glu Leu Asp Gly Gly Gln Val Leu Glu
```

-continued

```
                115                 120                 125
tat aag ttt gtc att gtt aag aat gat ggt tca ctt tca tgg gaa tct      432
Tyr Lys Phe Val Ile Val Lys Asn Asp Gly Ser Leu Ser Trp Glu Ser
    130                 135                 140 ggt gat aat cgt gtc ctt aag gtt cca aat tct ggg aat ttt tct gtt      480
Gly Asp Asn Arg Val Leu Lys Val Pro Asn Ser Gly Asn Phe Ser Val
145                 150                 155                 160 gtt tgt cat tgg gat gct act aga gaa acc ctt gat ttg cct cag gag      528
Val Cys His Trp Asp Ala Thr Arg Glu Thr Leu Asp Leu Pro Gln Glu
                165                 170                 175 gtt ggt aat gat gat gat gtt ggt gat ggt ggg cat gag agg gat aat      576
Val Gly Asn Asp Asp Asp Val Gly Asp Gly Gly His Glu Arg Asp Asn
            180                 185                 190 cat gat gtt ggt gat gat aga gta gtg gga agt gaa aat ggt gcg cag      624
His Asp Val Gly Asp Asp Arg Val Val Gly Ser Glu Asn Gly Ala Gln
        195                 200                 205 ctt cag aag agt aca ttg ggt ggg caa tgg caa ggt aaa gat gcg tcc      672
Leu Gln Lys Ser Thr Leu Gly Gly Gln Trp Gln Gly Lys Asp Ala Ser
    210                 215                 220 ttt atg cgt tct aat gat cat ggt aac aga gaa gtt ggt aga aat tgg      720
Phe Met Arg Ser Asn Asp His Gly Asn Arg Glu Val Gly Arg Asn Trp
225                 230                 235                 240 gat act agt ggt ctt gaa ggc aca gct ctt aag atg gtt gag ggt gat      768
Asp Thr Ser Gly Leu Glu Gly Thr Ala Leu Lys Met Val Glu Gly Asp
                245                 250                 255 cgc aac tct aag aac tgg tgg aga aag ctt gaa atg gta cgc gag gtt      816
Arg Asn Ser Lys Asn Trp Trp Arg Lys Leu Glu Met Val Arg Glu Val
            260                 265                 270 ata gtt ggg agt gtt gag agg gag gaa cga ttg aag gcg ctc ata tac      864
Ile Val Gly Ser Val Glu Arg Glu Glu Arg Leu Lys Ala Leu Ile Tyr
        275                 280                 285 tct gca att tat ttg aag tgg ata aac aca ggt cag att cct tgt ttt      912
Ser Ala Ile Tyr Leu Lys Trp Ile Asn Thr Gly Gln Ile Pro Cys Phe
    290                 295                 300 gaa gat gga ggg cat cac cgt cca aac agg cat gcc gag att tcc aga      960
Glu Asp Gly Gly His His Arg Pro Asn Arg His Ala Glu Ile Ser Arg
305                 310                 315                 320 ctt ata ttc cgt gag ttg gag cac att tgc agt aag aaa gat gct act     1008
Leu Ile Phe Arg Glu Leu Glu His Ile Cys Ser Lys Lys Asp Ala Thr
                325                 330                 335 cca gag gaa gtg ctt gtt gct cgg aaa atc cat ccg tgt tta cct tct     1056
Pro Glu Glu Val Leu Val Ala Arg Lys Ile His Pro Cys Leu Pro Ser
            340                 345                 350 ttc aaa gca gag ttt act gca gct gtc cct cta act cgg att agg gac     1104
Phe Lys Ala Glu Phe Thr Ala Ala Val Pro Leu Thr Arg Ile Arg Asp
        355                 360                 365 ata gcc cat cgg aat gat att cct cat gat ctc aag caa gaa atc aag     1152
Ile Ala His Arg Asn Asp Ile Pro His Asp Leu Lys Gln Glu Ile Lys
    370                 375                 380 cat acg ata caa aat aag ctt cac cgg aat gct ggt cca gaa gat cta     1200
His Thr Ile Gln Asn Lys Leu His Arg Asn Ala Gly Pro Glu Asp Leu
385                 390                 395                 400 att gca aca gaa gca atg ctt caa cga att acc gag acc cca gga aaa     1248
Ile Ala Thr Glu Ala Met Leu Gln Arg Ile Thr Glu Thr Pro Gly Lys
                405                 410                 415 tat agt gga gac ttt gtg gag cag ttt aaa ata ttc cat aat gag ctt     1296
Tyr Ser Gly Asp Phe Val Glu Gln Phe Lys Ile Phe His Asn Glu Leu
            420                 425                 430 aaa gat ttc ttt aat gct gga agt ctc act gaa cag ctt gat tct atg     1344
Lys Asp Phe Phe Asn Ala Gly Ser Leu Thr Glu Gln Leu Asp Ser Met
```

```
                435                 440                 445
aaa att tct atg gat gat aga ggt ctt tct gcg ctc aat ttg ttt ttt         1392
Lys Ile Ser Met Asp Asp Arg Gly Leu Ser Ala Leu Asn Leu Phe Phe
            450                 455                 460 gaa tgt aaa aag cgc ctt gac aca tca gga gaa tca agc aat gtt ttg         1440
Glu Cys Lys Lys Arg Leu Asp Thr Ser Gly Glu Ser Ser Asn Val Leu
465                 470                 475                 480 gag ttg att aaa acc atg cat tct cta gct tct tta aga gaa aca att         1488
Glu Leu Ile Lys Thr Met His Ser Leu Ala Ser Leu Arg Glu Thr Ile
                485                 490                 495 ata aag gaa ctt aat agc ggc ttg cga aat gat gct cct gat act gcc         1536
Ile Lys Glu Leu Asn Ser Gly Leu Arg Asn Asp Ala Pro Asp Thr Ala
            500                 505                 510 att gca atg cgc cag aag tgg cgc ctt tgt gag atc ggc ctc gag gac         1584
Ile Ala Met Arg Gln Lys Trp Arg Leu Cys Glu Ile Gly Leu Glu Asp
            515                 520                 525 tac ttt ttt gtt cta cta agc aga ttc ctc aat gct ctt gaa act atg         1632
Tyr Phe Phe Val Leu Leu Ser Arg Phe Leu Asn Ala Leu Glu Thr Met
            530                 535                 540 gga gga gct gat caa ctg gca aaa gat gtg gga tca aga aac gtt gcc         1680
Gly Gly Ala Asp Gln Leu Ala Lys Asp Val Gly Ser Arg Asn Val Ala
545                 550                 555                 560 tca tgg aat gat cca cta gat gct ttg gtg ttg ggt gtt cac caa gta         1728
Ser Trp Asn Asp Pro Leu Asp Ala Leu Val Leu Gly Val His Gln Val
                565                 570                 575 ggt cta tct ggt tgg aag caa gaa gaa tgt tta gcc att gga aat gaa         1776
Gly Leu Ser Gly Trp Lys Gln Glu Glu Cys Leu Ala Ile Gly Asn Glu
            580                 585                 590 ctc ctt gct tgg cga gaa agg gac cta ctt gaa aaa gaa ggg gaa gag         1824
Leu Leu Ala Trp Arg Glu Arg Asp Leu Leu Glu Lys Glu Gly Glu Glu
            595                 600                 605 gat gga aaa aca att tgg gcc atg agg ctg aaa gca act ctt gat cga         1872
Asp Gly Lys Thr Ile Trp Ala Met Arg Leu Lys Ala Thr Leu Asp Arg
            610                 615                 620 gca cgc aga tta aca gca gaa tat tct gat ttg ctt ctt caa ata ttt         1920
Ala Arg Arg Leu Thr Ala Glu Tyr Ser Asp Leu Leu Leu Gln Ile Phe
625                 630                 635                 640 cct cct aat gtg gag att tta gga aaa gct cta gga att cca gag aat         1968
Pro Pro Asn Val Glu Ile Leu Gly Lys Ala Leu Gly Ile Pro Glu Asn
                645                 650                 655 agt gtc aag acc tat aca gaa gca gag att cgt gct gga att att ttc         2016
Ser Val Lys Thr Tyr Thr Glu Ala Glu Ile Arg Ala Gly Ile Ile Phe
            660                 665                 670 cag atc tca aag ctc tgc act gtt ctt cta aaa gct gta aga aat tca         2064
Gln Ile Ser Lys Leu Cys Thr Val Leu Leu Lys Ala Val Arg Asn Ser
            675                 680                 685 ctt ggt tct gag ggc tgg gat gtc gtt gta cct gga tcg acg tct ggg         2112
Leu Gly Ser Glu Gly Trp Asp Val Val Val Pro Gly Ser Thr Ser Gly
690                 695                 700 aca tta gtt cag gtt gag agc att gtt ccg gga tca ttg cca gca act         2160
Thr Leu Val Gln Val Glu Ser Ile Val Pro Gly Ser Leu Pro Ala Thr
705                 710                 715                 720 tct ggt ggt cct att att ctc ttg gtc aat aaa gct gat ggc gat gaa         2208
Ser Gly Gly Pro Ile Ile Leu Leu Val Asn Lys Ala Asp Gly Asp Glu
                725                 730                 735 gag gta agt gct gct aat ggg aac ata gct gga gtc atg ctt ctg cag         2256
Glu Val Ser Ala Ala Asn Gly Asn Ile Ala Gly Val Met Leu Leu Gln
            740                 745                 750 gag ctg cct cac ttg tct cac ctt ggc gtt aga gcg cgg cag gag aaa         2304
Glu Leu Pro His Leu Ser His Leu Gly Val Arg Ala Arg Gln Glu Lys
```

```
                    755                 760                 765
att gtc ttt gtg aca tgt gat gat gat gac aag gtt gct gat ata cga    2352
Ile Val Phe Val Thr Cys Asp Asp Asp Asp Lys Val Ala Asp Ile Arg
770                 775                 780 cga ctt gtg gga aaa ttt gtg agg ttg gaa gca tct cca agt cat gtg    2400
Arg Leu Val Gly Lys Phe Val Arg Leu Glu Ala Ser Pro Ser His Val
785                 790                 795                 800 aat ctg ata ctt tca act gag ggt agg agt cgc act tcc aaa tcc agt    2448
Asn Leu Ile Leu Ser Thr Glu Gly Arg Ser Arg Thr Ser Lys Ser Ser
            805                 810                 815 gcg acc aaa aaa acg gat aag aac agc tta tct aag aaa aaa aca gat    2496
Ala Thr Lys Lys Thr Asp Lys Asn Ser Leu Ser Lys Lys Lys Thr Asp
        820                 825                 830 aag aag agc tta tct atc gat gat gaa gaa tca aag cct ggt tcc tca    2544
Lys Lys Ser Leu Ser Ile Asp Asp Glu Glu Ser Lys Pro Gly Ser Ser
    835                 840                 845 tct tcc aat agc ctc ctt tac tct tcc aag gat atc cct agt gga gga    2592
Ser Ser Asn Ser Leu Leu Tyr Ser Ser Lys Asp Ile Pro Ser Gly Gly
850                 855                 860 atc ata gca ctt gct gat gca gat gta cca act tct ggt tca aaa tct    2640
Ile Ile Ala Leu Ala Asp Ala Asp Val Pro Thr Ser Gly Ser Lys Ser
865                 870                 875                 880 gct gca tgt ggt ctt ctt gca tct tta gca gaa gcc tct agt aaa gtg    2688
Ala Ala Cys Gly Leu Leu Ala Ser Leu Ala Glu Ala Ser Ser Lys Val
            885                 890                 895 cac agc gaa cac gga gtt ccg gca tca ttt aag gtt cca act gga gtt    2736
His Ser Glu His Gly Val Pro Ala Ser Phe Lys Val Pro Thr Gly Val
        900                 905                 910 gtc ata cct ttt gga tcg atg gaa tta gct tta aag caa aat aat tcg    2784
Val Ile Pro Phe Gly Ser Met Glu Leu Ala Leu Lys Gln Asn Asn Ser
    915                 920                 925 gaa gaa aag ttt gcg tct ttg cta gaa aaa cta gaa acc gcc aga cct    2832
Glu Glu Lys Phe Ala Ser Leu Leu Glu Lys Leu Glu Thr Ala Arg Pro
930                 935                 940 gag ggt ggt gag cta gac gac ata tgt gac cag atc cat gaa gtg atg    2880
Glu Gly Gly Glu Leu Asp Asp Ile Cys Asp Gln Ile His Glu Val Met
945                 950                 955                 960 aaa acg ttg caa gtg cct aaa gaa aca atc aac agc ata agc aaa gcg    2928
Lys Thr Leu Gln Val Pro Lys Glu Thr Ile Asn Ser Ile Ser Lys Ala
            965                 970                 975 ttt ctc aaa gat gct cgt ctc att gtt cgt tca agt gct aac gtc gag    2976
Phe Leu Lys Asp Ala Arg Leu Ile Val Arg Ser Ser Ala Asn Val Glu
        980                 985                 990 gac tta gcc gga atg tca gct gca gga ctc tat gaa tca atc cct aac    3024
Asp Leu Ala Gly Met Ser Ala Ala Gly Leu Tyr Glu Ser Ile Pro Asn
    995                 1000                1005 gtg agt ccc tcg gat cct ttg gtg ttt tca gat tcg gtt tgc caa        3069
Val Ser Pro Ser Asp Pro Leu Val Phe Ser Asp Ser Val Cys Gln
1010                1015                1020 gtt tgg gct tct ctc tac aca aga aga gct gtt cta agc cgt aga        3114
Val Trp Ala Ser Leu Tyr Thr Arg Arg Ala Val Leu Ser Arg Arg
    1025                1030                1035 gct gct ggt gtc tct caa aga gaa gct tca atg gct gtt ctc gtt        3159
Ala Ala Gly Val Ser Gln Arg Glu Ala Ser Met Ala Val Leu Val
        1040                1045                1050 caa gaa atg ctt tcg ccg gac tta tca ttc gtt ctg cac aca gtg        3204
Gln Glu Met Leu Ser Pro Asp Leu Ser Phe Val Leu His Thr Val
            1055                1060                1065 agt cca gct gat ccg gac agt aac ctt gtg gaa gcc gag atc gct        3249
Ser Pro Ala Asp Pro Asp Ser Asn Leu Val Glu Ala Glu Ile Ala
```

-continued

```
                   1070                1075                1080
cct ggt tta ggt gag act tta gct tca gga aca aga gga aca cca         3294
Pro Gly Leu Gly Glu Thr Leu Ala Ser Gly Thr Arg Gly Thr Pro
    1085                1090                1095 tgg aga ctc gct tcg ggt aag ctc gac ggg att gta caa acc tta         3339
Trp Arg Leu Ala Ser Gly Lys Leu Asp Gly Ile Val Gln Thr Leu
    1100                1105                1110 gct ttc gca aac ttc agc gaa gag ctt ctt gtg tca gga aca ggt         3384
Ala Phe Ala Asn Phe Ser Glu Glu Leu Leu Val Ser Gly Thr Gly
    1115                1120                1125 cct gct gat gga aaa tac gtt cgg ttg acc gtg gac tat agc aaa         3429
Pro Ala Asp Gly Lys Tyr Val Arg Leu Thr Val Asp Tyr Ser Lys
    1130                1135                1140 aaa cgt tta act gtt gac tcg gtg ttt aga cag cag ctc ggt cag         3474
Lys Arg Leu Thr Val Asp Ser Val Phe Arg Gln Gln Leu Gly Gln
    1145                1150                1155 aga ctc ggt tcg gtt ggt ttc ttc ttg gaa aga aac ttt ggc tgt         3519
Arg Leu Gly Ser Val Gly Phe Phe Leu Glu Arg Asn Phe Gly Cys
    1160                1165                1170 gct caa gac gtt gaa ggt tgt ttg gtt ggt gaa gat gtt tac att         3564
Ala Gln Asp Val Glu Gly Cys Leu Val Gly Glu Asp Val Tyr Ile
    1175                1180                1185 gtt cag tca agg cca caa cct ctg tag                                 3591
Val Gln Ser Arg Pro Gln Pro Leu
    1190                1195

<210> SEQ ID NO 2
<211> LENGTH: 1196
<212> TYPE: PRT
<213> ORGANISM: Arabidopsis thaliana

<400> SEQUENCE: 2

Met Glu Ser Ile Gly Ser His Cys Cys Ser Ser Pro Phe Thr Phe Ile
1               5                   10                  15

Thr Arg Asn Ser Ser Ser Leu Pro Arg Leu Val Asn Ile Thr His
            20                  25                  30

Arg Val Asn Leu Ser His Gln Ser His Arg Leu Arg Asn Ser Asn Ser
        35                  40                  45

Arg Leu Thr Cys Thr Ala Thr Ser Ser Ser Thr Ile Glu Glu Gln Arg
    50                  55                  60

Lys Lys Lys Asp Gly Ser Gly Thr Lys Val Arg Leu Asn Val Arg Leu
65                  70                  75                  80

Asp His Gln Val Asn Phe Gly Asp His Val Ala Met Phe Gly Ser Ala
                85                  90                  95

Lys Glu Ile Gly Ser Trp Lys Lys Lys Ser Pro Leu Asn Trp Ser Glu
            100                 105                 110

Asn Gly Trp Val Cys Glu Leu Glu Leu Asp Gly Gly Gln Val Leu Glu
        115                 120                 125

Tyr Lys Phe Val Ile Val Lys Asn Asp Gly Ser Leu Ser Trp Glu Ser
    130                 135                 140

Gly Asp Asn Arg Val Leu Lys Val Pro Asn Ser Gly Asn Phe Ser Val
145                 150                 155                 160

Val Cys His Trp Asp Ala Thr Arg Glu Thr Leu Asp Leu Pro Gln Glu
                165                 170                 175

Val Gly Asn Asp Asp Val Gly Asp Gly Gly His Glu Arg Asp Asn
            180                 185                 190

His Asp Val Gly Asp Asp Arg Val Val Gly Ser Glu Asn Gly Ala Gln
        195                 200                 205
```

```
Leu Gln Lys Ser Thr Leu Gly Gly Gln Trp Gln Gly Lys Asp Ala Ser
    210                 215                 220

Phe Met Arg Ser Asn Asp His Gly Asn Arg Glu Val Gly Arg Asn Trp
225                 230                 235                 240

Asp Thr Ser Gly Leu Glu Gly Thr Ala Leu Lys Met Val Glu Gly Asp
                245                 250                 255

Arg Asn Ser Lys Asn Trp Trp Arg Lys Leu Glu Met Val Arg Glu Val
            260                 265                 270

Ile Val Gly Ser Val Glu Arg Glu Arg Leu Lys Ala Leu Ile Tyr
        275                 280                 285

Ser Ala Ile Tyr Leu Lys Trp Ile Asn Thr Gly Gln Ile Pro Cys Phe
    290                 295                 300

Glu Asp Gly Gly His His Arg Pro Asn Arg His Ala Glu Ile Ser Arg
305                 310                 315                 320

Leu Ile Phe Arg Glu Leu Glu His Ile Cys Ser Lys Lys Asp Ala Thr
                325                 330                 335

Pro Glu Glu Val Leu Val Ala Arg Lys Ile His Pro Cys Leu Pro Ser
            340                 345                 350

Phe Lys Ala Glu Phe Thr Ala Ala Val Pro Leu Thr Arg Ile Arg Asp
        355                 360                 365

Ile Ala His Arg Asn Asp Ile Pro His Asp Leu Lys Gln Glu Ile Lys
    370                 375                 380

His Thr Ile Gln Asn Lys Leu His Arg Asn Ala Gly Pro Glu Asp Leu
385                 390                 395                 400

Ile Ala Thr Glu Ala Met Leu Gln Arg Ile Thr Glu Thr Pro Gly Lys
                405                 410                 415

Tyr Ser Gly Asp Phe Val Glu Gln Phe Lys Ile Phe His Asn Glu Leu
            420                 425                 430

Lys Asp Phe Phe Asn Ala Gly Ser Leu Thr Glu Gln Leu Asp Ser Met
        435                 440                 445

Lys Ile Ser Met Asp Asp Arg Gly Leu Ser Ala Leu Asn Leu Phe Phe
    450                 455                 460

Glu Cys Lys Lys Arg Leu Asp Thr Ser Gly Glu Ser Ser Asn Val Leu
465                 470                 475                 480

Glu Leu Ile Lys Thr Met His Ser Leu Ala Ser Leu Arg Glu Thr Ile
                485                 490                 495

Ile Lys Glu Leu Asn Ser Gly Leu Arg Asn Asp Ala Pro Asp Thr Ala
            500                 505                 510

Ile Ala Met Arg Gln Lys Trp Arg Leu Cys Glu Ile Gly Leu Glu Asp
        515                 520                 525

Tyr Phe Phe Val Leu Leu Ser Arg Phe Leu Asn Ala Leu Glu Thr Met
    530                 535                 540

Gly Gly Ala Asp Gln Leu Ala Lys Asp Val Gly Ser Arg Asn Val Ala
545                 550                 555                 560

Ser Trp Asn Asp Pro Leu Asp Ala Leu Val Leu Gly Val His Gln Val
                565                 570                 575

Gly Leu Ser Gly Trp Lys Gln Glu Glu Cys Leu Ala Ile Gly Asn Glu
            580                 585                 590

Leu Leu Ala Trp Arg Glu Arg Asp Leu Leu Glu Lys Glu Gly Glu Glu
        595                 600                 605

Asp Gly Lys Thr Ile Trp Ala Met Arg Leu Lys Ala Thr Leu Asp Arg
    610                 615                 620

Ala Arg Arg Leu Thr Ala Glu Tyr Ser Asp Leu Leu Leu Gln Ile Phe
```

-continued

```
            625                 630                 635                 640
        Pro Pro Asn Val Glu Ile Leu Gly Lys Ala Leu Gly Ile Pro Glu Asn
                            645                 650                 655
        Ser Val Lys Thr Tyr Thr Glu Ala Glu Ile Arg Ala Gly Ile Ile Phe
                            660                 665                 670
        Gln Ile Ser Lys Leu Cys Thr Val Leu Leu Lys Ala Val Arg Asn Ser
                            675                 680                 685
        Leu Gly Ser Glu Gly Trp Asp Val Val Pro Gly Ser Thr Ser Gly
                            690                 695                 700
        Thr Leu Val Gln Val Glu Ser Ile Val Pro Gly Ser Leu Pro Ala Thr
        705                 710                 715                 720
        Ser Gly Gly Pro Ile Ile Leu Val Asn Lys Ala Asp Gly Asp Glu
                            725                 730                 735
        Glu Val Ser Ala Ala Asn Gly Asn Ile Ala Gly Val Met Leu Leu Gln
                            740                 745                 750
        Glu Leu Pro His Leu Ser His Leu Gly Val Arg Ala Arg Gln Glu Lys
                            755                 760                 765
        Ile Val Phe Val Thr Cys Asp Asp Asp Lys Val Ala Asp Ile Arg
                            770                 775                 780
        Arg Leu Val Gly Lys Phe Val Arg Leu Glu Ala Ser Pro Ser His Val
        785                 790                 795                 800
        Asn Leu Ile Leu Ser Thr Glu Gly Arg Ser Arg Thr Ser Lys Ser Ser
                            805                 810                 815
        Ala Thr Lys Lys Thr Asp Lys Asn Ser Leu Ser Lys Lys Thr Asp
                            820                 825                 830
        Lys Lys Ser Leu Ser Ile Asp Asp Glu Glu Ser Lys Pro Gly Ser Ser
                            835                 840                 845
        Ser Ser Asn Ser Leu Leu Tyr Ser Ser Lys Asp Ile Pro Ser Gly Gly
                            850                 855                 860
        Ile Ile Ala Leu Ala Asp Ala Asp Val Pro Thr Ser Gly Ser Lys Ser
        865                 870                 875                 880
        Ala Ala Cys Gly Leu Leu Ala Ser Leu Ala Glu Ala Ser Ser Lys Val
                            885                 890                 895
        His Ser Glu His Gly Val Pro Ala Ser Phe Lys Val Pro Thr Gly Val
                            900                 905                 910
        Val Ile Pro Phe Gly Ser Met Glu Leu Ala Leu Lys Gln Asn Asn Ser
                            915                 920                 925
        Glu Glu Lys Phe Ala Ser Leu Leu Glu Lys Leu Glu Thr Ala Arg Pro
                            930                 935                 940
        Glu Gly Gly Glu Leu Asp Asp Ile Cys Asp Gln Ile His Glu Val Met
        945                 950                 955                 960
        Lys Thr Leu Gln Val Pro Lys Glu Thr Ile Asn Ser Ile Ser Lys Ala
                            965                 970                 975
        Phe Leu Lys Asp Ala Arg Leu Ile Val Arg Ser Ala Asn Val Glu
                            980                 985                 990
        Asp Leu Ala Gly Met Ser Ala Ala  Gly Leu Tyr Glu Ser  Ile Pro Asn
                            995                 1000                1005
        Val Ser  Pro Ser Asp Pro Leu  Val Phe Ser Asp Ser  Val Cys Gln
                           1010                 1015                1020
        Val Trp  Ala Ser Leu Tyr Thr  Arg Arg Ala Val Leu  Ser Arg Arg
                           1025                 1030                1035
        Ala Ala  Gly Val Ser Gln Arg  Glu Ala Ser Met Ala  Val Leu Val
                           1040                 1045                1050
```

```
Gln Glu Met Leu Ser Pro Asp Leu Ser Phe Val Leu His Thr Val
        1055                1060                1065

Ser Pro Ala Asp Pro Asp Ser Asn Leu Val Glu Ala Glu Ile Ala
    1070                1075                1080

Pro Gly Leu Gly Glu Thr Leu Ala Ser Gly Thr Arg Gly Thr Pro
        1085                1090                1095

Trp Arg Leu Ala Ser Gly Lys Leu Asp Gly Ile Val Gln Thr Leu
    1100                1105                1110

Ala Phe Ala Asn Phe Ser Glu Glu Leu Leu Val Ser Gly Thr Gly
        1115                1120                1125

Pro Ala Asp Gly Lys Tyr Val Arg Leu Thr Val Asp Tyr Ser Lys
    1130                1135                1140

Lys Arg Leu Thr Val Asp Ser Val Phe Arg Gln Gln Leu Gly Gln
        1145                1150                1155

Arg Leu Gly Ser Val Gly Phe Phe Leu Glu Arg Asn Phe Gly Cys
    1160                1165                1170

Ala Gln Asp Val Glu Gly Cys Leu Val Gly Glu Asp Val Tyr Ile
        1175                1180                1185

Val Gln Ser Arg Pro Gln Pro Leu
    1190                1195

<210> SEQ ID NO 3
<211> LENGTH: 3644
<212> TYPE: DNA
<213> ORGANISM: Oryza sativa
<220> FEATURE:
<221> NAME/KEY: CDS
<222> LOCATION: (13)..(3633)
<223> OTHER INFORMATION:

<400> SEQUENCE: 3
cgaggaggat ca atg acg tcg ctg cgg ccc ctc gaa acc tcg ctc tcc ata      51
              Met Thr Ser Leu Arg Pro Leu Glu Thr Ser Leu Ser Ile
                1               5                  10 ggc ggc agg ccg cgc cgt ggt ctc gtc ctc ccg ccg ccc gga gtc ggt        99
Gly Gly Arg Pro Arg Arg Gly Leu Val Leu Pro Pro Pro Gly Val Gly
 15                  20                  25 gcg ggt gtg ctg ctc cgc cgg gga gcg atg gcg ctc cct ggg cgg cgc       147
Ala Gly Val Leu Leu Arg Arg Gly Ala Met Ala Leu Pro Gly Arg Arg
 30                  35                  40                  45 ggc ttc gcg tgc cgc ggg aga tcc gcg gcc tcg gcg gca gag aga aca       195
Gly Phe Ala Cys Arg Gly Arg Ser Ala Ala Ser Ala Ala Glu Arg Thr
                 50                  55                  60 aag gag aaa aag aga aga gat tct tca aag cag cca ttg gtg cat ctc       243
Lys Glu Lys Lys Arg Arg Asp Ser Ser Lys Gln Pro Leu Val His Leu
             65                  70                  75 cag gtt tgt cta gag cac cag gtt aag ttt ggt gag cat gta ggc att       291
Gln Val Cys Leu Glu His Gln Val Lys Phe Gly Glu His Val Gly Ile
         80                  85                  90 atc ggt tcc aca aag gag ctt ggt tca tgg gag gag cag gtt gaa ctg       339
Ile Gly Ser Thr Lys Glu Leu Gly Ser Trp Glu Glu Gln Val Glu Leu
     95                 100                 105 gaa tgg act aca aat ggt tgg gtc tgc cag ctt aag ctc cct gga gaa       387
Glu Trp Thr Thr Asn Gly Trp Val Cys Gln Leu Lys Leu Pro Gly Glu
110                 115                 120                 125 aca ctt gtg gag ttt aaa ttt gtt ata ttt ttg gtg gga gga aaa gat       435
Thr Leu Val Glu Phe Lys Phe Val Ile Phe Leu Val Gly Gly Lys Asp
                130                 135                 140 aaa ata tgg gaa gat ggt aat aac cgt gtt gtt gag ctg ccg aag gat       483
Lys Ile Trp Glu Asp Gly Asn Asn Arg Val Val Glu Leu Pro Lys Asp
```

-continued

```
                145                 150                 155
ggt aag ttt gat ata gta tgc cac tgg aat aga aca gaa gag cca tta      531
Gly Lys Phe Asp Ile Val Cys His Trp Asn Arg Thr Glu Glu Pro Leu
            160                 165                 170 gaa ctt tta gga aca cca aag ttt gag ttg gtc gga gaa gct gaa aag      579
Glu Leu Leu Gly Thr Pro Lys Phe Glu Leu Val Gly Glu Ala Glu Lys
175                 180                 185 aat act ggc gag gat gct tca gca tct gta act ttt gca cct gaa aaa      627
Asn Thr Gly Glu Asp Ala Ser Ala Ser Val Thr Phe Ala Pro Glu Lys
190                 195                 200                 205 gtt caa gat att tca gtt gtt gag aat ggt gat cca gca cca gag gcc      675
Val Gln Asp Ile Ser Val Val Glu Asn Gly Asp Pro Ala Pro Glu Ala
                210                 215                 220 gag tca agc aaa ttt ggt ggg caa tgg caa gga agt aaa act gtt ttc      723
Glu Ser Ser Lys Phe Gly Gly Gln Trp Gln Gly Ser Lys Thr Val Phe
            225                 230                 235 atg aga tca aat gag cat ctg aat aag gag gct gat agg atg tgg gat      771
Met Arg Ser Asn Glu His Leu Asn Lys Glu Ala Asp Arg Met Trp Asp
        240                 245                 250 aca act ggg ctt gat gga ata gca ctg aaa ctg gtg gag ggc gat aaa      819
Thr Thr Gly Leu Asp Gly Ile Ala Leu Lys Leu Val Glu Gly Asp Lys
    255                 260                 265 gca tcc agg aac tgg tgg cgg aag tta gag gtt gtt cgc ggg ata ttg      867
Ala Ser Arg Asn Trp Trp Arg Lys Leu Glu Val Val Arg Gly Ile Leu
270                 275                 280                 285 tca gaa tct ttt gat gac cag agt cgt ctg ggg gcc ctt gta tac tca      915
Ser Glu Ser Phe Asp Asp Gln Ser Arg Leu Gly Ala Leu Val Tyr Ser
                290                 295                 300 gct att tat ctg aag tgg att tat aca ggt cag ata tcg tgc ttt gaa      963
Ala Ile Tyr Leu Lys Trp Ile Tyr Thr Gly Gln Ile Ser Cys Phe Glu
            305                 310                 315 gat ggt ggc cac cat cgg cct aac aaa cat gct gag ata tcg agg caa     1011
Asp Gly Gly His His Arg Pro Asn Lys His Ala Glu Ile Ser Arg Gln
        320                 325                 330 ata ttc cgt gaa ctt gaa atg atg tat tat ggg aaa acc aca tca gcc     1059
Ile Phe Arg Glu Leu Glu Met Met Tyr Tyr Gly Lys Thr Thr Ser Ala
    335                 340                 345 aag gat gtt ctc gtg att cgc aaa att cat ccc ttt tta cct tca ttt     1107
Lys Asp Val Leu Val Ile Arg Lys Ile His Pro Phe Leu Pro Ser Phe
350                 355                 360                 365 aag tca gag ttt aca gcc tct gtc cct cta aca cga att cgt gat att     1155
Lys Ser Glu Phe Thr Ala Ser Val Pro Leu Thr Arg Ile Arg Asp Ile
                370                 375                 380 gct cac cgg aat gac atc cca cat gat ctc aag caa gaa atc aag cat     1203
Ala His Arg Asn Asp Ile Pro His Asp Leu Lys Gln Glu Ile Lys His
            385                 390                 395 act ata caa aac aaa ctt cat cgt aat gct gga cct gag gat ctt att     1251
Thr Ile Gln Asn Lys Leu His Arg Asn Ala Gly Pro Glu Asp Leu Ile
        400                 405                 410 gct aca gaa gtc atg ctt gct agg att act aag acc cct gga gaa tac     1299
Ala Thr Glu Val Met Leu Ala Arg Ile Thr Lys Thr Pro Gly Glu Tyr
    415                 420                 425 agt gaa aca ttt gtt gaa caa ttc acg ata ttt tat agc gaa cta aaa     1347
Ser Glu Thr Phe Val Glu Gln Phe Thr Ile Phe Tyr Ser Glu Leu Lys
430                 435                 440                 445 gat ttc ttc aat gct ggc agc cta ttt gag caa ctg gag tcc atc aag     1395
Asp Phe Phe Asn Ala Gly Ser Leu Phe Glu Gln Leu Glu Ser Ile Lys
                450                 455                 460 gaa tct ctg aac gag tca ggc tta gaa gtt ctc tca tcc ttt gtg gaa     1443
Glu Ser Leu Asn Glu Ser Gly Leu Glu Val Leu Ser Ser Phe Val Glu
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 465 |     |     |     |     | 470 |     |     |     |     | 475 |     |     |      |
| acc | aaa | agg | agt | ttg | gac | caa | gtg | gat | cat | gca | gaa | gat | ttg | gat | aaa | 1491 |
| Thr | Lys | Arg | Ser | Leu | Asp | Gln | Val | Asp | His | Ala | Glu | Asp | Leu | Asp | Lys |      |
|     |     |     | 480 |     |     |     |     | 485 |     |     |     |     | 490 |     |     |      |
| aat | gat | acc | att | caa | att | ttg | atg | act | acc | ttg | caa | tca | tta | tct | tct | 1539 |
| Asn | Asp | Thr | Ile | Gln | Ile | Leu | Met | Thr | Thr | Leu | Gln | Ser | Leu | Ser | Ser |      |
|     |     |     | 495 |     |     |     |     | 500 |     |     |     |     | 505 |     |     |      |
| cta | aga | tcg | gtt | cta | atg | aag | ggc | ctt | gaa | agt | ggc | ctt | aga | aat | gat | 1587 |
| Leu | Arg | Ser | Val | Leu | Met | Lys | Gly | Leu | Glu | Ser | Gly | Leu | Arg | Asn | Asp |      |
| 510 |     |     |     |     | 515 |     |     |     |     | 520 |     |     |     |     | 525 |      |
| gcg | cct | gat | aat | gct | ata | gca | atg | cga | caa | aag | tgg | cgc | ctt | tgt | gaa | 1635 |
| Ala | Pro | Asp | Asn | Ala | Ile | Ala | Met | Arg | Gln | Lys | Trp | Arg | Leu | Cys | Glu |      |
|     |     |     |     | 530 |     |     |     |     | 535 |     |     |     |     | 540 |     |      |
| att | agt | ctt | gag | gat | tat | tca | ttt | gtt | ctg | tta | agc | aga | ttc | atc | aat | 1683 |
| Ile | Ser | Leu | Glu | Asp | Tyr | Ser | Phe | Val | Leu | Leu | Ser | Arg | Phe | Ile | Asn |      |
|     |     |     | 545 |     |     |     |     | 550 |     |     |     |     | 555 |     |     |      |
| act | ctt | gaa | gcc | tta | ggt | gga | tca | gct | tca | ctt | gca | aag | gat | gta | gct | 1731 |
| Thr | Leu | Glu | Ala | Leu | Gly | Gly | Ser | Ala | Ser | Leu | Ala | Lys | Asp | Val | Ala |      |
|     |     |     | 560 |     |     |     |     | 565 |     |     |     |     | 570 |     |     |      |
| aga | aat | act | act | cta | tgg | gat | act | act | ctt | gat | gcc | ctt | gtc | att | ggc | 1779 |
| Arg | Asn | Thr | Thr | Leu | Trp | Asp | Thr | Thr | Leu | Asp | Ala | Leu | Val | Ile | Gly |      |
|     | 575 |     |     |     |     | 580 |     |     |     |     | 585 |     |     |     |     |      |
| atc | aat | caa | gtt | agc | ttt | tca | ggt | tgg | aaa | aca | gat | gaa | tgt | att | gcc | 1827 |
| Ile | Asn | Gln | Val | Ser | Phe | Ser | Gly | Trp | Lys | Thr | Asp | Glu | Cys | Ile | Ala |      |
| 590 |     |     |     |     | 595 |     |     |     |     | 600 |     |     |     |     | 605 |      |
| ata | ggg | aat | gag | att | ctt | tcc | tgg | aag | caa | aaa | ggt | cta | tct | gaa | agt | 1875 |
| Ile | Gly | Asn | Glu | Ile | Leu | Ser | Trp | Lys | Gln | Lys | Gly | Leu | Ser | Glu | Ser |      |
|     |     |     |     | 610 |     |     |     |     | 615 |     |     |     |     | 620 |     |      |
| gaa | ggt | tgt | gaa | gat | ggg | aaa | tat | att | tgg | tca | cta | aga | ctt | aaa | gct | 1923 |
| Glu | Gly | Cys | Glu | Asp | Gly | Lys | Tyr | Ile | Trp | Ser | Leu | Arg | Leu | Lys | Ala |      |
|     |     |     | 625 |     |     |     |     | 630 |     |     |     |     | 635 |     |     |      |
| aca | ctg | gac | aga | gca | cgg | aga | tta | acg | gaa | gag | tac | tct | gaa | gca | ctt | 1971 |
| Thr | Leu | Asp | Arg | Ala | Arg | Arg | Leu | Thr | Glu | Glu | Tyr | Ser | Glu | Ala | Leu |      |
|     |     |     | 640 |     |     |     |     | 645 |     |     |     |     | 650 |     |     |      |
| ctt | tct | ata | ttc | cct | gaa | aaa | gta | atg | gtt | att | ggg | aaa | gcc | ctt | gga | 2019 |
| Leu | Ser | Ile | Phe | Pro | Glu | Lys | Val | Met | Val | Ile | Gly | Lys | Ala | Leu | Gly |      |
|     |     |     | 655 |     |     |     |     | 660 |     |     |     |     | 665 |     |     |      |
| ata | cca | gat | aac | agt | gtg | aga | act | tac | aca | gag | gca | gaa | att | cgt | gct | 2067 |
| Ile | Pro | Asp | Asn | Ser | Val | Arg | Thr | Tyr | Thr | Glu | Ala | Glu | Ile | Arg | Ala |      |
| 670 |     |     |     |     | 675 |     |     |     |     | 680 |     |     |     |     | 685 |      |
| ggc | att | gtt | ttt | cag | gta | tct | aaa | cta | tgc | aca | gta | ctt | cag | aaa | gca | 2115 |
| Gly | Ile | Val | Phe | Gln | Val | Ser | Lys | Leu | Cys | Thr | Val | Leu | Gln | Lys | Ala |      |
|     |     |     |     | 690 |     |     |     |     | 695 |     |     |     |     | 700 |     |      |
| att | cga | gaa | gta | ctt | gga | tca | act | ggc | tgg | gat | gtt | ctt | gtt | cct | gga | 2163 |
| Ile | Arg | Glu | Val | Leu | Gly | Ser | Thr | Gly | Trp | Asp | Val | Leu | Val | Pro | Gly |      |
|     |     |     | 705 |     |     |     |     | 710 |     |     |     |     | 715 |     |     |      |
| gtg | gcc | cat | gga | act | ctg | atg | cgg | gtg | gaa | aga | att | ctt | cct | gga | tca | 2211 |
| Val | Ala | His | Gly | Thr | Leu | Met | Arg | Val | Glu | Arg | Ile | Leu | Pro | Gly | Ser |      |
|     |     |     | 720 |     |     |     |     | 725 |     |     |     |     | 730 |     |     |      |
| tta | cct | tca | tct | gtc | aaa | gaa | cct | gtg | gtt | cta | att | gta | gat | aag | gct | 2259 |
| Leu | Pro | Ser | Ser | Val | Lys | Glu | Pro | Val | Val | Leu | Ile | Val | Asp | Lys | Ala |      |
|     |     |     | 735 |     |     |     |     | 740 |     |     |     |     | 745 |     |     |      |
| gat | gga | gat | gaa | gag | gtc | aaa | gct | gct | ggg | gat | aat | ata | gtt | ggt | gtt | 2307 |
| Asp | Gly | Asp | Glu | Glu | Val | Lys | Ala | Ala | Gly | Asp | Asn | Ile | Val | Gly | Val |      |
| 750 |     |     |     |     | 755 |     |     |     |     | 760 |     |     |     |     | 765 |      |
| att | ctt | ctt | cag | gaa | cta | cct | cac | ctt | tca | cat | ctt | ggt | gtt | aga | gct | 2355 |
| Ile | Leu | Leu | Gln | Glu | Leu | Pro | His | Leu | Ser | His | Leu | Gly | Val | Arg | Ala |      |
|     |     |     |     | 770 |     |     |     |     | 775 |     |     |     |     | 780 |     |      |
| cgt | caa | gag | aat | gtt | gta | ttt | gta | act | tgt | gaa | tat | gat | gac | aca | gtt | 2403 |
| Arg | Gln | Glu | Asn | Val | Val | Phe | Val | Thr | Cys | Glu | Tyr | Asp | Asp | Thr | Val |      |

-continued

```
                785                 790                 795
aca gat gtg tat ttg ctt gag gga aaa tat atc aga tta gaa gca tca    2451
Thr Asp Val Tyr Leu Leu Glu Gly Lys Tyr Ile Arg Leu Glu Ala Ser
        800                 805                 810 tcc atc aat gtc aat ctc tca ata gtt tca gaa aaa aat gac aat gct    2499
Ser Ile Asn Val Asn Leu Ser Ile Val Ser Glu Lys Asn Asp Asn Ala
815                 820                 825 gtc tct aca gaa cca aat agt aca ggg aat cca ttt caa cag aaa ctc    2547
Val Ser Thr Glu Pro Asn Ser Thr Gly Asn Pro Phe Gln Gln Lys Leu
    830                 835                 840                 845 caa aat gaa ttc tct cta cca tcg gat atc gag atg cca ctg caa atg    2595
Gln Asn Glu Phe Ser Leu Pro Ser Asp Ile Glu Met Pro Leu Gln Met
            850                 855                 860 tct aag caa aaa agc aaa tca gga gtg aat ggt agt ttt gct gct ctt    2643
Ser Lys Gln Lys Ser Lys Ser Gly Val Asn Gly Ser Phe Ala Ala Leu
    865                 870                 875 gag ctt tca gaa gct tca gtg gaa tca gct ggt gca aaa gct gct gca    2691
Glu Leu Ser Glu Ala Ser Val Glu Ser Ala Gly Ala Lys Ala Ala Ala
        880                 885                 890 tgc aga act ctt tct gtt ctt gct tca ttg tct aat aaa gtc tat agt    2739
Cys Arg Thr Leu Ser Val Leu Ala Ser Leu Ser Asn Lys Val Tyr Ser
895                 900                 905 gat caa gga gtt cca gca gcc ttt aga gtc cct tct ggt gct gtg ata    2787
Asp Gln Gly Val Pro Ala Ala Phe Arg Val Pro Ser Gly Ala Val Ile
910                 915                 920                 925 cca ttt gga tca atg gag gat gcg ctc aag aaa agt gga tca ctg gaa    2835
Pro Phe Gly Ser Met Glu Asp Ala Leu Lys Lys Ser Gly Ser Leu Glu
            930                 935                 940 tcc ttt aca agc ctt cta gaa aag att gaa aca gcc aaa gtc gaa aat    2883
Ser Phe Thr Ser Leu Leu Glu Lys Ile Glu Thr Ala Lys Val Glu Asn
    945                 950                 955 ggt gaa gtt gat agc ctg gcg ttg gag cta caa gca ata att tca cat    2931
Gly Glu Val Asp Ser Leu Ala Leu Glu Leu Gln Ala Ile Ile Ser His
        960                 965                 970 ctt tcc cca ccg gag gag act att ata ttt ctc aaa aga atc ttc cca    2979
Leu Ser Pro Pro Glu Glu Thr Ile Ile Phe Leu Lys Arg Ile Phe Pro
975                 980                 985 cag gat gtc cgg ttg att gtt aga tct agt gct aat gtg gag gat ttg    3027
Gln Asp Val Arg Leu Ile Val Arg Ser Ser Ala Asn Val Glu Asp Leu
990                 995                 1000                1005 gct ggt atg tca gct gct ggt ctc tat gat tca att ccc aat gtc        3072
Ala Gly Met Ser Ala Ala Gly Leu Tyr Asp Ser Ile Pro Asn Val
            1010                1015                1020 agt ctc atg gac cca tgt gcc ttt gga gct gcg gtt ggg aag gtt        3117
Ser Leu Met Asp Pro Cys Ala Phe Gly Ala Ala Val Gly Lys Val
        1025                1030                1035 tgg gct tct tta tac aca agg aga gcc atc cta agc cgt cga gcc        3162
Trp Ala Ser Leu Tyr Thr Arg Arg Ala Ile Leu Ser Arg Arg Ala
    1040                1045                1050 gct ggt gtt tat cag aga gac gcg aca atg gct gtt ctt gtc caa        3207
Ala Gly Val Tyr Gln Arg Asp Ala Thr Met Ala Val Leu Val Gln
1055                1060                1065 gaa ata ctg cag cca gat ctc tcc ttc gtg ctt cat act gtt tgc        3252
Glu Ile Leu Gln Pro Asp Leu Ser Phe Val Leu His Thr Val Cys
            1070                1075                1080 ccc gct gac cat gac ccc aag gtt gtc cag gct gag gtc gcc cct        3297
Pro Ala Asp His Asp Pro Lys Val Val Gln Ala Glu Val Ala Pro
        1085                1090                1095 ggg ctg ggt gaa acg ctt gct tca gga acc cgt ggc acc ccg tgg        3342
Gly Leu Gly Glu Thr Leu Ala Ser Gly Thr Arg Gly Thr Pro Trp
```

-continued

```
                  1100                1105                1110
agg ctg tca tgt  aac aaa ttc gat  gga aaa gtt gcc  act ctt gcc           3387
Arg Leu Ser Cys  Asn Lys Phe Asp  Gly Lys Val Ala  Thr Leu Ala
                 1115                1120                1125 ttt tca aat ttc  agt gag gag atg  gtg gtg cac aac  tct ggt cct           3432
Phe Ser Asn Phe  Ser Glu Glu Met  Val Val His Asn  Ser Gly Pro
                 1130                1135                1140 gcc aat gga gaa  gta att cgt ctt  act gtt gat tac  agc aag aag           3477
Ala Asn Gly Glu  Val Ile Arg Leu  Thr Val Asp Tyr  Ser Lys Lys
                 1145                1150                1155 cca ttg tcg gtt  gat aca acc ttt  agg aag cag ttt  ggt cag cga           3522
Pro Leu Ser Val  Asp Thr Thr Phe  Arg Lys Gln Phe  Gly Gln Arg
                 1160                1165                1170 ctg gct gcg att  ggc cag tat ctg  gag cag aag ttc  ggg agt gca           3567
Leu Ala Ala Ile  Gly Gln Tyr Leu  Glu Gln Lys Phe  Gly Ser Ala
                 1175                1180                1185 cag gat gtg gaa  ggt tgc ctg gtt  ggg aaa gat att  ttt ata gtg           3612
Gln Asp Val Glu  Gly Cys Leu Val  Gly Lys Asp Ile  Phe Ile Val
                 1190                1195                1200 caa agc agg cca  cag cca tag aagccgaatt c                                3644
Gln Ser Arg Pro  Gln Pro
                 1205
```

<210> SEQ ID NO 4
<211> LENGTH: 1206
<212> TYPE: PRT
<213> ORGANISM: Oryza sativa

<400> SEQUENCE: 4

```
Met Thr Ser Leu Arg Pro Leu Glu Thr Ser Leu Ser Ile Gly Gly Arg
1               5                   10                  15

Pro Arg Arg Gly Leu Val Leu Pro Pro Gly Val Gly Ala Gly Val
            20                  25                  30

Leu Leu Arg Arg Gly Ala Met Ala Leu Pro Gly Arg Arg Gly Phe Ala
        35                  40                  45

Cys Arg Gly Arg Ser Ala Ala Ser Ala Ala Glu Arg Thr Lys Glu Lys
    50                  55                  60

Lys Arg Arg Asp Ser Ser Lys Gln Pro Leu Val His Leu Gln Val Cys
65                  70                  75                  80

Leu Glu His Gln Val Lys Phe Gly Glu His Val Gly Ile Ile Gly Ser
                85                  90                  95

Thr Lys Glu Leu Gly Ser Trp Gly Glu Gln Val Glu Leu Glu Trp Thr
            100                 105                 110

Thr Asn Gly Trp Val Cys Gln Leu Lys Leu Pro Gly Glu Thr Leu Val
        115                 120                 125

Glu Phe Lys Phe Val Ile Phe Leu Val Gly Gly Lys Asp Lys Ile Trp
    130                 135                 140

Glu Asp Gly Asn Asn Arg Val Glu Leu Pro Lys Asp Gly Lys Phe
145                 150                 155                 160

Asp Ile Val Cys His Trp Asn Arg Thr Glu Glu Pro Leu Glu Leu Leu
                165                 170                 175

Gly Thr Pro Lys Phe Glu Leu Val Gly Glu Ala Glu Lys Asn Thr Gly
            180                 185                 190

Glu Asp Ala Ser Ala Ser Val Thr Phe Ala Pro Glu Lys Val Gln Asp
        195                 200                 205

Ile Ser Val Val Glu Asn Gly Asp Pro Ala Pro Glu Ala Glu Ser Ser
    210                 215                 220
```

```
Lys Phe Gly Gly Gln Trp Gln Gly Ser Lys Thr Val Phe Met Arg Ser
225                 230                 235                 240

Asn Glu His Leu Asn Lys Glu Ala Asp Arg Met Trp Asp Thr Thr Gly
            245                 250                 255

Leu Asp Gly Ile Ala Leu Lys Leu Val Glu Gly Asp Lys Ala Ser Arg
        260                 265                 270

Asn Trp Trp Arg Lys Leu Glu Val Val Arg Gly Ile Leu Ser Glu Ser
    275                 280                 285

Phe Asp Asp Gln Ser Arg Leu Gly Ala Leu Val Tyr Ser Ala Ile Tyr
290                 295                 300

Leu Lys Trp Ile Tyr Thr Gly Gln Ile Ser Cys Phe Glu Asp Gly Gly
305                 310                 315                 320

His His Arg Pro Asn Lys His Ala Glu Ile Ser Arg Gln Ile Phe Arg
                325                 330                 335

Glu Leu Glu Met Met Tyr Tyr Gly Lys Thr Thr Ser Ala Lys Asp Val
            340                 345                 350

Leu Val Ile Arg Lys Ile His Pro Phe Leu Pro Ser Phe Lys Ser Glu
        355                 360                 365

Phe Thr Ala Ser Val Pro Leu Thr Arg Ile Arg Asp Ile Ala His Arg
370                 375                 380

Asn Asp Ile Pro His Asp Leu Lys Gln Glu Ile Lys His Thr Ile Gln
385                 390                 395                 400

Asn Lys Leu His Arg Asn Ala Gly Pro Glu Asp Leu Ile Ala Thr Glu
                405                 410                 415

Val Met Leu Ala Arg Ile Thr Lys Thr Pro Gly Glu Tyr Ser Glu Thr
            420                 425                 430

Phe Val Glu Gln Phe Thr Ile Phe Tyr Ser Glu Leu Lys Asp Phe Phe
        435                 440                 445

Asn Ala Gly Ser Leu Phe Glu Gln Leu Glu Ser Ile Lys Glu Ser Leu
450                 455                 460

Asn Glu Ser Gly Leu Glu Val Leu Ser Ser Phe Val Glu Thr Lys Arg
465                 470                 475                 480

Ser Leu Asp Gln Val Asp His Ala Glu Asp Leu Asp Lys Asn Asp Thr
                485                 490                 495

Ile Gln Ile Leu Met Thr Thr Leu Gln Ser Leu Ser Ser Leu Arg Ser
            500                 505                 510

Val Leu Met Lys Gly Leu Glu Ser Gly Leu Arg Asn Asp Ala Pro Asp
        515                 520                 525

Asn Ala Ile Ala Met Arg Gln Lys Trp Arg Leu Cys Glu Ile Ser Leu
530                 535                 540

Glu Asp Tyr Ser Phe Val Leu Leu Ser Arg Phe Ile Asn Thr Leu Glu
545                 550                 555                 560

Ala Leu Gly Gly Ser Ala Ser Leu Ala Lys Asp Val Ala Arg Asn Thr
                565                 570                 575

Thr Leu Trp Asp Thr Thr Leu Asp Ala Leu Val Ile Gly Ile Asn Gln
            580                 585                 590

Val Ser Phe Ser Gly Trp Lys Thr Asp Glu Cys Ile Ala Ile Gly Asn
        595                 600                 605

Glu Ile Leu Ser Trp Lys Gln Lys Gly Leu Ser Glu Ser Glu Gly Cys
610                 615                 620

Glu Asp Gly Lys Tyr Ile Trp Ser Leu Arg Leu Lys Ala Thr Leu Asp
625                 630                 635                 640

Arg Ala Arg Arg Leu Thr Glu Glu Tyr Ser Glu Ala Leu Leu Ser Ile
                645                 650                 655
```

```
Phe Pro Glu Lys Val Met Val Ile Gly Lys Ala Leu Gly Ile Pro Asp
            660                 665                 670

Asn Ser Val Arg Thr Tyr Thr Glu Ala Glu Ile Arg Ala Gly Ile Val
        675                 680                 685

Phe Gln Val Ser Lys Leu Cys Thr Val Leu Gln Lys Ala Ile Arg Glu
    690                 695                 700

Val Leu Gly Ser Thr Gly Trp Asp Val Leu Pro Gly Val Ala His
705                 710                 715                 720

Gly Thr Leu Met Arg Val Glu Arg Ile Leu Pro Gly Ser Leu Pro Ser
                725                 730                 735

Ser Val Lys Glu Pro Val Val Leu Ile Val Asp Lys Ala Asp Gly Asp
            740                 745                 750

Glu Glu Val Lys Ala Ala Gly Asp Asn Ile Val Gly Val Ile Leu Leu
        755                 760                 765

Gln Glu Leu Pro His Leu Ser His Leu Gly Val Arg Ala Arg Gln Glu
    770                 775                 780

Asn Val Val Phe Val Thr Cys Glu Tyr Asp Asp Thr Val Thr Asp Val
785                 790                 795                 800

Tyr Leu Leu Glu Gly Lys Tyr Ile Arg Leu Glu Ala Ser Ser Ile Asn
                805                 810                 815

Val Asn Leu Ser Ile Val Ser Glu Lys Asn Asp Asn Ala Val Ser Thr
            820                 825                 830

Glu Pro Asn Ser Thr Gly Asn Pro Phe Gln Gln Lys Leu Gln Asn Glu
        835                 840                 845

Phe Ser Leu Pro Ser Asp Ile Glu Met Pro Leu Gln Met Ser Lys Gln
850                 855                 860

Lys Ser Lys Ser Gly Val Asn Gly Ser Phe Ala Ala Leu Glu Leu Ser
865                 870                 875                 880

Glu Ala Ser Val Glu Ser Ala Gly Ala Lys Ala Ala Cys Arg Thr
                885                 890                 895

Leu Ser Val Leu Ala Ser Leu Ser Asn Lys Val Tyr Ser Asp Gln Gly
            900                 905                 910

Val Pro Ala Ala Phe Arg Val Pro Ser Gly Ala Val Ile Pro Phe Gly
        915                 920                 925

Ser Met Glu Asp Ala Leu Lys Lys Ser Gly Ser Leu Glu Ser Phe Thr
    930                 935                 940

Ser Leu Leu Glu Lys Ile Glu Thr Ala Lys Val Glu Asn Gly Glu Val
945                 950                 955                 960

Asp Ser Leu Ala Leu Glu Leu Gln Ala Ile Ile Ser His Leu Ser Pro
                965                 970                 975

Pro Glu Glu Thr Ile Ile Phe Leu Lys Arg Ile Phe Pro Gln Asp Val
            980                 985                 990

Arg Leu Ile Val Arg Ser Ser Ala Asn Val Glu Asp Leu Ala Gly Met
        995                 1000                1005

Ser Ala Ala Gly Leu Tyr Asp Ser Ile Pro Asn Val Ser Leu Met
    1010                1015                1020

Asp Pro Cys Ala Phe Gly Ala Ala Val Gly Lys Val Trp Ala Ser
    1025                1030                1035

Leu Tyr Thr Arg Arg Ala Ile Leu Ser Arg Arg Ala Ala Gly Val
    1040                1045                1050

Tyr Gln Arg Asp Ala Thr Met Ala Val Leu Val Gln Glu Ile Leu
    1055                1060                1065

Gln Pro Asp Leu Ser Phe Val Leu His Thr Val Cys Pro Ala Asp
```

-continued

His Asp Pro Lys Val Val Gln Ala Glu Val Ala Pro Gly Leu Gly
        1085                1090                1095

Glu Thr Leu Ala Ser Gly Thr Arg Gly Thr Pro Trp Arg Leu Ser
    1100                1105                1110

Cys Asn Lys Phe Asp Gly Lys Val Ala Thr Leu Ala Phe Ser Asn
1115                1120                1125

Phe Ser Glu Glu Met Val Val His Asn Ser Gly Pro Ala Asn Gly
    1130                1135                1140

Glu Val Ile Arg Leu Thr Val Asp Tyr Ser Lys Lys Pro Leu Ser
    1145                1150                1155

Val Asp Thr Thr Phe Arg Lys Gln Phe Gly Gln Arg Leu Ala Ala
    1160                1165                1170

Ile Gly Gln Tyr Leu Glu Gln Lys Phe Gly Ser Ala Gln Asp Val
    1175                1180                1185

Glu Gly Cys Leu Val Gly Lys Asp Ile Phe Ile Val Gln Ser Arg
    1190                1195                1200

Pro Gln Pro
    1205

<210> SEQ ID NO 5
<211> LENGTH: 12
<212> TYPE: PRT
<213> ORGANISM: Oryza sativa, Arabidopsis thaliana, Sorghum bicolor

<400> SEQUENCE: 5

Leu Pro His Leu Ser His Leu Gly Val Arg Ala Arg
1               5                   10

<210> SEQ ID NO 6
<211> LENGTH: 7
<212> TYPE: PRT
<213> ORGANISM: Hordeum vulgare

<400> SEQUENCE: 6

Ser Arg Arg Val Ala Gly Val
1               5

<210> SEQ ID NO 7
<211> LENGTH: 7
<212> TYPE: PRT
<213> ORGANISM: Hordeum vulgare

<400> SEQUENCE: 7

Val Glu Ala Glu Val Ala Pro
1               5

<210> SEQ ID NO 8
<211> LENGTH: 9
<212> TYPE: PRT
<213> ORGANISM: Hordeum vulgare

<400> SEQUENCE: 8

His Thr Val Ser Pro Ser Asp His Asp
1               5

<210> SEQ ID NO 9
<211> LENGTH: 807
<212> TYPE: DNA
<213> ORGANISM: Hordeum vulgare
<220> FEATURE:
<221> NAME/KEY: CDS

```
<222> LOCATION: (3)..(590)
<223> OTHER INFORMATION:

<400> SEQUENCE: 9 cg gca cga gga gtc ctc ccc aat gtg agc ctc tcg gac cca acc aac      47
   Ala Arg Gly Val Leu Pro Asn Val Ser Leu Ser Asp Pro Thr Asn
   1               5                   10                  15 ttc ggg tct gca gta gcg cgg gtc tgg gcc tcg ctg tac act cgg agg     95
Phe Gly Ser Ala Val Ala Arg Val Trp Ala Ser Leu Tyr Thr Arg Arg
                20                  25                  30 gcc atc ctc agc cgc cgg gtg gct ggc gtg ccc cag agg gac gcc aag    143
Ala Ile Leu Ser Arg Arg Val Ala Gly Val Pro Gln Arg Asp Ala Lys
            35                  40                  45 atg gct gtc ctg gtg cag gag atg ctg gag cca gag cta tcc ttc gtg    191
Met Ala Val Leu Val Gln Glu Met Leu Glu Pro Glu Leu Ser Phe Val
        50                  55                  60 ctc cac acg gtc agc ccc tcg gac cac gac acc agg gtc gtc gag gct    239
Leu His Thr Val Ser Pro Ser Asp His Asp Thr Arg Val Val Glu Ala
    65                  70                  75 gag gtt gcc ccg ggg ctg ggc gag acc ctt gcc gct ggc acc cgc ggc    287
Glu Val Ala Pro Gly Leu Gly Glu Thr Leu Ala Ala Gly Thr Arg Gly
80                  85                  90                  95 acc ccg tgg cgt ctc tcc tgc gac aag ttc gac acc gac gtc gcc acc    335
Thr Pro Trp Arg Leu Ser Cys Asp Lys Phe Asp Thr Asp Val Ala Thr
                100                 105                 110 ctg gcc ttc gcc aac ttc agt gag gag atg cgg gtg ctc ggc tcg ggc    383
Leu Ala Phe Ala Asn Phe Ser Glu Glu Met Arg Val Leu Gly Ser Gly
            115                 120                 125 ccc gcc gac ggc gag gtg gtg agg ctc act gtc gac tac agc acg aag    431
Pro Ala Asp Gly Glu Val Val Arg Leu Thr Val Asp Tyr Ser Thr Lys
        130                 135                 140 ctg ctc tcc gtc gac agg acc ttc agg cag aag ttc ggt cag cgg ctg    479
Leu Leu Ser Val Asp Arg Thr Phe Arg Gln Lys Phe Gly Gln Arg Leu
    145                 150                 155 gcc gcc gtg ggg cag tac ctg gag cag agg ttc ggg agc gcc cag gac    527
Ala Ala Val Gly Gln Tyr Leu Glu Gln Arg Phe Gly Ser Ala Gln Asp
160                 165                 170                 175 gtg gag ggc tgc atg gtc tgg gaa gac atc tac ata gtg cag agc atg    575
Val Glu Gly Cys Met Val Trp Glu Asp Ile Tyr Ile Val Gln Ser Met
                180                 185                 190 cca caa ccg ctg tag agtcatccgt aataatgttt agatgagcaa agttttggtt    630
Pro Gln Pro Leu
            195 ggtgaaataa aatttgccga aaatcccatg gcaaataag tcaggtatga agagcccgcc   690 tgcgaaacca actgattcta aataatgttt tgaattcgtg tttaaattat gggacgtgaa   750 caatgatttc cttggaatgc atgcattgta agttttaaaa aaaaaaaaa aaaaaaa      807

<210> SEQ ID NO 10
<211> LENGTH: 195
<212> TYPE: PRT
<213> ORGANISM: Hordeum vulgare

<400> SEQUENCE: 10

Ala Arg Gly Val Leu Pro Asn Val Ser Leu Ser Asp Pro Thr Asn Phe
1               5                   10                  15

Gly Ser Ala Val Ala Arg Val Trp Ala Ser Leu Tyr Thr Arg Arg Ala
                20                  25                  30

Ile Leu Ser Arg Arg Val Ala Gly Val Pro Gln Arg Asp Ala Lys Met
            35                  40                  45
```

```
Ala Val Leu Val Gln Glu Met Leu Glu Pro Glu Leu Ser Phe Val Leu
            50                  55                  60

His Thr Val Ser Pro Ser Asp His Asp Thr Arg Val Val Glu Ala Glu
 65                  70                  75                  80

Val Ala Pro Gly Leu Gly Glu Thr Leu Ala Ala Gly Thr Arg Gly Thr
                     85                  90                  95

Pro Trp Arg Leu Ser Cys Asp Lys Phe Asp Thr Asp Val Ala Thr Leu
                100                 105                 110

Ala Phe Ala Asn Phe Ser Glu Glu Met Arg Val Leu Gly Ser Gly Pro
            115                 120                 125

Ala Asp Gly Glu Val Val Arg Leu Thr Val Asp Tyr Ser Thr Lys Leu
            130                 135                 140

Leu Ser Val Asp Arg Thr Phe Arg Gln Lys Phe Gly Gln Arg Leu Ala
145                 150                 155                 160

Ala Val Gly Gln Tyr Leu Glu Gln Arg Phe Gly Ser Ala Gln Asp Val
                165                 170                 175

Glu Gly Cys Met Val Trp Glu Asp Ile Tyr Ile Val Gln Ser Met Pro
            180                 185                 190

Gln Pro Leu
        195

<210> SEQ ID NO 11
<211> LENGTH: 9
<212> TYPE: PRT
<213> ORGANISM: Solanum tuberosum

<400> SEQUENCE: 11

Pro Glu Glu Cys Lys Ala Val Gly Asn
1               5

<210> SEQ ID NO 12
<211> LENGTH: 7
<212> TYPE: PRT
<213> ORGANISM: Solanum tuberosum

<400> SEQUENCE: 12

Thr Glu Glu Tyr Ser Glu Thr
1               5

<210> SEQ ID NO 13
<211> LENGTH: 7
<212> TYPE: PRT
<213> ORGANISM: Solanum tuberosum

<400> SEQUENCE: 13

Arg Phe Val Asn Ala Val Glu
1               5

<210> SEQ ID NO 14
<211> LENGTH: 7
<212> TYPE: PRT
<213> ORGANISM: Solanum tuberosum

<400> SEQUENCE: 14

Glu Gly Ser Glu Asp Gly Lys
1               5

<210> SEQ ID NO 15
<211> LENGTH: 403
<212> TYPE: DNA
<213> ORGANISM: Solanum tuberosum
<220> FEATURE:
```

<221> NAME/KEY: CDS
<222> LOCATION: (1)..(402)
<223> OTHER INFORMATION:

<400> SEQUENCE: 15

| | | | | | | | | | | | | | | | | |
|---|---|---|---|---|---|---|---|---|---|---|---|---|---|---|---|---|
| gcg | gat | gct | tca | ata | gct | atg | cgt | cag | aag | tgg | cgt | ctc | tgc | gaa | atc | 48 |
| Ala | Asp | Ala | Ser | Ile | Ala | Met | Arg | Gln | Lys | Trp | Arg | Leu | Cys | Glu | Ile | |
| 1 | | | | 5 | | | | | 10 | | | | | 15 | | |
| ggg | ctt | gaa | gac | tat | gca | ttt | gtt | ctt | ttg | agc | agg | ttt | gtg | aat | gca | 96 |
| Gly | Leu | Glu | Asp | Tyr | Ala | Phe | Val | Leu | Leu | Ser | Arg | Phe | Val | Asn | Ala | |
| | | | 20 | | | | | 25 | | | | | 30 | | | |
| gtt | gaa | gct | cta | ggc | gga | gct | gat | tgg | ctt | gca | gag | aat | gta | aca | gtg | 144 |
| Val | Glu | Ala | Leu | Gly | Gly | Ala | Asp | Trp | Leu | Ala | Glu | Asn | Val | Thr | Val | |
| | 35 | | | | | 40 | | | | | 45 | | | | | |
| aaa | aac | att | agt | tct | tgg | aat | gat | cca | att | gga | gca | ctt | aca | gtt | gga | 192 |
| Lys | Asn | Ile | Ser | Ser | Trp | Asn | Asp | Pro | Ile | Gly | Ala | Leu | Thr | Val | Gly | |
| 50 | | | | | 55 | | | | | 60 | | | | | | |
| atc | caa | cag | cta | ggt | ata | tct | ggt | tgg | aag | ccc | gag | gaa | tgc | aaa | gct | 240 |
| Ile | Gln | Gln | Leu | Gly | Ile | Ser | Gly | Trp | Lys | Pro | Glu | Glu | Cys | Lys | Ala | |
| 65 | | | | 70 | | | | | 75 | | | | | 80 | | |
| gtt | gga | aat | gaa | ctt | ttg | tca | tgg | aaa | gaa | agg | ggt | att | tca | gaa | att | 288 |
| Val | Gly | Asn | Glu | Leu | Leu | Ser | Trp | Lys | Glu | Arg | Gly | Ile | Ser | Glu | Ile | |
| | | | 85 | | | | | 90 | | | | | 95 | | | |
| gaa | ggc | agc | gaa | gat | ggt | aag | act | ata | tgg | gca | tta | aga | cta | aaa | gcg | 336 |
| Glu | Gly | Ser | Glu | Asp | Gly | Lys | Thr | Ile | Trp | Ala | Leu | Arg | Leu | Lys | Ala | |
| | | | 100 | | | | | 105 | | | | | 110 | | | |
| act | ctt | gat | aga | agt | cga | agg | tta | act | gag | gag | tat | tcc | gag | aca | ctt | 384 |
| Thr | Leu | Asp | Arg | Ser | Arg | Arg | Leu | Thr | Glu | Glu | Tyr | Ser | Glu | Thr | Leu | |
| | | | 115 | | | | | 120 | | | | | 125 | | | |
| ctc | caa | ata | ttc | cct | gaa | a | | | | | | | | | | 403 |
| Leu | Gln | Ile | Phe | Pro | Glu | | | | | | | | | | | |
| | | | 130 | | | | | | | | | | | | | |

<210> SEQ ID NO 16
<211> LENGTH: 134
<212> TYPE: PRT
<213> ORGANISM: Solanum tuberosum

<400> SEQUENCE: 16

Ala Asp Ala Ser Ile Ala Met Arg Gln Lys Trp Arg Leu Cys Glu Ile
1               5                   10                  15

Gly Leu Glu Asp Tyr Ala Phe Val Leu Leu Ser Arg Phe Val Asn Ala
            20                  25                  30

Val Glu Ala Leu Gly Gly Ala Asp Trp Leu Ala Glu Asn Val Thr Val
        35                  40                  45

Lys Asn Ile Ser Ser Trp Asn Asp Pro Ile Gly Ala Leu Thr Val Gly
50                  55                  60

Ile Gln Gln Leu Gly Ile Ser Gly Trp Lys Pro Glu Glu Cys Lys Ala
65                  70                  75                  80

Val Gly Asn Glu Leu Leu Ser Trp Lys Glu Arg Gly Ile Ser Glu Ile
            85                  90                  95

Glu Gly Ser Glu Asp Gly Lys Thr Ile Trp Ala Leu Arg Leu Lys Ala
            100                 105                 110

Thr Leu Asp Arg Ser Arg Arg Leu Thr Glu Glu Tyr Ser Glu Thr Leu
        115                 120                 125

Leu Gln Ile Phe Pro Glu
    130

<210> SEQ ID NO 17
<211> LENGTH: 7

```
<212> TYPE: PRT
<213> ORGANISM: Sorghum bicolor

<400> SEQUENCE: 17

Asp Gly Gly His His Arg Pro
1               5

<210> SEQ ID NO 18
<211> LENGTH: 8
<212> TYPE: PRT
<213> ORGANISM: Sorghum bicolor

<400> SEQUENCE: 18

Asp Ala Pro Asp Ser Ala Ile Ala
1               5

<210> SEQ ID NO 19
<211> LENGTH: 9
<212> TYPE: PRT
<213> ORGANISM: Sorghum bicolor

<400> SEQUENCE: 19

Ile Pro Glu Asn Ser Val Arg Thr Tyr
1               5

<210> SEQ ID NO 20
<211> LENGTH: 6
<212> TYPE: PRT
<213> ORGANISM: Sorghum bicolor

<400> SEQUENCE: 20

Val Asn Lys Ala Asp Gly
1               5

<210> SEQ ID NO 21
<211> LENGTH: 1526
<212> TYPE: DNA
<213> ORGANISM: Sorghum bicolor
<220> FEATURE:
<221> NAME/KEY: CDS
<222> LOCATION: (2)..(1525)
<223> OTHER INFORMATION:

<400> SEQUENCE: 21
```

| | | |
|---|---|---|
| g cac gag gct gaa tat gtt cat gat cag agt cac ctg gag gct ctt aca<br>His Glu Ala Glu Tyr Val His Asp Gln Ser His Leu Glu Ala Leu Thr<br>  1               5                   10                  15 | 49 |
| tat tct gca ata tat cta aag tgg ata tat act ggt caa ata cca tgc<br>Tyr Ser Ala Ile Tyr Leu Lys Trp Ile Tyr Thr Gly Gln Ile Pro Cys<br>              20                  25                  30 | 97 |
| ttt gag gat ggt ggt cac cat cga ccc aat aaa cat gct gag ata tcc<br>Phe Glu Asp Gly Gly His His Arg Pro Asn Lys His Ala Glu Ile Ser<br>          35                  40                  45 | 145 |
| agg caa att ttt cgt gaa att gaa agg ata tac tat ggg gaa aac aca<br>Arg Gln Ile Phe Arg Glu Ile Glu Arg Ile Tyr Tyr Gly Glu Asn Thr<br>      50                  55                  60 | 193 |
| tca gct cag gat ttg ctt gtg ata cgc aag att cat cct tgt cta cct<br>Ser Ala Gln Asp Leu Leu Val Ile Arg Lys Ile His Pro Cys Leu Pro<br>  65                  70                  75                  80 | 241 |
| tca ttt aaa tca gaa ttt act gcc tct gtt cct cta acg att cgt<br>Ser Phe Lys Ser Glu Phe Thr Ala Ser Val Pro Leu Thr Arg Ile Arg<br>                  85                  90                  95 | 289 |
| gat att gct cat cgt aat gac ata cca cat gat ctc aag caa gaa atc<br>Asp Ile Ala His Arg Asn Asp Ile Pro His Asp Leu Lys Gln Glu Ile<br>              100                 105                 110 | 337 |

```
aag cat act ata caa aac aag ctt cac cgg aat gcc ggc cct gag gat    385
Lys His Thr Ile Gln Asn Lys Leu His Arg Asn Ala Gly Pro Glu Asp
        115                 120                 125 ctt att gct act gaa gcc atg ctt gct agg att act aag act cct gga    433
Leu Ile Ala Thr Glu Ala Met Leu Ala Arg Ile Thr Lys Thr Pro Gly
130                 135                 140 gag tac agt gaa gct ttt gtt gaa caa ttc aag acg ttt tat agt gaa    481
Glu Tyr Ser Glu Ala Phe Val Glu Gln Phe Lys Thr Phe Tyr Ser Glu
145                 150                 155                 160 tta aaa gat ttc ttc aat gct ggc agc cta ctg gag caa gtg caa tcc    529
Leu Lys Asp Phe Phe Asn Ala Gly Ser Leu Leu Glu Gln Val Gln Ser
                165                 170                 175 atc gag caa tct ttg gat gag tct ggc tta gaa gct ctc tca tcc ttt    577
Ile Glu Gln Ser Leu Asp Glu Ser Gly Leu Glu Ala Leu Ser Ser Phe
            180                 185                 190 ctg aaa acc aaa aag aat tta gac caa ctg gaa gat gca aaa gat ttg    625
Leu Lys Thr Lys Lys Asn Leu Asp Gln Leu Glu Asp Ala Lys Asp Leu
        195                 200                 205 gat gaa aat ggt ggc gtt caa gtt ttg ttg aaa gcc ttg ctg tcg tta    673
Asp Glu Asn Gly Gly Val Gln Val Leu Leu Lys Ala Leu Leu Ser Leu
    210                 215                 220 tct tat cta aga tca att cta atg aag ggt ctg gaa agt ggc ctt aga    721
Ser Tyr Leu Arg Ser Ile Leu Met Lys Gly Leu Glu Ser Gly Leu Arg
225                 230                 235                 240 aat gat gct cca gat agt gct att gca atg cga caa aag tgg cgt ctt    769
Asn Asp Ala Pro Asp Ser Ala Ile Ala Met Arg Gln Lys Trp Arg Leu
                245                 250                 255 tgt gag atc ggg ctt gaa gat tat tcg ttt gta ttg tta agt aga tac    817
Cys Glu Ile Gly Leu Glu Asp Tyr Ser Phe Val Leu Leu Ser Arg Tyr
            260                 265                 270 atc aat gct ctt gaa gct ttg ggt gga tca gct tca ctt gca gag ggt    865
Ile Asn Ala Leu Glu Ala Leu Gly Gly Ser Ala Ser Leu Ala Glu Gly
        275                 280                 285 ctt cct aca aat aca agt cta tgg gat gat gcc ctt gat gcc ctt gtc    913
Leu Pro Thr Asn Thr Ser Leu Trp Asp Asp Ala Leu Asp Ala Leu Val
    290                 295                 300 att ggc ata aat caa gtt agc ttt tca gga tgg aaa cca aat gag tgt    961
Ile Gly Ile Asn Gln Val Ser Phe Ser Gly Trp Lys Pro Asn Glu Cys
305                 310                 315                 320 act gca ata gtg aat gag ctt ctt tct tgg aag cag aaa ggt cta tct   1009
Thr Ala Ile Val Asn Glu Leu Leu Ser Trp Lys Gln Lys Gly Leu Ser
                325                 330                 335 gaa ttt gaa ggc agt gag gat gga aag tat att tgg gca ctg aga ctc   1057
Glu Phe Glu Gly Ser Glu Asp Gly Lys Tyr Ile Trp Ala Leu Arg Leu
            340                 345                 350 aaa gcc act ctt gat aga tca cga aga cta aca gaa gaa tac tct gaa   1105
Lys Ala Thr Leu Asp Arg Ser Arg Arg Leu Thr Glu Glu Tyr Ser Glu
        355                 360                 365 gca ctt ctt tct ata ttt cct gaa aaa gtc aag gtt ctt ggg aaa gcc   1153
Ala Leu Leu Ser Ile Phe Pro Glu Lys Val Lys Val Leu Gly Lys Ala
    370                 375                 380 ctt gga ata cca gag aac agt gtg aga aca tac act gaa gct gaa att   1201
Leu Gly Ile Pro Glu Asn Ser Val Arg Thr Tyr Thr Glu Ala Glu Ile
385                 390                 395                 400 cgt gct ggt gtt att ttt cac gtc tcg aaa ctt tgc act gta ctt tta   1249
Arg Ala Gly Val Ile Phe His Val Ser Lys Leu Cys Thr Val Leu Leu
                405                 410                 415 aaa gca act cga gca gtt ctt gga tcg tct gtg tgg gat gtt ctt gtt   1297
Lys Ala Thr Arg Ala Val Leu Gly Ser Ser Val Trp Asp Val Leu Val
            420                 425                 430
```

-continued

```
cct gga gtg gcc cat gga gcc ttg ata cag gtt gaa aga ata gct cct      1345
Pro Gly Val Ala His Gly Ala Leu Ile Gln Val Glu Arg Ile Ala Pro
            435                 440                 445 gga tca ttg cca tca tcc atc aaa gaa cct gtc gtg cta gtt gta aac      1393
Gly Ser Leu Pro Ser Ser Ile Lys Glu Pro Val Val Leu Val Val Asn
450                 455                 460 aag gct gat gga gat gaa gag gtc aaa gct gct ggg gat aac ata gtg      1441
Lys Ala Asp Gly Asp Glu Glu Val Lys Ala Ala Gly Asp Asn Ile Val
465                 470                 475                 480 ggt gtt att ctt cta caa gaa tta cct cac cta tca cat ctt ggt gtt      1489
Gly Val Ile Leu Leu Gln Glu Leu Pro His Leu Ser His Leu Gly Val
                485                 490                 495 aga gct cgt caa gag aaa gtt gta ttt gta act tgc g                    1526
Arg Ala Arg Gln Glu Lys Val Val Phe Val Thr Cys
            500                 505
```

<210> SEQ ID NO 22
<211> LENGTH: 508
<212> TYPE: PRT
<213> ORGANISM: Sorghum bicolor

<400> SEQUENCE: 22

```
His Glu Ala Glu Tyr Val His Asp Gln Ser His Leu Glu Ala Leu Thr
1               5                   10                  15

Tyr Ser Ala Ile Tyr Leu Lys Trp Ile Tyr Thr Gly Gln Ile Pro Cys
            20                  25                  30

Phe Glu Asp Gly Gly His His Arg Pro Asn Lys His Ala Glu Ile Ser
        35                  40                  45

Arg Gln Ile Phe Arg Glu Ile Glu Arg Ile Tyr Tyr Gly Glu Asn Thr
    50                  55                  60

Ser Ala Gln Asp Leu Leu Val Ile Arg Lys Ile His Pro Cys Leu Pro
65                  70                  75                  80

Ser Phe Lys Ser Glu Phe Thr Ala Ser Val Pro Leu Thr Arg Ile Arg
                85                  90                  95

Asp Ile Ala His Arg Asn Asp Ile Pro His Asp Leu Lys Gln Glu Ile
            100                 105                 110

Lys His Thr Ile Gln Asn Lys Leu His Arg Asn Ala Gly Pro Glu Asp
        115                 120                 125

Leu Ile Ala Thr Glu Ala Met Leu Ala Arg Ile Thr Lys Thr Pro Gly
    130                 135                 140

Glu Tyr Ser Glu Ala Phe Val Glu Gln Phe Lys Thr Phe Tyr Ser Glu
145                 150                 155                 160

Leu Lys Asp Phe Phe Asn Ala Gly Ser Leu Leu Glu Gln Val Gln Ser
                165                 170                 175

Ile Glu Gln Ser Leu Asp Glu Ser Gly Leu Glu Ala Leu Ser Ser Phe
            180                 185                 190

Leu Lys Thr Lys Lys Asn Leu Asp Gln Leu Glu Asp Ala Lys Asp Leu
        195                 200                 205

Asp Glu Asn Gly Gly Val Gln Val Leu Leu Lys Ala Leu Leu Ser Leu
    210                 215                 220

Ser Tyr Leu Arg Ser Ile Leu Met Lys Gly Leu Glu Ser Gly Leu Arg
225                 230                 235                 240

Asn Asp Ala Pro Asp Ser Ala Ile Ala Met Arg Gln Lys Trp Arg Leu
                245                 250                 255

Cys Glu Ile Gly Leu Glu Asp Tyr Ser Phe Val Leu Leu Ser Arg Tyr
            260                 265                 270
```

```
Ile Asn Ala Leu Glu Ala Leu Gly Gly Ser Ala Ser Leu Ala Glu Gly
        275                 280                 285

Leu Pro Thr Asn Thr Ser Leu Trp Asp Asp Ala Leu Asp Ala Leu Val
        290                 295                 300

Ile Gly Ile Asn Gln Val Ser Phe Ser Gly Trp Lys Pro Asn Glu Cys
305                 310                 315                 320

Thr Ala Ile Val Asn Glu Leu Leu Ser Trp Lys Gln Lys Gly Leu Ser
                325                 330                 335

Glu Phe Glu Gly Ser Glu Asp Gly Lys Tyr Ile Trp Ala Leu Arg Leu
                340                 345                 350

Lys Ala Thr Leu Asp Arg Ser Arg Arg Leu Thr Glu Glu Tyr Ser Glu
                355                 360                 365

Ala Leu Leu Ser Ile Phe Pro Glu Lys Val Lys Val Leu Gly Lys Ala
            370                 375                 380

Leu Gly Ile Pro Glu Asn Ser Val Arg Thr Tyr Thr Glu Ala Glu Ile
385                 390                 395                 400

Arg Ala Gly Val Ile Phe His Val Ser Lys Leu Cys Thr Val Leu Leu
                    405                 410                 415

Lys Ala Thr Arg Ala Val Leu Gly Ser Ser Val Trp Asp Val Leu Val
                420                 425                 430

Pro Gly Val Ala His Gly Ala Leu Ile Gln Val Glu Arg Ile Ala Pro
            435                 440                 445

Gly Ser Leu Pro Ser Ser Ile Lys Glu Pro Val Val Leu Val Val Asn
        450                 455                 460

Lys Ala Asp Gly Asp Glu Val Lys Ala Ala Gly Asp Asn Ile Val
465                 470                 475                 480

Gly Val Ile Leu Leu Gln Glu Leu Pro His Leu Ser His Leu Gly Val
                485                 490                 495

Arg Ala Arg Gln Glu Lys Val Val Phe Val Thr Cys
                500                 505

<210> SEQ ID NO 23
<211> LENGTH: 8
<212> TYPE: PRT
<213> ORGANISM: Triticum aestivum

<400> SEQUENCE: 23

Arg Asn Asp Ala Thr Asp Ala Gly
1               5

<210> SEQ ID NO 24
<211> LENGTH: 8
<212> TYPE: PRT
<213> ORGANISM: Triticum aestivum

<400> SEQUENCE: 24

Gly Asn Thr Ser Val Trp Asp Asp
1               5

<210> SEQ ID NO 25
<211> LENGTH: 509
<212> TYPE: DNA
<213> ORGANISM: Triticum aestivum
<220> FEATURE:
<221> NAME/KEY: CDS
<222> LOCATION: (1)..(507)
<223> OTHER INFORMATION:

<400> SEQUENCE: 25 aat ggc gct ttt gtc gaa caa ttt caa ata ttt tat agc gaa cta aaa      48
```

```
Asn Gly Ala Phe Val Glu Gln Phe Gln Ile Phe Tyr Ser Glu Leu Lys
1               5                   10                  15 gac ttc ttt aat gcc ggc agc ctg ttt gaa caa ctg gaa tcc atc aag       96
Asp Phe Phe Asn Ala Gly Ser Leu Phe Glu Gln Leu Glu Ser Ile Lys
                20                  25                  30 gaa tct ttg aat gat tct ggc tta gaa gca ctg tca tca ttt gtc aaa      144
Glu Ser Leu Asn Asp Ser Gly Leu Glu Ala Leu Ser Ser Phe Val Lys
            35                  40                  45 acc aaa cag agt ttg gac caa gtg gat gct gcg aac att caa gtt gtg      192
Thr Lys Gln Ser Leu Asp Gln Val Asp Ala Ala Asn Ile Gln Val Val
        50                  55                  60 atg aag acc ttg cag tca ttg tct tca ttg aga tca gtt cta atg aag      240
Met Lys Thr Leu Gln Ser Leu Ser Ser Leu Arg Ser Val Leu Met Lys
65                  70                  75                  80 ggc ctt gaa agt ggc ctt aga aat gat gcg act gat gcc ggt ata gca      288
Gly Leu Glu Ser Gly Leu Arg Asn Asp Ala Thr Asp Ala Gly Ile Ala
                85                  90                  95 atg cga caa aag tgg cgc ctt tgt gag att ggt ctt gag gat tat tct      336
Met Arg Gln Lys Trp Arg Leu Cys Glu Ile Gly Leu Glu Asp Tyr Ser
                100                 105                 110 ttt gtt ttg tta agc aga tat atc aat ggt ctt gaa gct tca ggt gga      384
Phe Val Leu Leu Ser Arg Tyr Ile Asn Gly Leu Glu Ala Ser Gly Gly
            115                 120                 125 tca gct tca ctt gca caa tgt gtg gct gga aat aca agt gta tgg gac      432
Ser Ala Ser Leu Ala Gln Cys Val Ala Gly Asn Thr Ser Val Trp Asp
        130                 135                 140 gat acc ctt gat gcc ctt att att ggc gtc aat caa gtt agc ttt tca      480
Asp Thr Leu Asp Ala Leu Ile Ile Gly Val Asn Gln Val Ser Phe Ser
145                 150                 155                 160 ggt tgg aag cca gag gaa tgc att gct at                               509
Gly Trp Lys Pro Glu Glu Cys Ile Ala
                165

<210> SEQ ID NO 26
<211> LENGTH: 169
<212> TYPE: PRT
<213> ORGANISM: Triticum aestivum

<400> SEQUENCE: 26

Asn Gly Ala Phe Val Glu Gln Phe Gln Ile Phe Tyr Ser Glu Leu Lys
1               5                   10                  15

Asp Phe Phe Asn Ala Gly Ser Leu Phe Glu Gln Leu Glu Ser Ile Lys
                20                  25                  30

Glu Ser Leu Asn Asp Ser Gly Leu Glu Ala Leu Ser Ser Phe Val Lys
            35                  40                  45

Thr Lys Gln Ser Leu Asp Gln Val Asp Ala Ala Asn Ile Gln Val Val
        50                  55                  60

Met Lys Thr Leu Gln Ser Leu Ser Ser Leu Arg Ser Val Leu Met Lys
65                  70                  75                  80

Gly Leu Glu Ser Gly Leu Arg Asn Asp Ala Thr Asp Ala Gly Ile Ala
                85                  90                  95

Met Arg Gln Lys Trp Arg Leu Cys Glu Ile Gly Leu Glu Asp Tyr Ser
                100                 105                 110

Phe Val Leu Leu Ser Arg Tyr Ile Asn Gly Leu Glu Ala Ser Gly Gly
            115                 120                 125

Ser Ala Ser Leu Ala Gln Cys Val Ala Gly Asn Thr Ser Val Trp Asp
        130                 135                 140

Asp Thr Leu Asp Ala Leu Ile Ile Gly Val Asn Gln Val Ser Phe Ser
145                 150                 155                 160
```

Gly Trp Lys Pro Glu Glu Cys Ile Ala
            165

<210> SEQ ID NO 27
<211> LENGTH: 27
<212> TYPE: DNA
<213> ORGANISM: Synthetic

<400> SEQUENCE: 27
gactcaacca cataacacac aaagatc                                27

<210> SEQ ID NO 28
<211> LENGTH: 21
<212> TYPE: DNA
<213> ORGANISM: Synthetic

<400> SEQUENCE: 28
tggtaacgag gcaaatgcag a                                      21

<210> SEQ ID NO 29
<211> LENGTH: 25
<212> TYPE: DNA
<213> ORGANISM: Synthetic

<400> SEQUENCE: 29
atctcttatc acaccacctc caatg                                  25

<210> SEQ ID NO 30
<211> LENGTH: 24
<212> TYPE: DNA
<213> ORGANISM: Synthetic

<400> SEQUENCE: 30
ggaaccgata atgcctacat gctc                                   24

<210> SEQ ID NO 31
<211> LENGTH: 39
<212> TYPE: DNA
<213> ORGANISM: Synthetic

<400> SEQUENCE: 31
aaaactcgag gaggatcaat gacgtcgctg cggcccctc                   39

<210> SEQ ID NO 32
<211> LENGTH: 21
<212> TYPE: DNA
<213> ORGANISM: Synthetic

<400> SEQUENCE: 32
ccaggttaag tttggtgagc a                                      21

<210> SEQ ID NO 33
<211> LENGTH: 22
<212> TYPE: DNA
<213> ORGANISM: Synthetic

<400> SEQUENCE: 33
caaagcacga tatctgacct gt                                     22

<210> SEQ ID NO 34
<211> LENGTH: 22
<212> TYPE: DNA
<213> ORGANISM: Synthetic

<400> SEQUENCE: 34
ttgttcgcgg gatattgtca ga    22

<210> SEQ ID NO 35
<211> LENGTH: 24
<212> TYPE: DNA
<213> ORGANISM: Synthetic

<400> SEQUENCE: 35
gacaagggca tcaagagtag tatc    24

<210> SEQ ID NO 36
<211> LENGTH: 20
<212> TYPE: DNA
<213> ORGANISM: Synthetic

<400> SEQUENCE: 36
atgatgcgcc tgataatgct    20

<210> SEQ ID NO 37
<211> LENGTH: 21
<212> TYPE: DNA
<213> ORGANISM: Synthetic

<400> SEQUENCE: 37
ggcaaacagt atgaagcacg a    21

<210> SEQ ID NO 38
<211> LENGTH: 21
<212> TYPE: DNA
<213> ORGANISM: Synthetic

<400> SEQUENCE: 38
catttggatc aatggaggat g    21

<210> SEQ ID NO 39
<211> LENGTH: 23
<212> TYPE: DNA
<213> ORGANISM: Synthetic

<400> SEQUENCE: 39
ctatggctgt ggcctgcttt gca    23

<210> SEQ ID NO 40
<211> LENGTH: 33
<212> TYPE: DNA
<213> ORGANISM: Synthetic

<400> SEQUENCE: 40
aaaactcgag ctatggctgt ggcctgcttt gca    33

<210> SEQ ID NO 41
<211> LENGTH: 28
<212> TYPE: DNA
<213> ORGANISM: Synthetic

<400> SEQUENCE: 41
aaaacaattg gcgcctggag ggaggaga    28

<210> SEQ ID NO 42
<211> LENGTH: 35
<212> TYPE: DNA
<213> ORGANISM: Synthetic

-continued

```
<400> SEQUENCE: 42
aaaacaattg atgatcaatc agacaatcac tagaa                                35

<210> SEQ ID NO 43
<211> LENGTH: 63
<212> TYPE: DNA
<213> ORGANISM: Synthetic

<400> SEQUENCE: 43
tgcaggctgc agagctccta ggctcgagtt aacactagta agcttaatta agatatcatt     60
tac                                                                   63

<210> SEQ ID NO 44
<211> LENGTH: 67
<212> TYPE: DNA
<213> ORGANISM: Synthetic

<400> SEQUENCE: 44
aattgtaaat gatatcttaa ttaagcttac tagtgttaac tcgagcctag gagctctgca     60
gcctgca                                                               67

<210> SEQ ID NO 45
<211> LENGTH: 28
<212> TYPE: DNA
<213> ORGANISM: Synthetic

<400> SEQUENCE: 45
ttttctcgag gtccgccttg tttctcct                                        28

<210> SEQ ID NO 46
<211> LENGTH: 26
<212> TYPE: DNA
<213> ORGANISM: Synthetic

<400> SEQUENCE: 46
ttttctcgag ctgcacgggt ccagga                                          26
```